(12) United States Patent
Anzalone et al.

(10) Patent No.: US 8,222,431 B2
(45) Date of Patent: Jul. 17, 2012

(54) PROCESS FOR SYNTHESIZING PHOSPHONIC AND PHOSPHINIC ACID COMPOUNDS

(75) Inventors: Luigi Anzalone, West Chester, PA (US); Daniel J. Pippel, Del Mar, CA (US); Neelakandha S. Mani, San Diego, CA (US); Penina Feibush, Ambler, PA (US); Ilias K. Dorziotis, Somerville, NJ (US); Stefan Horns, Schaffhausen (DE); Frank J. Villani, Jr., Perkasie, PA (US)

(73) Assignee: Janssen Pharmaceutica N.V. (BE)

( * ) Notice: Subject to any disclaimer, the term of this patent is extended or adjusted under 35 U.S.C. 154(b) by 431 days.

(21) Appl. No.: 12/288,044

(22) Filed: Oct. 16, 2008

(65) Prior Publication Data

US 2009/0124801 A1 May 14, 2009

Related U.S. Application Data

(60) Provisional application No. 60/999,115, filed on Oct. 16, 2007.

(51) Int. Cl.
*C07D 339/02* (2006.01)
(52) U.S. Cl. .......................................................... 549/32
(58) Field of Classification Search ....................... 549/32
See application file for complete search history.

(56) References Cited

U.S. PATENT DOCUMENTS

2005/0176769 A1* 8/2005 Hawkins et al. ............... 514/323

OTHER PUBLICATIONS

Kuramochi K, Watanabe H and Kitahara T, Synthetic Study on Oximidines: A Concise Synthesis of (Z)-Enamides, *Synlett*, 2000, 397-399.
McKenna CE, Higa MT, Cheung NH and McKenna M-C, The Facile Dealylation of Phosphonic Acid Dialkyl Esters by Bromotrimethylsilane, *Tetrahedron Letters*, 1977, 2, 155-158.
*Protective Groups in Organic Chemistry*, ed. J.F.W. McOmie, Plenum Press, 1973.
T.W. Greene & P.G.M. Wuts, *Protective Groups in Organic Synthesis*, 3rd Edition, John Wiley & Sons, 1999.
International Search Report—PCT/US08/11802, Dated Dec. 6, 2008.
EP Search Report —Application No. 08840183.1-2117/2211867, PCT/US2008011802, Dated Oct. 21, 2011.
Greco, et al., "Discovery of Potent, selection, orally active nonpeptide inhibitors of human mast cell Chymase" Journal of Medicinal Chemistry, American Chemical society, US, 2007, pp. 1727-1730, vol. 50, No. 8.

* cited by examiner

*Primary Examiner* — Rei-tsang Shiao
(74) *Attorney, Agent, or Firm* — Yuriy P. Stercho

(57) ABSTRACT

The present invention is directed to an improved process for synthesizing phosphonic and phosphinic acid chymase inhibitor compounds.

15 Claims, No Drawings

US 8,222,431 B2

PROCESS FOR SYNTHESIZING PHOSPHONIC AND PHOSPHINIC ACID COMPOUNDS

This nonprovisional application claims the benefit of priority from provisional application U.S. Ser. No. 60/999,115, filed on Oct. 16, 2007.

FIELD OF THE INVENTION

The present invention is directed to an improved process for synthesizing phosphonic and phosphinic acid compounds. More particularly, the process is amenable to an efficient, large scale synthesis, produces a salt form of a compound by direct crystallization and minimizes the formation of impurities.

SUMMARY OF THE INVENTION

The present invention is directed to a process for preparing a compound of Formula (I):

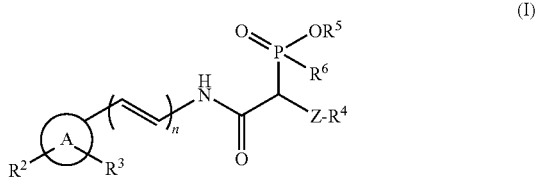

wherein $R_2$, $R_3$, $R_4$, $R_5$, $R_6$, Z, n and Ring A are as defined herein.

The present invention provides a process that is amenable to an efficient, large scale synthesis, obtains a salt form of the compound of Formula (I) by direct crystallization and avoids the formation of impurities, thus resulting in an improved yield.

The compound of Formula (I) has been disclosed in commonly assigned United States Patent Publication 2005/0176769 and referred to therein as a compound of Formula (Ia), which Publication is incorporated herein by reference in its entirety and for all purposes.

The present invention is also directed to a process for preparing a compound of Formula (Ia) and intermediates thereof:

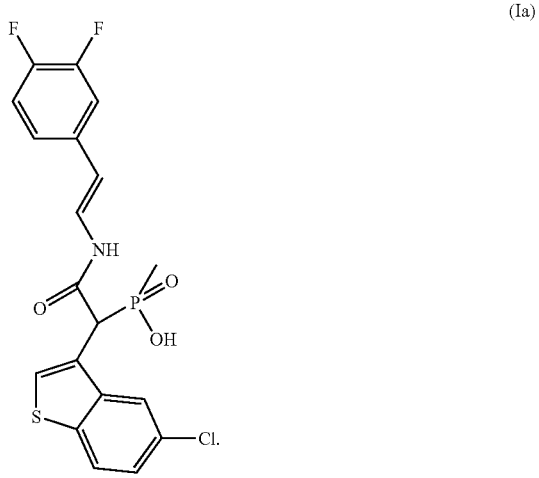

The compound of Formula (Ia), (E)-{(5-chloro-benzo[b]thiophen-3-yl)-[2-(3,4-difluoro-phenyl)-vinylcarbamoyl]-methyl}-methyl-phosphinic acid, has also been disclosed in U.S. Patent Publication 2005/0176769 and referred to therein as Compound 17 and synthesized as in Example 6 of same.

DETAILED DESCRIPTION OF THE INVENTION

The present invention is directed to a process for preparing a compound of Formula (I) and a salt thereof:

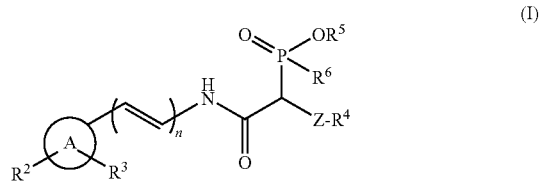

wherein

is independently selected from the group consisting of aryl, heteroaryl, and benzo fused heterocyclyl, optionally substituted with $R^2$ and $R^3$;

$R^2$ is one to three substituents independently selected from the group consisting of $C_{1-4}$alkyl, methoxy, $C_{2-6}$alkoxy, —OCH$_2$—C$_{2-6}$alkenyl, NH$_2$, —NH(C$_{1-6}$alkyl), —N(C$_{1-6}$)dialkyl, aryl, heteroaryl, halogen, hydroxy, and nitro, wherein said $C_{1-4}$alkyl, $C_{2-6}$alkenyl and $C_{2-6}$alkoxy substituents of $R^2$ are optionally substituted with a substituent independently selected from the group consisting of —NR$^{11}$R$^{12}$, aryl, heteroaryl, one to three halogens and hydroxy;

$R^{11}$ and $R^{12}$ are substituents independently selected from the group consisting of hydrogen, $C_{1-6}$alkyl, and aryl; wherein said $C_{1-6}$alkyl substituent of $R^{11}$ or $R^{12}$ is optionally substituted with a substituent selected from the group consisting of hydroxy, aryl, —C(=O)C$_{1-4}$ alkoxy, and —NR$^{15}$R$^{16}$;

$R^{15}$ and $R^{16}$ are substituents independently selected from the group consisting of hydrogen, $C_{1-6}$alkyl, and aryl, and said $R^{15}$ and $R^{16}$ are optionally taken together with the atoms to which they are attached to form a ring of five to seven members;

$R^3$ is one to three substituents independently selected from the group consisting of $C_{1-6}$alkyl, $C_{2-6}$alkenyl, $C_{1-6}$alkoxy, —OCH$_2$(C$_{2-6}$ alkenyl, NH$_2$, —NH(C$_{1-6}$ alkyl), —N(C$_{1-6}$)dialkyl, —NHC(=O)Cy, —N(C$_{1-6}$ alkyl)C(=O)Cy, —C(=O)C$_{1-4}$alkoxy, —C(=O)NR$^{17}$R$^{18}$, —C(=O)NHcycloalkyl, —C(=O)N(C$_{1-6}$ alkyl)cycloalkyl, —C(=O)NHCy, —C(=O)N(C$_{1-6}$ alkyl)Cy, —C(=O)Cy, —OC(=O)NR$^{19}$R$^{20}$, halogen, hydroxy, nitro, cyano, aryl and aryloxy, wherein said $C_{1-6}$alkyl and $C_{1-6}$alkoxy are optionally substituted with one to three substituents independently selected from the group consisting of —NR$^{21}$R$^{22}$, —NHcycloalkyl, —N(C$_{1-6}$alkyl)cycloalkyl, —NHCy, —N(C$_{1-6}$alkyl)Cy, —NHC(O)—C$_{1-6}$alkyl-C$_{1-6}$alkoxy, aryl, heteroaryl, halogen, —C(=O)NR$^{23}$R$^{24}$, —OC(=O)NR$^{25}$R$^{26}$, —C(=O)(C$_{1-4}$)alkoxy, and —C(=O)Cy, wherein each instance of said C$_{2-6}$alkenyl is optionally substituted on a terminal carbon with aryl or —C(=O)NR$^{27}$R$^{28}$, and wherein said aryl and cycloalkyl are optionally substituted with one to three substituents independently selected from R$^{14}$;

R$^{14}$ is independently hydrogen, C$_{1-6}$alkyl, C$_{1-6}$alkoxy, C$_{2-6}$alkenyl, C$_{1-6}$alkylthio, —NH$_2$, —NH(C$_{1-6}$)alkyl, —N(C$_{1-6}$)dialkyl, aryl, heteroaryl, aryloxy, heteroaryloxy, halogen, hydroxy, or nitro, and any one of the foregoing C$_{1-6}$alkyl- or C$_{1-6}$alkoxy-containing substituents of R$^{14}$ is optionally substituted on a terminal carbon atom with a substituent selected from —NR$^{29}$R$^{30}$, aryl, heteroaryl, one to three halogen atoms, or hydroxy;

R$^{17}$, R$^{18}$, R$^{19}$, R$^{20}$, R$^{21}$, R$^{22}$, R$^{23}$, R$^{24}$, R$^{25}$ and R$^{26}$ are substituents independently selected from the group consisting of hydrogen, C$_{1-6}$alkyl and aryl, wherein C$_{1-6}$alkyl and aryl are each optionally substituted with hydroxy, aryl, aryloxy, —C(=O)-aryl, —C(=O)C$_{1-4}$alkoxy, NH$_2$, —NH(C$_{1-6}$alkyl), or —N(C$_{1-6}$)dialkyl; and said R$^{17}$ and R$^{18}$, R$^{9}$ and R$^{20}$, R$^{21}$ and R$^{22}$R$^{23}$ and R$^{24}$ or R$^{25}$ and R$^{26}$ are optionally taken together with the atoms to which they are attached to form a ring of five to seven members;

R$^{27}$ and R$^{28}$ are independently hydrogen; C$_{1-6}$alkyl optionally substituted with hydroxy, aryl, —C(=O)C$_{1-4}$alkoxy, NH$_2$, —NH(C$_{1-6}$alkyl) or —N(C$_{1-6}$)dialkyl; or aryl; and said R$^{27}$ and R$^{28}$ are optionally taken together with the atoms to which they are attached to form a ring of five to seven members;

R$^{29}$ and R$^{30}$ are independently hydrogen; C$_{1-6}$alkyl optionally substituted with hydroxy, aryl, —C(=O)C$_{1-4}$alkoxy, NH$_2$, —NH(C$_{1-6}$alkyl), or —N(C$_{1-6}$)dialkyl; or aryl; and R$^{29}$ and R$^{30}$ are optionally taken together with the atoms to which they are attached to form a ring of five to seven members;

Cy is a heterocyclyl optionally substituted with a substituent selected from the group consisting of oxo, C$_{1-6}$alkyl, —C$_{1-6}$alkylC(=O)C$_{1-6}$alkyl, —C$_{1-6}$alkylC(=O)C$_{1-6}$alkoxy, —C$_{1-6}$alkyl-aryl, —C$_{1-6}$alkylC(=O)aryl, —C(=O)(C$_{1-6}$)alkyl, —C(=O)(C$_{1-6}$)alkoxy, —C(=O)aryl, —SO$_2$aryl, aryl, heteroaryl and heterocyclyl, wherein aryl and the aryl portion of —C$_{1-6}$alkylC(=O)aryl, —C(=O)aryl and —SO$_2$aryl are optionally substituted with one to three substituents independently selected from the group consisting of C$_{1-6}$alkyl, C$_{1-6}$alkoxy, halogen, hydroxy, NH$_2$, —NH(C$_{1-6}$alkyl) and —N(C$_{1-6}$)dialkyl; and wherein heterocyclyl is optionally substituted with aryl, one to three halogen atoms, or one to three oxo substituents; P and, wherein heterocyclyl is optionally spiro-fused to said Cy;

R$^5$ is selected from the group consisting of hydrogen or C$_{1-3}$alkyl optionally substituted with NH$_2$, —NH(C$_{1-6}$)alkyl, —N(C$_{1-6}$)dialkyl, C$_{1-6}$alkylcarbonyloxy-, C$_{1-6}$alkoxycarbonyloxy-, C$_{1-6}$alkylcarbonylthio-, (C$_{1-6}$)alkylaminocarbonyl-, di(C$_{1-6}$)alkylaminocarbonyl-, one to three halogens, or hydroxy; and said aryl is optionally substituted with C$_{1-6}$alkyl, C$_{1-6}$alkoxy, C$_{1-6}$alkylthio-, C$_{2-6}$alkenyl, NH$_2$, —NH(C$_{1-6}$)alkyl, —N(C$_{1-6}$)dialkyl, aryl, heteroaryl, aryloxy, heteroaryloxy, halogen, hydroxy, or nitro; alternatively, when R$^6$ is C$_{1-8}$alkoxy, said R$^5$ and R$^6$ are taken together with the atoms to which they are attached to form a 5-8 membered monocyclic ring, provided that R$^5$ is other than C$_{1-3}$alkyl substituted with di(C$_{1-6}$)alkylamino-carbonyl- when ring system A is 3,4-difluoro-phenyl, n is 1, R$^6$ is OH, and Z—R$^4$ is 5-chloro-benzothiophen-3-yl; and provided that R$^5$ is other than C$_{1-3}$alkyl substituted with C$_{1-6}$alkylcarbonylthio- when ring system A is 3,4-difluoro-phenyl, n is 1, R$^6$ is CH$_3$, and Z—R$^4$ is 5-chloro-benzothiophen-3-yl;

R$^6$ is selected from the group consisting of C$_{1-6}$alkyl, C$_{1-8}$alkoxy, heteroaryl, aryl, and hydroxy; wherein C$_{1-6}$alkyl is optionally substituted on a terminal carbon atom with a substituent selected from C$_{1-3}$alkoxy, aryl, or hydroxy; and C$_{1-8}$alkoxy is optionally substituted on a terminal carbon atom with a substituent independently selected from the group consisting of C$_{1-6}$alkylcarbonyloxy- and di(C$_{1-6}$)alkylaminocarbonyl-; and wherein heteroaryl and aryl are optionally substituted with one to three substituents independently selected from the group consisting of aryl, hydroxy, C$_{1-6}$alkoxy, and halogen;

Z is a bicyclic aryl or bicyclic heteroaryl; wherein aryl and heteroaryl are optionally substituted with the group R$^4$;

R$^4$ is one to three substituents selected from the group consisting of C$_{1-6}$alkyl, C$_{2-6}$alkenyl, C$_{1-6}$alkoxy, aryl (C$_{2-6}$)alkenyl, halogen, —C(=O)Cy, —C(=O)NR$^{31}$R$^{32}$, aryl, —CO$_2$H, oxo and cyano, wherein said C$_{1-6}$alkyl, C$_{2-6}$alkenyl and C$_{1-6}$alkoxy are optionally substituted with a substituent independently selected from the group consisting of —NR$^{33}$R$^{34}$, aryl, one to three halogen atoms and hydroxy, and wherein said aryl is optionally substituted with a substituent independently selected from the group consisting of hydrogen, C$_{1-6}$alkyl, C$_{1-6}$alkoxy, aryl, halogen, hydroxy, and nitro; and R$^{31}$, R$^{32}$, R$^{33}$ and R$^{34}$ are substituents independently selected from the group consisting of hydrogen, C$_{1-6}$alkyl, and aryl, wherein C$_{1-6}$alkyl is optionally substituted with hydroxy, aryl, —C(=O)C$_{1-4}$alkoxy, NH$_2$, —NH(C$_{1-6}$alkyl) or —N(C$_{1-6}$)dialkyl; and said R$^{31}$ and R$^{32}$ or R$^{33}$ and R$^{34}$ are optionally taken together with the atoms to which they are attached to form a ring of five to seven members;

according to Scheme A, comprising the steps of:

Scheme A

Step 1. reacting a Compound A1 (wherein R$^5$ is C$_{1-3}$alkyl) with a Compound A2, wherein Compound A1 and Compound A2 are present in a first ratio in toluene to provide a Compound A3 (wherein R$^5$ is C$_{1-3}$alkyl), representative of a compound of Formula (I):

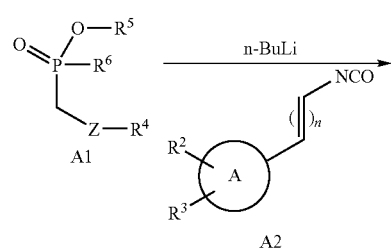

-continued

![A3 structure with R5 = C]

Step 2. reacting the Compound A3 (wherein $R^5$ is C in the presence of TMSBr in acetonitrile and optionally present pyridine, wherein TMSBr and Compound A3 are in a second ratio, and wherein TMSBr and pyridine, when pyridine is present, are in a third ratio to provide a Compound A4 (wherein $R^5$ is hydrogen), representative of a compound of Formula (I):

![A3 to A4 reaction scheme]

A3

![A4 structure]

A4 wherein in the second ratio, TMSBr and Compound A3 are in a range of about 2.5:1 TMSBr:Compound A3 to about 2:1 TMSBr:Compound A3 and wherein in the third ratio, TMSBr and pyridine, when pyridine is present, are in a range of from about 1:1 TMSBr:pyridine to about 1:2 TMSBr:pyridine; and optionally Step 3. reacting the Compound A4 (wherein $R^5$ is hydrogen) with a cationic salt-forming compound in a solvent mixture, wherein the solvents in the mixture are in a fourth ratio, to provide a Compound A5 as a salt, representative of a compound of Formula (I), wherein the salt is obtained by direct crystallization:

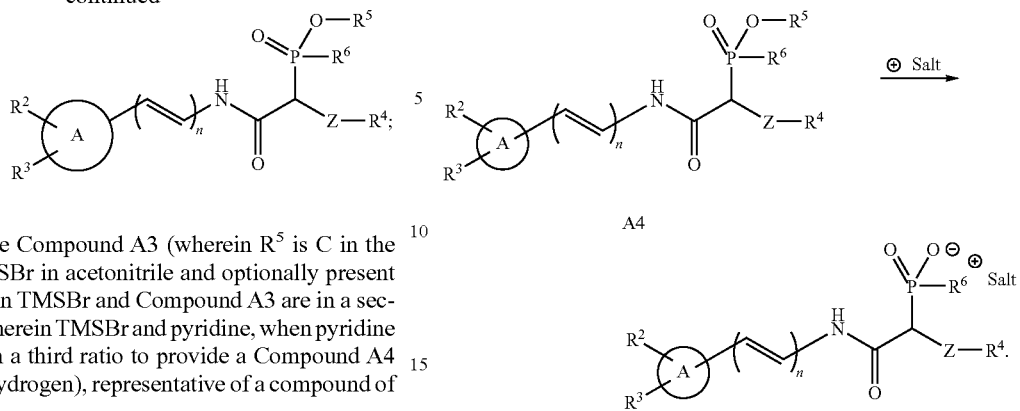

A4

A5

An example of the present invention includes a process wherein in the first ratio of Compound A1 and Compound A2, the amount of Compound A1 exceeds the amount of Compound A2 by about 0.2 equivalents.

An example of the present invention includes an amount of Compound A1 in a range of from about 1.2 equivalents to about 1 equivalent and an amount of Compound A2 in a range of from about 1 equivalent to about 0.8 equivalents according to said first ratio.

An example of the present invention includes TMSBr in a range of about 2.5:1 TMSBr:Compound A3 to about 2:1 TMSBr:Compound A3, according to said second ratio, and pyridine is present in a range of about 1:1 TMSBr:pyridine to about 1:2 TMSBr:pyridine according to said third ratio.

An example of the present invention includes a process wherein in the third ratio, TMSBr and pyridine are about 1:2 TMSBr:pyridine.

An example of the present invention includes TMSBr in a range of about 2.5:1 TMSBr:Compound A3 to about 2:1 TMSBr:Compound A3, according to said second ratio, wherein pyridine is not present.

An example of the present invention includes a process wherein the cationic salt of the compound of Formula (I) is a choline salt precipitated from a solvent mixture of MeOH and EtOAc, wherein the solvents are in said fourth ratio of about 1:3 MeOH:EtOAc.

The foregoing Scheme A and the other schemes shown herein are offered by way of illustration; the invention should not be construed as being limited by the chemical reactions and conditions expressed. The methods for preparing the various starting materials used in the schemes are within the skill of persons versed in the art.

The present invention is also directed to a process for preparing a compound of Formula (I) disclosed in commonly assigned U.S. Patent Publication 2005/0176769 selected from the group consisting of:

| Cpd | Name |
|---|---|
| 1 | [(5-chloro-1-methyl-1H-indol-3-yl)-(naphthalen-2-ylcarbamoyl)-methyl]-methyl-phosphinic acid, |
| 2 | (E)-{(5-chloro-benzo[b]thiophen-3-yl)-[2-(3,4-difluoro-phenyl)-vinylcarbamoyl]-methyl}-phosphonic acid, |
| 3 | [(5-chloro-1-methyl-1H-indol-3-yl)-(naphthalen-2-ylcarbamoyl)-methyl]-phosphonic acid, |
| 4 | (E)-{(5-chloro-1-methyl-1H-indol-3-yl)-[2-(4-fluoro-phenyl)-vinylcarbamoyl]-methyl}-phosphonic acid, |
| 5 | [(5-methyl-benzo[b]thiophen-3-yl)-(naphthalen-2-ylcarbamoyl)-methyl]-phosphonic acid, |

-continued

| Cpd | Name |
|---|---|
| 6 | (E)-{(5-chloro-1-methyl-1H-indol-3-yl)-[2-(3-fluoro-phenyl)-vinylcarbamoyl]-methyl}-methyl-phosphinic acid, |
| 7 | (E)-{(5-chloro-1-methyl-1H-indol-3-yl)-[2-(3,4-difluoro-phenyl)-vinylcarbamoyl]-methyl}-methyl-phosphinic acid, |
| 8 | [(4-{[1-(naphthalene-2-carbonyl)-piperidine-4-carbonyl]-amino}-naphthalen-2-ylcarbamoyl)-naphthalen-1-yl-methyl]-phosphonic acid, |
| 9 | [(5-chloro-benzo[b]thiophen-3-yl)-(naphthalen-2-ylcarbamoyl)-methyl]-phosphonic acid, |
| 10 | [(5-fluoro-benzo[b]thiophen-3-yl)-(naphthalen-2-ylcarbamoyl)-methyl]-phosphonic acid, |
| 11 | [(5-fluoro-1-methyl-1H-indol-3-yl)-(naphthalen-2-ylcarbamoyl)-methyl]-phosphonic acid, |
| 12 | (E)-[[2-(4-amino-phenyl)-vinylcarbamoyl]-(5-chloro-benzo[b]thiophen-3-yl)-methyl]-phosphonic acid, |
| 13 | [(5-bromo-1-methyl-1H-indol-3-yl)-(naphthalen-2-ylcarbamoyl)-methyl]-phosphonic acid, |
| 14 | (E)-[(5-chloro-benzo[b]thiophen-3-yl)-styrylcarbamoyl-methyl]-methyl-phosphinic acid, |
| 15 | (E)-{(5-chloro-benzo[b]thiophen-3-yl)-[2-(3-fluoro-phenyl)-vinylcarbamoyl]-methyl}-methyl-phosphinic acid, |
| 16 | (E)-{(5-chloro-benzo[b]thiophen-3-yl)-[2-(3,4,5-trifluoro-phenyl)-vinylcarbamoyl]-methyl}-methyl-phosphinic acid, |
| 17 | (E)-{(5-chloro-benzo[b]thiophen-3-yl)-[2-(3,4-difluoro-phenyl)-vinylcarbamoyl]-methyl}-methyl-phosphinic acid, |
| 18 | (E)-[(5-chloro-benzo[b]thiophen-3-yl)-styrylcarbamoyl-methyl]-phosphonic acid, |
| 19 | (E)-{(5-chloro-benzo[b]thiophen-3-yl)-[2-(4-fluoro-phenyl)-vinylcarbamoyl]-methyl}-phosphonic acid, |
| 20 | [(5-chloro-benzo[b]thiophen-3-yl)-(naphthalen-2-ylcarbamoyl)-methyl]-methyl-phosphinic acid, |
| 21 | (E)-{(5-chloro-benzo[b]thiophen-3-yl)-[2-(2-fluoro-phenyl)-vinylcarbamoyl]-methyl}-methyl-phosphinic acid, |
| 22 | [(1-methyl-1H-indol-3-yl)-(naphthalen-2-ylcarbamoyl)-methyl]-phosphonic acid, |
| 23 | [(5-bromo-benzo[b]thiophen-3-yl)-(naphthalen-2-ylcarbamoyl)-methyl]-phosphonic acid, |
| 24 | (E)-{(5-chloro-benzo[b]thiophen-3-yl)-[2-(4-fluoro-phenyl)-vinylcarbamoyl]-methyl}-methyl-phosphinic acid, |
| 25 | (E)-[(5-chloro-benzo[b]thiophen-3-yl)-(2-pyridin-3-yl-vinylcarbamoyl)-methyl]-phosphonic acid, |
| 26 | [benzo[b]thiophen-3-yl-(naphthalen-2-ylcarbamoyl)-methyl]-phosphonic acid, |
| 27 | {(naphthalen-2-ylcarbamoyl)-[1-(3-phenyl-allyl)-1H-indol-3-yl]-methy}-phosphonic acid, |
| 28 | [(5-chloro-benzo[b]thiophen-3-yl)-(naphthalen-2-ylcarbamoyl)-methyl]-ethyl-phosphinic acid, |
| 29 | (E)-{(5-chloro-benzo[b]thiophen-3-yl)-[2-(3,4-difluoro-phenyl)-vinylcarbamoyl]-methyl}-ethyl-phosphinic acid, |
| 30 | [(benzothiazol-6-ylcarbamoyl)-(5-chloro-benzo[b]thiophen-3-yl)-methyl]-phosphonic acid, |
| 31 | [naphthalen-1-yl-(naphthalen-2-ylcarbamoyl)-methyl]-phosphonic acid, |
| 32 | methyl-{(naphthalen-2-ylcarbamoyl)-[2-(4-phenyl-piperidine-1-carbonyl)-benzo[b]thiophen-3-yl]-methyl}-phosphinic acid, |
| 33 | methyl-[naphthalen-1-yl-(naphthalen-2-ylcarbamoyl)-methyl]-phosphinic acid, |
| 34 | [(5-chloro-benzo[b]thiophen-3-yl)-(naphthalen-2-ylcarbamoyl)-methyl]-(3-methoxy-propyl)-phosphinic acid, |
| 35 | [{2-[4-(4-methoxy-phenyl)-piperidine-1-carbonyl]-benzo[b]thiophen-3-yl}-(naphthalen-2-ylcarbamoyl)-methyl]-methyl-phosphinic acid, |
| 36 | [(5-chloro-benzo[b]thiophen-3-yl)-(naphthalen-2-ylcarbamoyl)-methyl]-phenethyl-phosphinic acid, |
| 37 | (E)-(naphthalen-1-yl-styrylcarbamoyl-methyl)-phosphonic acid, |
| 38 | (E)-{(5-chloro-benzo[b]thiophen-3-yl)-[2-(4-methoxy-phenyl)-vinylcarbamoyl]-methyl}-phosphonic acid, |
| 39 | (3-benzo[1,3]dioxol-5-yl-propyl)-[(5-chloro-benzo[b]thiophen-3-yl)-(naphthalen-2-ylcarbamoyl)-methyl]-phosphinic acid, |
| 40 | [(5-chloro-benzo[b]thiophen-3-yl)-(naphthalen-2-ylcarbamoyl)-methyl]-(3-naphthalen-1-yl-propyl)-phosphinic acid, |
| 41 | [{2-[4-(benzyloxycarbonyl)-piperazin-1-ylcarbonyl]-benzothiophen-3-yl}-(naphthalen-2-ylcarbamoyl)-methyl]-methyl-phosphinic acid, |
| 42 | (E)-[(5-chloro-benzo[b]thiophen-3-yl)-(2-p-tolyl-vinylcarbamoyl)-methyl]-phosphonic acid, |
| 43 | [(5-chloro-benzo[b]thiophen-3-yl)-(naphthalen-2-ylcarbamoyl)-methyl]-[3-(4-hydroxy-phenyl)-propyl]-phosphinic acid, |
| 44 | ({3-[(1-benzoyl-piperidin-4-ylamino)-methyl]-naphthalen-2-ylcarbamoyl}-naphthalen-1-yl-methyl)-phosphonic acid, |
| 45 | [(5-chloro-benzo[b]thiophen-3-yl)-(naphthalen-2-ylthiocarbamoyl)-methyl]-phosphonic acid, |

| Cpd | Name |
|---|---|
| 46 | ({3-[methyl-(4-phenyl-cyclohex-3-enyl)-carbamoyl]-naphthalen-2-ylcarbamoyl}-naphthalen-1-yl-methyl)-phosphonic acid, |
| 47 | [{2-[4-(4-fluoro-phenyl)-piperidine-1-carbonyl]-benzo[b]thiophen-3-yl}-(naphthalen-2-ylcarbamoyl)-methyl]-methyl-phosphinic acid, |
| 48 | [(5-chloro-benzo[b]thiophen-3-yl)-(naphthalen-2-ylcarbamoyl)-methyl]-(3-phenyl-propyl)-phosphinic acid, |
| 49 | (E)-{(5-chloro-benzo[b]thiophen-3-yl)-[2-(3,4-dimethoxy-phenyl)-vinylcarbamoyl]-methyl}-phosphonic acid, |
| 50 | [(5-chloro-benzo[b]thiophen-3-yl)-(naphthalen-2-ylcarbamoyl)-methyl]-(4-phenyl-butyl)-phosphinic acid, |
| 51 | [(6-chloro-1-methyl-1H-indol-3-yl)-(naphthalen-2-ylcarbamoyl)-methyl]-phosphonic acid, |
| 52 | [(5-chloro-benzo[b]thiophen-3-yl)-(naphthalen-2-ylcarbamoyl)-methyl]-[3-(4-methoxy-phenyl)-propyl]-phosphinic acid, |
| 53 | {naphthalen-1-yl-[3-(3-phenethyl-pyrrolidine-1-carbonyl)-naphthalen-2-ylcarbamoyl]-methyl}-phosphonic acid, |
| 54 | [(benzo[b]thiophen-5-ylcarbamoyl)-(5-chloro-benzo[b]thiophen-3-yl)-methyl]-phosphonic acid, |
| 55 | [(5-carboxy-1-methyl-1H-indol-3-yl)-(naphthalen-2-ylcarbamoyl)-methyl]-phosphonic acid, |
| 56 | [naphthalen-1-yl-(quinolin-3-ylcarbamoyl)-methyl]-phosphonic acid, |
| 57 | [(7-chloro-1-methyl-1H-indol-3-yl)-(naphthalen-2-ylcarbamoyl)-methyl]-phosphonic acid, |
| 58 | [(benzo[b]thiophen-6-ylcarbamoyl)-naphthalen-1-yl-methyl]-phosphonic acid, |
| 59 | ({3-[4-(6-chloro-2-oxo-2,3-dihydro-benzoimidazol-1-yl)-piperidine-1-carbonyl]-naphthalen-2-ylcarbamoyl}-naphthalen-1-yl-methyl)-phosphonic acid, |
| 60 | [(biphenyl-4-ylcarbamoyl)-naphthalen-1-yl-methyl]-phosphonic acid, |
| 61 | [(1-cyclopropylmethyl-1H-indol-3-yl)-(naphthalen-2-ylcarbamoyl)-methyl]-phosphonic acid, |
| 62 | [(4-chloro-1-methyl-1H-indol-3-yl)-(naphthalen-2-ylcarbamoyl)-methyl]-phosphonic acid, |
| 63 | [(benzo[b]thiophen-2-ylcarbamoyl)-naphthalen-1-yl-methyl]-phosphonic acid, |
| 64 | [(5-cyano-1-methyl-1H-indol-3-yl)-(naphthalen-2-ylcarbamoyl)-methyl]-phosphonic acid, |
| 65 | (E)-{(5-chloro-benzo[b]thiophen-3-yl)-[2-(4-hydroxy-phenyl)-vinylcarbamoyl]-methyl}-phosphonic acid, |
| 66 | [(6-bromo-naphthalen-2-ylcarbamoyl)-(5-chloro-benzo[b]thiophen-3-yl)-methyl]-phosphonic acid, |
| 67 | [(1H-indol-3-yl)-(naphthalen-2-ylcarbamoyl)-methyl]-phosphonic acid, |
| 68 | [(2-amino-benzothiazol-6-ylcarbamoyl)-(5-chloro-benzo[b]thiophen-3-yl)-methyl]-phosphonic acid, |
| 69 | [(3-cyclohexylaminomethyl-naphthalen-2-ylcarbamoyl)-naphthalen-1-yl-methyl]-phosphonic acid, |
| 70 | [(5-phenyl-benzo[b]thiophen-3-yl)-(naphthalen-2-ylcarbamoyl)-methyl]-phosphonic acid, |
| 71 | [(3-benzylcarbamoyloxymethyl-naphthalen-2-ylcarbamoyl)-naphthalen-1-yl-methyl]-phosphonic acid, |
| 72 | {naphthalen-1-yl-[3-(3-pyridin-4-yl-pyrrolidine-1-carbonyl)-naphthalen-2-ylcarbamoyl]-methyl}-phosphonic acid, |
| 73 | [(5-methoxy-1-methyl-1H-indol-3-yl)-(naphthalen-2-ylcarbamoyl)-methyl]-phosphonic acid, |
| 74 | 3-(2-naphthalen-1-yl-2-phosphono-acetylamino)-naphthalene-2-carboxylic acid methyl ester, |
| 75 | [(6-bromo-benzo[b]thiophen-3-yl)-(naphthalen-2-ylcarbamoyl)-methyl]-phosphonic acid, |
| 76 | [(1-isopropyl-1H-indol-3-yl)-(naphthalen-2-ylcarbamoyl)-methyl]-phosphonic acid, |
| 77 | (E)-{(5-chloro-benzo[b]thiophen-3-yl)-[2-(4-chloro-phenyl)-vinylcarbamoyl]-methyl}-methyl-phosphinic acid, |
| 78 | [naphthalen-1-yl-(quinolin-6-ylcarbamoyl)-methyl]-phosphonic acid, |
| 79 | (E)-{(5-chloro-benzo[b]thiophen-3-yl)-[2-(4-trifluoromethyl-phenyl)-vinylcarbamoyl]-methyl}-phosphonic acid, |
| 80 | [(naphthalen-2-ylcarbamoyl)-(1-phenyl-1H-indol-3-yl)-methyl]-phosphonic acid, |
| 81 | ({3-[4-(1H-indol-3-yl)-piperidine-1-carbonyl]-naphthalen-2-ylcarbamoyl}-naphthalen-1-yl-methyl)-phosphonic acid, |
| 82 | [(indan-5-ylcarbamoyl)-naphthalen-1-yl-methyl]-phosphonic acid, |
| 83 | [(5-chloro-1,1-dioxo-1H-benzo[b]thiophen-3-yl)-(naphthalen-2-ylcarbamoyl)-methyl]-phosphonic acid, |
| 84 | {naphthalen-1-yl-[3-(3-phenyl-pyrrolidine-1-carbonyl)-naphthalen-2-ylcarbamoyl]-methyl}-phosphonic acid, |
| 85 | [(5-chloro-benzo[b]thiophen-3-yl)-(naphthalen-2-ylcarbamoyl)-methyl]-phenyl-phosphinic acid, |
| 86 | ({3-[(3-methyl-cyclohexylamino)-methyl]-naphthalen-2-ylcarbamoyl}-naphthalen-1-yl-methyl)-phosphonic acid, |
| 87 | {[3-(cyclopentyl-methyl-carbamoyl)-naphthalen-2-ylcarbamoyl]-naphthalen-1-yl-methyl}-phosphonic acid, |

-continued

| Cpd | Name |
|---|---|
| 88 | ({3-[(5-methoxycarbonyl)-pent-1-ylaminomethyl]-naphthalen-2-ylcarbamoyl}-naphthalen-1-yl-methyl)-phosphonic acid, |
| 89 | (naphthalen-1-yl-{3-[4-(2-oxo-2,3-dihydro-benzoimidazol-1-yl)-piperidine-1-carbonyl]-naphthalen-2-ylcarbamoyl}-methyl)-phosphonic acid, |
| 90 | [naphthalen-1-yl-(3-phenylcarbamoyloxymethyl-naphthalen-2-ylcarbamoyl)-methyl]-phosphonic acid, |
| 91 | [naphthalen-1-yl-(3-phenylcarbamoyloxy-naphthalen-2-yl-carbamoyl)-methyl]-phosphonic acid, |
| 92 | [naphthalen-1-yl-(quinolin-2-ylcarbamoyl)-methyl]-phosphonic acid, |
| 93 | {naphthalen-1-yl-[3-(4-phenoxy-phenylcarbamoyloxymethyl)-naphthalen-2-ylcarbamoyl]-methyl}-phosphonic acid, |
| 94 | [[5-(4-fluoro-phenyl)-1-methyl-1H-indol-3-yl]-(naphthalen-2-ylcarbamoyl)-methyl]-phosphonic acid, |
| 95 | [(4-bromo-benzo[b]thiophen-3-yl)-(naphthalen-2-ylcarbamoyl)-methyl]-phosphonic acid, |
| 96 | {[3-(4-benzotriazol-1-yl-piperidine-1-carbonyl)-naphthalen-2-ylcarbamoyl]-naphthalen-1-yl-methyl}-phosphonic acid, |
| 97 | {naphthalen-1-yl-[3-(4-phenyl-piperidine-1-carbonyl)-naphthalen-2-ylcarbamoyl]-methyl}-phosphonic acid, |
| 98 | {[3-({methyl-[1-(naphthalene-2-carbonyl)-piperidin-4-yl]-amino}-methyl)-naphthalen-2-ylcarbamoyl]-naphthalen-1-yl-methyl}-phosphonic acid, |
| 99 | {[3-(3-benzenesulfonyl-pyrrolidine-1-carbonyl)-naphthalen-2-ylcarbamoyl]-naphthalen-1-yl-methyl}-phosphonic acid, |
| 100 | {naphthalen-1-yl-[3-(4-oxo-1-phenyl-1,3,8-triaza-spiro[4.5]decane-8-carbonyl)-naphthalen-2-ylcarbamoyl]-methyl}-phosphonic acid, |
| 101 | {naphthalen-1-yl-[3-(naphthalen-2-ylcarbamoyloxymethyl)-naphthalen-2-ylcarbamoyl]-methyl}-phosphonic acid, |
| 102 | [(9H-fluoren-3-ylcarbamoyl)-naphthalen-1-yl-methyl]-phosphonic acid, |
| 103 | {[3-(benzylamino-methyl)-naphthalen-2-ylcarbamoyl]-naphthalen-1-yl-methyl}-phosphonic acid, |
| 104 | [(3-hydroxy-naphthalen-2-ylcarbamoyl)-naphthalen-1-yl-methyl]-phosphonic acid, |
| 105 | {[3-(2-benzylcarbamoyl-vinyl)-naphthalen-2-ylcarbamoyl]-naphthalen-1-yl-methyl}-phosphonic acid, |
| 106 | {naphthalen-1-yl-[3-(5-phenyl-pentylamino)-naphthalen-2-ylcarbamoyl]-methyl}-phosphonic acid, |
| 107 | {[3-(benzyl-methyl-carbamoyl)-naphthalen-2-ylcarbamoyl]-naphthalen-1-yl-methyl}-phosphonic acid, |
| 108 | {[3-({[3-(5H-dibenzo[a,d]cyclohepten-5-yl)-propyl]-methyl-amino}-methyl)-naphthalen-2-ylcarbamoyl]-naphthalen-1-yl-methyl}-phosphonic acid, |
| 109 | {[3-(4-benzothiazol-2-yl-piperidine-1-carbonyl)-naphthalen-2-ylcarbamoyl]-naphthalen-1-yl-methyl}-phosphonic acid, |
| 110 | (naphthalen-1-yl-{1-[2-oxo-2-(4-phenyl-piperidin-1-yl)-ethoxy]-naphthalen-2-ylcarbamoyl}-methyl)-phosphonic acid, |
| 111 | [(3-{[2-(3,4-dimethoxy-phenyl)-ethyl]-methyl-carbamoyl}-naphthalen-2-ylcarbamoyl)-naphthalen-1-yl-methyl]-phosphonic acid, |
| 112 | [(1-methyl-1H-pyrrolo[2,3-b]pyridin-3-yl)-(naphthalen-2-ylcarbamoyl)-methyl]-phosphonic acid, |
| 113 | ({3-[(4-hydroxy-cyclohexylamino)-methyl]-naphthalen-2-ylcarbamoyl}-naphthalen-1-yl-methyl)-phosphonic acid, |
| 114 | [(2-carboxy-benzo[b]thiophen-3-yl)-(naphthalen-2-ylcarbamoyl)-methyl]-methyl-phosphinic acid, |
| 115 | [(3-benzylcarbamoyl-naphthalen-2-ylcarbamoyl)-naphthalen-1-yl-methyl]-phosphonic acid, |
| 116 | {naphthalen-1-yl-[3-(3-phenyl-allyloxy)-naphthalen-2-ylcarbamoyl]-methyl}-phosphonic acid, |
| 117 | [(3-benzyloxy-naphthalen-2-ylcarbamoyl)-naphthalen-1-yl-methyl]-phosphonic acid, |
| 118 | [(3-methoxycarbonylmethoxy-naphthalen-2-ylcarbamoyl)-naphthalen-1-yl-methyl]-phosphonic acid, |
| 119 | [(3-cyclopentylaminomethyl-naphthalen-2-ylcarbamoyl)-naphthalen-1-yl-methyl]-phosphonic acid, |
| 120 | [1-(5-chloro-benzo[b]thiophen-3-yl)-1-(naphthalen-2-ylcarbamoyl)-ethyl]-phosphonic acid, |
| 121 | ({3-[(methyl-phenethyl-amino)-methyl]-naphthalen-2-ylcarbamoyl}-naphthalen-1-yl-methyl)-phosphonic acid, |
| 122 | [(2-benzylcarbamoyl-benzo[b]thiophen-3-yl)-(naphthalen-2-ylcarbamoyl)-methyl]-methyl-phosphinic acid, |
| 123 | [(naphthalen-2-ylcarbamoyl)-(1-phenyl-1H-indol-3-yl)-methyl]-phosphonic acid, |
| 124 | [(1H-indol-5-ylcarbamoyl)-naphthalen-1-yl-methyl]-phosphonic acid; |
| 125 | (naphthalen-1-yl-{1-[(3-phenyl-propylcarbamoyl)-methoxy]-naphthalen-2-ylcarbamoyl}-methyl)-phosphonic acid, |
| 126 | {naphthalen-1-yl-[3-(2-phenyl-pyrrolidine-1-carbonyl)-naphthalen-2-ylcarbamoyl]-methyl}-phosphonic acid, |
| 127 | [(3-amino-naphthalen-2-ylcarbamoyl)-naphthalen-1-yl-methyl]-phosphonic acid, |

| Cpd | Name |
|---|---|
| 128 | ({3-[(5-hydroxy-pentylamino)-methyl]-naphthalen-2-ylcarbamoyl}-naphthalen-1-yl-methyl)-phosphonic acid, |
| 129 | {[(1-methoxycarbonylmethoxy-naphthalen-2-yl)carbamoyl]-naphthalen-1-yl-methyl}-phosphonic acid, |
| 130 | [(benzo[1,3]dioxol-5-ylcarbamoyl)-naphthalen-1-yl-methyl]-phosphonic acid, |
| 131 | [(isoquinolin-3-ylcarbamoyl)-naphthalen-1-yl-methyl]-phosphonic acid, |
| 132 | [naphthalen-1-yl-(3-phenoxy-phenylcarbamoyl)-methyl]-phosphonic acid, |
| 133 | {[(3-isopropyloxycarbonyl-naphthalen-2-yl)carbamoyl]-naphthalen-1-yl-methyl}-phosphonic acid, |
| 134 | [(benzo[b]thiophen-2-yl)-(naphthalen-2-ylcarbamoyl)-methyl]-phosphonic acid, |
| 135 | [(3-{[1-(naphthalene-2-carbonyl)-piperidine-4-carbonyl]-amino}-naphthalen-2-ylcarbamoyl)-naphthalen-1-yl-methyl]-phosphonic acid, |
| 136 | ({3-[(benzyl-methyl-amino)-methyl]-naphthalen-2-ylcarbamoyl}-naphthalen-1-yl-methyl)-phosphonic acid, |
| 137 | {(naphthalen-2-ylcarbamoyl)-[6-(4-pentyl-phenyl)-benzo[b]thiophen-3-yl]-methyl}-phosphonic acid, |
| 138 | [(5-chloro-benzo[b]thiophen-3-yl)-(2-phenyl-trans-cyclopropylcarbamoyl)-methyl]-methyl-phosphinic acid, |
| 139 | (E)-{(5-chloro-benzo[b]thiophen-3-yl)-[2-(2-methoxy-phenyl)-vinylcarbamoyl]-methyl}-methyl-phosphinic acid, |
| 140 | [(benzofuran-2-ylcarbamoyl)-(5-chloro-benzo[b]thiophen-3-yl)-methyl]-methyl-phosphinic acid, |
| 141 | (E)-{(5-chloro-benzo[b]thiophen-3-yl)-[2-(2-nitro-phenyl)-vinylcarbamoyl]-methyl}-methyl-phosphinic acid, |
| 142 | (E)-{(5-chloro-benzo[b]thiophen-3-yl)-[2-(2-methylcarbonyloxy-phenyl)-vinylcarbamoyl]-methyl}-methyl-phosphinic acid, |
| 143 | (E)-{(5-chloro-benzo[b]thiophen-3-yl)-[2-(2-hydroxy-phenyl)-vinylcarbamoyl]-methyl}-methyl-phosphinic acid, |
| 144 | (E)-[(5-chloro-benzo[b]thiophen-3-yl)-(2-pyridin-2-yl-vinylcarbamoyl)-methyl]-methyl-phosphinic acid, |
| 145 | (E)-[[2-(2-amino-phenyl)-vinylcarbamoyl]-(5-chloro-benzo[b]thiophen-3-yl)-methyl]-methyl-phosphinic acid, |
| 146 | (E)-{(5-chloro-benzo[b]thiophen-3-yl)-[2-(3-trifluoromethyl-phenyl)-vinylcarbamoyl]-methyl}-methyl-phosphinic acid, |
| 147 | (E)-{(5-chloro-benzo[b]thiophen-3-yl)-[2-(3-trifluoromethoxy-phenyl)-vinylcarbamoyl]-methyl}-methyl-phosphinic acid, |
| 148 | (E)-{(5-chloro-benzo[b]thiophen-3-yl)-[2-(3-methoxy-phenyl)-vinylcarbamoyl]-methyl}-methyl-phosphinic acid, |
| 149 | (E)-[(5-chloro-benzo[b]thiophen-3-yl)-(2-o-tolyl-vinylcarbamoyl)-methyl]-methyl-phosphinic acid, |
| 150 | (E)-{(5-chloro-benzo[b]thiophen-3-yl)-[2-(2,6-difluoro-phenyl)-vinylcarbamoyl]-methyl}-methyl-phosphinic acid, |
| 151 | (E)-{(5-chloro-benzo[b]thiophen-3-yl)-[2-(4-cyano-phenyl)-vinylcarbamoyl]-methyl}-methyl-phosphinic acid, |
| 152 | (E)-{(5-chloro-benzo[b]thiophen-3-yl)-[2-(2-ureido-phenyl)-vinylcarbamoyl]-methyl}-methyl-phosphinic acid, |
| 153 | (E)-{(5-chloro-benzo[b]thiophen-3-yl)-[2-(2-carbamoylcarbamoylamino-phenyl)-vinylcarbamoyl]-methyl}-methyl-phosphinic acid, |
| 154 | (E)-{(5-chloro-benzo[b]thiophen-3-yl)-[2-(2-chloro-phenyl)-vinylcarbamoyl]-methyl}-methyl-phosphinic acid, |
| 155 | (E)-{(5-chloro-benzo[b]thiophen-3-yl)-[2-(3-chloro-phenyl)-vinylcarbamoyl]-methyl}-methyl-phosphinic acid, |
| 156 | (E)-{(5-chloro-benzo[b]thiophen-3-yl)-[2-(3,5-difluoro-phenyl)-vinylcarbamoyl]-methyl}-methyl-phosphinic acid, |
| 157 | (E)-{(5-chloro-benzo[b]thiophen-3-yl)-[2-(2,3-difluoro-phenyl)-vinylcarbamoyl]-methyl}-methyl-phosphinic acid, |
| 158 | (E)-[[2-(2-bromo-phenyl)-vinylcarbamoyl]-(5-chloro-benzo[b]thiophen-3-yl)-methyl]-methyl-phosphinic acid, |
| 159 | (E)-{(5-chloro-benzo[b]thiophen-3-yl)-[2-(2,3-dimethoxy-phenyl)-vinylcarbamoyl]-methyl}-methyl-phosphinic acid, |
| 160 | (E)-{(5-chloro-benzo[b]thiophen-3-yl)-[2-(3-nitro-phenyl)-vinylcarbamoyl]-methyl}-methyl-phosphinic acid, |
| 161 | (E)-[[2-(3-bromo-phenyl)-vinylcarbamoyl]-(5-chloro-benzo[b]thiophen-3-yl)-methyl]-methyl-phosphinic acid, |
| 162 | (E)-{(5-chloro-benzo[b]thiophen-3-yl)-[2-(3,5-dimethoxy-phenyl)-vinylcarbamoyl]-methyl}-methyl-phosphinic acid, |
| 163 | (E)-{(5-chloro-benzo[b]thiophen-3-yl)-[2-(2,5-difluoro-phenyl)-vinylcarbamoyl]-methyl}-methyl-phosphinic acid, |
| 164 | (E)-{(5-chloro-benzo[b]thiophen-3-yl)-[2-(3,5-dichloro-phenyl)-vinylcarbamoyl]-methyl}-methyl-phosphinic acid, |
| 165 | (E)-{(5-chloro-benzo[b]thiophen-3-yl)-[2-(2,4-difluoro-phenyl)-vinylcarbamoyl]-methyl}-methyl-phosphinic acid, |
| 166 | (E)-[[2-(3-amino-phenyl)-vinylcarbamoyl]-(5-chloro-benzo[b]thiophen-3-yl)-methyl]-methyl-phosphinic acid, |
| 167 | (E)-2-(styrylcarbamoyl-naphthalen-1-yl-methyl)-5,5-dimethyl-1,3,2-dioxaphosphorinane 2-oxide, |

-continued

| Cpd | Name |
|---|---|
| 168 | (E)-(styrylcarbamoyl)-naphthalen-1-yl-methyl-phosphonic acid (3-methoxy-propyl) ester, |
| 169 | (E)-(styrylcarbamoyl)-naphthalen-1-yl-methyl-phosphonic acid bis-(3-methoxy-propyl) ester, |
| 170 | (E)-(styrylcarbamoyl)-naphthalen-1-yl-methyl-phosphonic acid mono-(2-benzo[1,3]dioxol-2-yl-ethyl) ester, |
| 171 | (E)-(styrylcarbamoyl)-naphthalen-1-yl-methyl-phosphonic acid (tert-butylcarbonyloxymethyl) ester, |
| 172 | (E)-2-(styrylcarbamoyl-naphthalen-1-yl-methyl)-1,3,2-dioxaphosphorinane 2-oxide, |
| 173 | (E)-(styrylcarbamoyl)-naphthalen-1-yl-methyl-phosphonic acid bis-(2-dimethylamino-ethyl) ester, |
| 174 | (E)-(styrylcarbamoyl)-naphthalen-1-yl-methyl-phosphonic acid bis-(diethylaminocarbonylmethyl) ester, |
| 175 | (E)-(styrylcarbamoyl)-naphthalen-1-yl-methyl-phosphonic acid bis-(2-tert-butylcarbonylthioethyl) ester, |
| 176 | (E)-{(5-chloro-benzo[b]thiophen-3-yl)-[2-(3,4-difluoro-phenyl)-vinylcarbamoyl]-methyl}-methyl-phosphinic acid (tert-butylcarbonyloxymethyl) ester, |
| 177 | (E)-{(5-chloro-benzo[b]thiophen-3-yl)-[2-(3,4-difluoro-phenyl)-vinylcarbamoyl]-methyl}-methyl-phosphinic acid (2-dimethylaminoethyl) ester, |
| 178 | (E)-{(5-chloro-benzo[b]thiophen-3-yl)-[2-(3,4-difluoro-phenyl)-vinylcarbamoyl]-methyl}-methyl-phosphinic acid (2-aminoethyl) ester, |
| 179 | (E)-{(5-chloro-benzo[b]thiophen-3-yl)-[2-(3,4-difluoro-phenyl)-vinylcarbamoyl]-methyl}-methyl-phosphinic acid (2-diethylamino-2-oxo-ethyl) ester, |
| 180 | (E)-{(5-chloro-benzo[b]thiophen-3-yl)-[2-(3,4-difluoro-phenyl)-vinylcarbamoyl]-methyl}-phosphonic acid bis-(tert-butylcarbonyloxymethyl) ester, |
| 181 | (E)-{(5-chloro-benzo[b]thiophen-3-yl)-[2-(3,4-difluoro-phenyl)-vinylcarbamoyl]-methyl}-phosphonic acid (tert-butylcarbonyloxymethyl) ester, |
| 182 | (E)-{(5-chloro-benzo[b]thiophen-3-yl)-[2-(3,4-difluoro-phenyl)-vinylcarbamoyl]-methyl}-phosphonic acid bis-(2-diethylamino-2-oxo-ethyl) ester, |
| 183 | (E)-2-{(5-chloro-benzo[b]thiophen-3-yl)-[2-(3,4-difluoro-phenyl)-vinylcarbamoyl]-methyl}-1,3,2-dioxaphosphorinane 2-oxide, |
| 184 | (E)-{(5-chloro-benzo[b]thiophen-3-yl)-[2-(3,4-difluoro-phenyl)-vinylcarbamoyl]-methyl}-phosphonic acid[(methylcarbonyloxy)-methyl] ester, |
| 185 | (E)-{(5-chloro-benzo[b]thiophen-3-yl)-[2-(3,4-difluoro-phenyl)-vinylcarbamoyl]-methyl}-phosphonic acid[(isopropoxycarbonyloxy)-methyl] ester, |
| 186 | (E)-{(5-chloro-benzo[b]thiophen-3-yl)-[2-(2-methoxy-phenyl)-vinylcarbamoyl]-methyl}-phosphonic acid, |
| 187 | (E)-[(5-chloro-benzo[b]thiophen-3-yl)-(2-pyridin-2-yl-vinylcarbamoyl)-methyl]-phosphonic acid, |
| 188 | (E)-{(5-chloro-benzo[b]thiophen-3-yl)-[2-(3-trifluoromethoxy-phenyl)-vinylcarbamoyl]-methyl}-phosphonic acid, |
| 189 | (E)-{(5-chloro-benzo[b]thiophen-3-yl)-[2-(3-methoxy-phenyl)-vinylcarbamoyl]-methyl}-phosphonic acid, |
| 190 | (E)-{(5-chloro-benzo[b]thiophen-3-yl)-[2-(2,6-difluoro-phenyl)-vinylcarbamoyl]-methyl}-phosphonic acid, |
| 191 | (E)-{(5-chloro-benzo[b]thiophen-3-yl)-[2-(2-chloro-phenyl)-vinylcarbamoyl]-methyl}-phosphonic acid, |
| 192 | (E)-{(5-chloro-benzo[b]thiophen-3-yl)-[2-(3-chloro-phenyl)-vinylcarbamoyl]-methyl}-phosphonic acid, |
| 193 | (E)-{(5-chloro-benzo[b]thiophen-3-yl)-[2-(3,5-difluoro-phenyl)-vinylcarbamoyl]-methyl}-phosphonic acid, |
| 194 | (E)-{(5-chloro-benzo[b]thiophen-3-yl)-[2-(2,3-difluoro-phenyl)-vinylcarbamoyl]-methyl}-phosphonic acid, |
| 195 | (E)-{(5-chloro-benzo[b]thiophen-3-yl)-[2-(2-bromo-phenyl)-vinylcarbamoyl]-methyl}-phosphonic acid, |
| 196 | (E)-{(5-chloro-benzo[b]thiophen-3-yl)-[2-(2,3-dimethoxy-phenyl)-vinylcarbamoyl]-methyl}-phosphonic acid, |
| 197 | (E)-{(5-chloro-benzo[b]thiophen-3-yl)-[2-(3-nitro-phenyl)-vinylcarbamoyl]-methyl}-phosphonic acid, |
| 198 | (E)-{(5-chloro-benzo[b]thiophen-3-yl)-[2-(3-bromo-phenyl)-vinylcarbamoyl]-methyl}-phosphonic acid, |
| 199 | (E)-{(5-chloro-benzo[b]thiophen-3-yl)-[2-(3,5-dimethoxy-phenyl)-vinylcarbamoyl]-methyl}-phosphonic acid, |
| 200 | (E)-{(5-chloro-benzo[b]thiophen-3-yl)-[2-(2,5-difluoro-phenyl)-vinylcarbamoyl]-methyl}-phosphonic acid, |
| 201 | (E)-{(5-chloro-benzo[b]thiophen-3-yl)-[2-(3,5-dichloro-phenyl)-vinylcarbamoyl]-methyl}-phosphonic acid, |
| 202 | (E)-{(5-chloro-benzo[b]thiophen-3-yl)-[2-(2,4-difluoro-phenyl)-vinylcarbamoyl]-methyl}-phosphonic acid, |

| Cpd | Name |
|---|---|
| 203 | (E)-{(5-chloro-benzo[b]thiophen-3-yl)-[2-(3-amino-phenyl)-vinylcarbamoyl]-methyl}-phosphonic acid, |
| 204 | (E)-{(5-chloro-benzo[b]thiophen-3-yl)-[2-(2-methoxy-phenyl)-vinylcarbamoyl]-methyl}-methyl-phosphinic acid (tert-butylcarbonyloxymethyl) ester, |
| 205 | (E)-[(5-chloro-benzo[b]thiophen-3-yl)-(2-pyridin-2-yl-vinylcarbamoyl)-methyl]-methyl-phosphinic acid (tert-butylcarbonyloxymethyl) ester, |
| 206 | (E)-{(5-chloro-benzo[b]thiophen-3-yl)-[2-(3-trifluoromethoxy-phenyl)-vinylcarbamoyl]-methyl}-methyl-phosphinic acid (tert-butylcarbonyloxymethyl) ester, |
| 207 | (E)-{(5-chloro-benzo[b]thiophen-3-yl)-[2-(3-methoxy-phenyl)-vinylcarbamoyl]-methyl}-methyl-phosphinic acid (tert-butylcarbonyloxymethyl) ester, |
| 208 | (E)-{(5-chloro-benzo[b]thiophen-3-yl)-[2-(2,6-difluoro-phenyl)-vinylcarbamoyl]-methyl}-methyl-phosphinic acid (tert-butylcarbonyloxymethyl) ester, |
| 209 | (E)-{(5-chloro-benzo[b]thiophen-3-yl)-[2-(2-chloro-phenyl)-vinylcarbamoyl]-methyl}-methyl-phosphinic acid (tert-butylcarbonyloxymethyl) ester, |
| 210 | (E)-{(5-chloro-benzo[b]thiophen-3-yl)-[2-(3-chloro-phenyl)-vinylcarbamoyl]-methyl}-methyl-phosphinic acid (tert-butylcarbonyloxymethyl) ester, |
| 211 | (E)-{(5-chloro-benzo[b]thiophen-3-yl)-[2-(3,5-difluoro-phenyl)-vinylcarbamoyl]-methyl}-methyl-phosphinic acid (tert-butylcarbonyloxymethyl) ester, |
| 212 | (E)-{(5-chloro-benzo[b]thiophen-3-yl)-[2-(2,3-difluoro-phenyl)-vinylcarbamoyl]-methyl}-methyl-phosphinic acid (tert-butylcarbonyloxymethyl) ester, |
| 213 | (E)-{(5-chloro-benzo[b]thiophen-3-yl)-[2-(2-bromo-phenyl)-vinylcarbamoyl]-methyl}-methyl-phosphinic acid (tert-butylcarbonyloxymethyl) ester, |
| 214 | (E)-{(5-chloro-benzo[b]thiophen-3-yl)-[2-(2,3-dimethoxy-phenyl)-vinylcarbamoyl]-methyl}-methyl-phosphinic acid (tert-butylcarbonyloxymethyl) ester, |
| 215 | (E)-{(5-chloro-benzo[b]thiophen-3-yl)-[2-(3-nitro-phenyl)-vinylcarbamoyl]-methyl}-methyl-phosphinic acid (tert-butylcarbonyloxymethyl) ester, |
| 216 | (E)-{(5-chloro-benzo[b]thiophen-3-yl)-[2-(3-bromo-phenyl)-vinylcarbamoyl]-methyl}-methyl-phosphinic acid (tert-butylcarbonyloxymethyl) ester, |
| 217 | (E)-{(5-chloro-benzo[b]thiophen-3-yl)-[2-(3,5-dimethoxy-phenyl)-vinylcarbamoyl]-methyl}-methyl-phosphinic acid (tert-butylcarbonyloxymethyl) ester, |
| 218 | (E)-{(5-chloro-benzo[b]thiophen-3-yl)-[2-(2,5-difluoro-phenyl)-vinylcarbamoyl]-methyl}-methyl-phosphinic acid (tert-butylcarbonyloxymethyl) ester, |
| 219 | (E)-{(5-chloro-benzo[b]thiophen-3-yl)-[2-(3,5-dichloro-phenyl)-vinylcarbamoyl]-methyl}-methyl-phosphinic acid (tert-butylcarbonyloxymethyl) ester, |
| 220 | (E)-{(5-chloro-benzo[b]thiophen-3-yl)-[2-(2,4-difluoro-phenyl)-vinylcarbamoyl]-methyl}-methyl-phosphinic acid (tert-butylcarbonyloxymethyl) ester, |
| 221 | (E)-{(5-chloro-benzo[b]thiophen-3-yl)-[2-(3-amino-phenyl)-vinylcarbamoyl]-methyl}-methyl-phosphinic acid (tert-butylcarbonyloxymethyl) ester, |
| 222 | (E)-{(5-chloro-benzo[b]thiophen-3-yl)-[2-(2-methoxy-phenyl)-vinylcarbamoyl]-methyl}-phosphonic acid bis-(tert-butylcarbonyloxymethyl) ester, |
| 223 | (E)-[(5-chloro-benzo[b]thiophen-3-yl)-(2-pyridin-2-yl-vinylcarbamoyl)-methyl]-phosphonic acid bis-(tert-butylcarbonyloxymethyl) ester, |
| 224 | (E)-{(5-chloro-benzo[b]thiophen-3-yl)-[2-(3-trifluoromethoxy-phenyl)-vinylcarbamoyl]-methyl}-phosphonic acid bis-(tert-butylcarbonyloxymethyl) ester, |
| 225 | (E)-{(5-chloro-benzo[b]thiophen-3-yl)-[2-(3-methoxy-phenyl)-vinylcarbamoyl]-methyl}-phosphonic acid bis-(tert-butylcarbonyloxymethyl) ester, |
| 226 | (E)-{(5-chloro-benzo[b]thiophen-3-yl)-[2-(2,6-difluoro-phenyl)-vinylcarbamoyl]-methyl}-phosphonic acid bis-(tert-butylcarbonyloxymethyl) ester, |
| 227 | (E)-{(5-chloro-benzo[b]thiophen-3-yl)-[2-(2-chloro-phenyl)-vinylcarbamoyl]-methyl}-phosphonic acid bis-(tert-butylcarbonyloxymethyl) ester, |
| 228 | (E)-{(5-chloro-benzo[b]thiophen-3-yl)-[2-(3-chloro-phenyl)-vinylcarbamoyl]-methyl}-phosphonic acid bis-(tert-butylcarbonyloxymethyl) ester, |
| 229 | (E)-{(5-chloro-benzo[b]thiophen-3-yl)-[2-(3,5-difluoro-phenyl)-vinylcarbamoyl]-methyl}-phosphonic acid bis-(tert-butylcarbonyloxymethyl) ester, |
| 230 | (E)-{(5-chloro-benzo[b]thiophen-3-yl)-[2-(2,3-difluoro-phenyl)-vinylcarbamoyl]-methyl}-phosphonic acid bis-(tert-butylcarbonyloxymethyl) ester, |
| 231 | (E)-{(5-chloro-benzo[b]thiophen-3-yl)-[2-(2-bromo-phenyl)-vinylcarbamoyl]-methyl}-phosphonic acid bis-(tert-butylcarbonyloxymethyl) ester, |
| 232 | (E)-{(5-chloro-benzo[b]thiophen-3-yl)-[2-(2,3-dimethoxy-phenyl)-vinylcarbamoyl]-methyl}-phosphonic acid bis-(tert-butylcarbonyloxymethyl) ester, |

| Cpd | Name |
|---|---|
| 233 | (E)-{(5-chloro-benzo[b]thiophen-3-yl)-[2-(3-nitro-phenyl)-vinylcarbamoyl]-methyl}-phosphonic acid bis-(tert-butylcarbonyloxymethyl) ester, |
| 234 | (E)-{(5-chloro-benzo[b]thiophen-3-yl)-[2-(3-bromo-phenyl)-vinylcarbamoyl]-methyl}-phosphonic acid bis-(tert-butylcarbonyloxymethyl) ester, |
| 235 | (E)-{(5-chloro-benzo[b]thiophen-3-yl)-[2-(3,5-dimethoxy-phenyl)-vinylcarbamoyl]-methyl}-phosphonic acid bis-(tert-butylcarbonyloxymethyl) ester, |
| 236 | (E)-{(5-chloro-benzo[b]thiophen-3-yl)-[2-(2,5-difluoro-phenyl)-vinylcarbamoyl]-methyl}-phosphonic acid bis-(tert-butylcarbonyloxymethyl) ester, |
| 237 | (E)-{(5-chloro-benzo[b]thiophen-3-yl)-[2-(3,5-dichloro-phenyl)-vinylcarbamoyl]-methyl}-phosphonic acid bis-(tert-butylcarbonyloxymethyl) ester, |
| 238 | (E)-{(5-chloro-benzo[b]thiophen-3-yl)-[2-(2,4-difluoro-phenyl)-vinylcarbamoyl]-methyl}-phosphonic acid bis-(tert-butylcarbonyloxymethyl) ester, |
| 239 | (E)-{(5-chloro-benzo[b]thiophen-3-yl)-[2-(3-amino-phenyl)-vinylcarbamoyl]-methyl}-phosphonic acid bis-(tert-butylcarbonyloxymethyl) ester, |
| 240 | (E)-{(5-chloro-benzo[b]thiophen-3-yl)-[2-(2-methoxy-phenyl)-vinylcarbamoyl]-methyl}-phosphonic acid (tert-butylcarbonyloxymethyl) ester, |
| 241 | (E)-[(5-chloro-benzo[b]thiophen-3-yl)-(2-pyridin-2-yl-vinylcarbamoyl)-methyl]-phosphonic acid (tert-butylcarbonyloxymethyl) ester, |
| 242 | (E)-{(5-chloro-benzo[b]thiophen-3-yl)-[2-(3-trifluoromethoxy-phenyl)-vinylcarbamoyl]-methyl}-phosphonic acid (tert-butylcarbonyloxymethyl) ester, |
| 243 | (E)-{(5-chloro-benzo[b]thiophen-3-yl)-[2-(3-methoxy-phenyl)-vinylcarbamoyl]-methyl}-phosphonic acid (tert-butylcarbonyloxymethyl) ester, |
| 244 | (E)-{(5-chloro-benzo[b]thiophen-3-yl)-[2-(2,6-difluoro-phenyl)-vinylcarbamoyl]-methyl}-phosphonic acid (tert-butylcarbonyloxymethyl) ester, |
| 245 | (E)-{(5-chloro-benzo[b]thiophen-3-yl)-[2-(2-chloro-phenyl)-vinylcarbamoyl]-methyl}-phosphonic acid (tert-butylcarbonyloxymethyl) ester, |
| 246 | (E)-{(5-chloro-benzo[b]thiophen-3-yl)-[2-(3-chloro-phenyl)-vinylcarbamoyl]-methyl}-phosphonic acid (tert-butylcarbonyloxymethyl) ester, |
| 247 | (E)-{(5-chloro-benzo[b]thiophen-3-yl)-[2-(3,5-difluoro-phenyl)-vinylcarbamoyl]-methyl}-phosphonic acid (tert-butylcarbonyloxymethyl) ester, |
| 248 | (E)-{(5-chloro-benzo[b]thiophen-3-yl)-[2-(2,3-difluoro-phenyl)-vinylcarbamoyl]-methyl}-phosphonic acid (tert-butylcarbonyloxymethyl) ester, |
| 249 | (E)-{(5-chloro-benzo[b]thiophen-3-yl)-[2-(2-bromo-phenyl)-vinylcarbamoyl]-methyl}-phosphonic acid (tert-butylcarbonyloxymethyl) ester, |
| 250 | (E)-{(5-chloro-benzo[b]thiophen-3-yl)-[2-(2,3-dimethoxy-phenyl)-vinylcarbamoyl]-methyl}-phosphonic acid (tert-butylcarbonyloxymethyl) ester, |
| 251 | (E)-{(5-chloro-benzo[b]thiophen-3-yl)-[2-(3-nitro-phenyl)-vinylcarbamoyl]-methyl}-phosphonic acid (tert-butylcarbonyloxymethyl) ester, |
| 252 | (E)-{(5-chloro-benzo[b]thiophen-3-yl)-[2-(3-bromo-phenyl)-vinylcarbamoyl]-methyl}-phosphonic acid (tert-butylcarbonyloxymethyl) ester, |
| 253 | (E)-{(5-chloro-benzo[b]thiophen-3-yl)-[2-(3,5-dimethoxy-phenyl)-vinylcarbamoyl]-methyl}-phosphonic acid (tert-butylcarbonyloxymethyl) ester, |
| 254 | (E)-{(5-chloro-benzo[b]thiophen-3-yl)-[2-(2,5-difluoro-phenyl)-vinylcarbamoyl]-methyl}-phosphonic acid (tert-butylcarbonyloxymethyl) ester, |
| 255 | (E)-{(5-chloro-benzo[b]thiophen-3-yl)-[2-(3,5-dichloro-phenyl)-vinylcarbamoyl]-methyl}-phosphonic acid (tert-butylcarbonyloxymethyl) ester, |
| 256 | (E)-{(5-chloro-benzo[b]thiophen-3-yl)-[2-(2,4-difluoro-phenyl)-vinylcarbamoyl]-methyl}-phosphonic acid (tert-butylcarbonyloxymethyl) ester, |
| 257 | (E)-{(5-chloro-benzo[b]thiophen-3-yl)-[2-(3-amino-phenyl)-vinylcarbamoyl]-methyl}-phosphonic acid (tert-butylcarbonyloxymethyl) ester, |
| 258 | (E)-2-{(5-chloro-benzo[b]thiophen-3-yl)-[2-(2-methoxy-phenyl)-vinylcarbamoyl]-methyl}-1,3,2-dioxaphosphorinane 2-oxide, |
| 259 | (E)-2-[(5-chloro-benzo[b]thiophen-3-yl)-(2-pyridin-2-ylvinylcarbamoyl)-methyl]-1,3,2-dioxaphosphorinane 2-oxide, |
| 260 | (E)-2-{(5-chloro-benzo[b]thiophen-3-yl)-[2-(3-trifluoromethoxy-phenyl)-vinylcarbamoyl]-methyl}-1,3,2-dioxaphosphorinane 2-oxide, |
| 261 | (E)-2-{(5-chloro-benzo[b]thiophen-3-yl)-[2-(3-methoxy-phenyl)-vinylcarbamoyl]-methyl}-1,3,2-dioxaphosphorinane 2-oxide, |
| 262 | (E)-2-{(5-chloro-benzo[b]thiophen-3-yl)-[2-(2,6-difluoro-phenyl)-vinylcarbamoyl]-methyl}-1,3,2-dioxaphosphorinane 2-oxide, |
| 263 | (E)-2-{(5-chloro-benzo[b]thiophen-3-yl)-[2-(2-chloro-phenyl)-vinylcarbamoyl]-methyl}-1,3,2-dioxaphosphorinane 2-oxide, |

| Cpd | Name |
|---|---|
| 264 | (E)-2-{(5-chloro-benzo[b]thiophen-3-yl)-[2-(3-chloro-phenyl)-vinylcarbamoyl]-methyl}-1,3,2-dioxaphosphorinane 2-oxide, |
| 265 | (E)-2-{(5-chloro-benzo[b]thiophen-3-yl)-[2-(3,5-difluoro-phenyl)-vinylcarbamoyl]-methyl}-1,3,2-dioxaphosphorinane 2-oxide, |
| 266 | (E)-2-{(5-chloro-benzo[b]thiophen-3-yl)-[2-(2,3-difluoro-phenyl)-vinylcarbamoyl]-methyl}-1,3,2-dioxaphosphorinane 2-oxide, |
| 267 | (E)-2-{(5-chloro-benzo[b]thiophen-3-yl)-[2-(2-bromo-phenyl)-vinylcarbamoyl]-methyl}-1,3,2-dioxaphosphorinane 2-oxide, |
| 268 | (E)-2-{(5-chloro-benzo[b]thiophen-3-yl)-[2-(2,3-dimethoxy-phenyl)-vinylcarbamoyl]-methyl}-1,3,2-dioxaphosphorinane 2-oxide, |
| 269 | (E)-2-{(5-chloro-benzo[b]thiophen-3-yl)-[2-(3-nitro-phenyl)-vinylcarbamoyl]-methyl}-1,3,2-dioxaphosphorinane 2-oxide, |
| 270 | (E)-2-{(5-chloro-benzo[b]thiophen-3-yl)-[2-(3-bromo-phenyl)-vinylcarbamoyl]-methyl}-1,3,2-dioxaphosphorinane 2-oxide, |
| 271 | (E)-2-{(5-chloro-benzo[b]thiophen-3-yl)-[2-(3,5-dimethoxy-phenyl)-vinylcarbamoyl]-methyl}-1,3,2-dioxaphosphorinane 2-oxide, |
| 272 | (E)-2-{(5-chloro-benzo[b]thiophen-3-yl)-[2-(2,5-difluoro-phenyl)-vinylcarbamoyl]-methyl}-1,3,2-dioxaphosphorinane 2-oxide, |
| 273 | (E)-2-{(5-chloro-benzo[b]thiophen-3-yl)-[2-(3,5-dichloro-phenyl)-vinylcarbamoyl]-methyl}-1,3,2-dioxaphosphorinane 2-oxide, |
| 274 | (E)-2-{(5-chloro-benzo[b]thiophen-3-yl)-[2-(2,4-difluoro-phenyl)-vinylcarbamoyl]-methyl}-1,3,2-dioxaphosphorinane 2-oxide, |
| 275 | (E)-2-{(5-chloro-benzo[b]thiophen-3-yl)-[2-(3-amino-phenyl)-vinylcarbamoyl]-methyl}-1,3,2-dioxaphosphorinane 2-oxide, |
| 276 | (E)-{(5-chloro-benzo[b]thiophen-3-yl)-[2-(2-methoxy-phenyl)-vinylcarbamoyl]-methyl}-phosphonic acid (isopropyloxycarbonyloxymethyl) ester, |
| 277 | (E)-[(5-chloro-benzo[b]thiophen-3-yl)-(2-pyridin-2-yl-vinylcarbamoyl)-methyl]-phosphonic acid (isopropyloxycarbonyloxymethyl) ester, |
| 278 | (E)-{(5-chloro-benzo[b]thiophen-3-yl)-[2-(3-trifluoromethoxy-phenyl)-vinylcarbamoyl]-methyl}-phosphonic acid (isopropyloxycarbonyloxymethyl) ester, |
| 279 | (E)-{(5-chloro-benzo[b]thiophen-3-yl)-[2-(3-methoxy-phenyl)-vinylcarbamoyl]-methyl}-phosphonic acid (isopropyloxycarbonyloxymethyl) ester, |
| 280 | (E)-{(5-chloro-benzo[b]thiophen-3-yl)-[2-(2,6-difluoro-phenyl)-vinylcarbamoyl]-methyl}-phosphonic acid (isopropyloxycarbonyloxymethyl) ester, |
| 281 | (E)-{(5-chloro-benzo[b]thiophen-3-yl)-[2-(2-chloro-phenyl)-vinylcarbamoyl]-methyl}-phosphonic acid (isopropyloxycarbonyloxymethyl) ester, |
| 282 | (E)-{(5-chloro-benzo[b]thiophen-3-yl)-[2-(3-chloro-phenyl)-vinylcarbamoyl]-methyl}-phosphonic acid (isopropyloxycarbonyloxymethyl) ester, |
| 283 | (E)-{(5-chloro-benzo[b]thiophen-3-yl)-[2-(3,5-difluoro-phenyl)-vinylcarbamoyl]-methyl}-phosphonic acid (isopropyloxycarbonyloxymethyl) ester, |
| 284 | (E)-{(5-chloro-benzo[b]thiophen-3-yl)-[2-(2,3-difluoro-phenyl)-vinylcarbamoyl]-methyl}-phosphonic acid (isopropyloxycarbonyloxymethyl) ester, |
| 285 | (E)-{(5-chloro-benzo[b]thiophen-3-yl)-[2-(2-bromo-phenyl)-vinylcarbamoyl]-methyl} phosphonic acid (isopropyloxycarbonyloxymethyl) ester, |
| 286 | (E)-{(5-chloro-benzo[b]thiophen-3-yl)-[2-(2,3-dimethoxy-phenyl)-vinylcarbamoyl]-methyl}-phosphonic acid (isopropyloxycarbonyloxymethyl) ester, |
| 287 | (E)-{(5-chloro-benzo[b]thiophen-3-yl)-[2-(3-nitro-phenyl)-vinylcarbamoyl]-methyl}-phosphonic acid (isopropyloxycarbonyloxymethyl) ester, |
| 288 | (E)-{(5-chloro-benzo[b]thiophen-3-yl)-[2-(3-bromo-phenyl)-vinylcarbamoyl]-methyl}-phosphonic acid (isopropyloxycarbonyloxymethyl) ester, |
| 289 | (E)-{(5-chloro-benzo[b]thiophen-3-yl)-[2-(3,5-dimethoxy-phenyl)-vinylcarbamoyl]-methyl}-phosphonic acid (isopropyloxycarbonyloxymethyl) ester, |
| 290 | (E)-{(5-chloro-benzo[b]thiophen-3-yl)-[2-(2,5-difluoro-phenyl)-vinylcarbamoyl]-methyl}-phosphonic acid (isopropyloxycarbonyloxymethyl) ester, |
| 291 | (E)-{(5-chloro-benzo[b]thiophen-3-yl)-[2-(3,5-dichloro-phenyl)-vinylcarbamoyl]-methyl}-phosphonic acid (isopropyloxycarbonyloxymethyl) ester, |
| 292 | (E)-{(5-chloro-benzo[b]thiophen-3-yl)-[2-(2,4-difluoro-phenyl)-vinylcarbamoyl]-methyl}-phosphonic acid (isopropyloxycarbonyloxymethyl) ester, |
| 293 | (E)-{(5-chloro-benzo[b]thiophen-3-yl)-[2-(3-amino-phenyl)-vinylcarbamoyl]-methyl}-phosphonic acid (isopropyloxycarbonyloxymethyl) ester, |
| 294 | (E)-{(5-chloro-benzo[b]thiophen-3-yl)-[2-(3-fluoro-5-chloro-phenyl)-vinylcarbamoyl]-methyl}-methyl-phosphinic acid, |
| 295 | (E)-{(5-chloro-benzo[b]thiophen-3-yl)-[2-(2-fluoro-3-chloro-phenyl)-vinylcarbamoyl]-methyl}-methyl-phosphinic acid, |
| 296 | (E)-{(5-chloro-benzo[b]thiophen-3-yl)-[2-(3-chloro-4-fluoro-phenyl)-vinylcarbamoyl]-methyl}-methyl-phosphinic acid, |

| Cpd | Name |
|---|---|
| 297 | (E)-{(5-chloro-benzo[b]thiophen-3-yl)-[2-(2-fluoro-5-chloro-phenyl)-vinylcarbamoyl]-methyl}-methyl-phosphinic acid, |
| 298 | (E)-{(5-chloro-benzo[b]thiophen-3-yl)-[2-(3,5-dibromo-phenyl)-vinylcarbamoyl]-methyl}-methyl-phosphinic acid, |
| 299 | (E)-{(5-chloro-benzo[b]thiophen-3-yl)-[2-(3-cyano-phenyl)-vinylcarbamoyl]-methyl}-methyl-phosphinic acid, |
| 300 | (E)-{(5-chloro-benzo[b]thiophen-3-yl)-[2-(2-cyano-phenyl)-vinylcarbamoyl]-methyl}-methyl-phosphinic acid, |
| 301 | (E)-{(5-chloro-benzo[b]thiophen-3-yl)-[2-(3-fluoro-5-trifluoromethyl-phenyl)-vinylcarbamoyl]-methyl}-methyl-phosphinic acid, |
| 302 | (E)-{(5-chloro-benzo[b]thiophen-3-yl)-[2-(3-fluoro-5-chloro-phenyl)-vinylcarbamoyl]-methyl}-phosphonic acid, |
| 303 | (E)-{(5-chloro-benzo[b]thiophen-3-yl)-[2-(2-fluoro-3-chloro-phenyl)-vinylcarbamoyl]-methyl}-phosphonic acid, |
| 304 | (E)-{(5-chloro-benzo[b]thiophen-3-yl)-[2-(3-chloro-4-fluoro-phenyl)-vinylcarbamoyl]-methyl}-phosphonic acid, |
| 305 | (E)-{(5-chloro-benzo[b]thiophen-3-yl)-[2-(2-fluoro-5-chloro-phenyl)-vinylcarbamoyl]-methyl}-phosphonic acid, |
| 306 | (E)-{(5-chloro-benzo[b]thiophen-3-yl)-[2-(3,5-dibromo-phenyl)-vinylcarbamoyl]-methyl}-phosphonic acid, |
| 307 | (E)-{(5-chloro-benzo[b]thiophen-3-yl)-[2-(3-cyano-phenyl)-vinylcarbamoyl]-methyl}-phosphonic acid, |
| 308 | (E)-{(5-chloro-benzo[b]thiophen-3-yl)-[2-(2-cyano-phenyl)-vinylcarbamoyl]-methyl}-phosphonic acid, |
| 309 | (E)-{(5-chloro-benzo[b]thiophen-3-yl)-[2-(3-fluoro-5-trifluoromethyl-phenyl)-vinylcarbamoyl]-methyl}-phosphonic acid, |
| 310 | (E)-{(5-chloro-benzo[b]thiophen-3-yl)-[2-(3-fluoro-5-chloro-phenyl)-vinylcarbamoyl]-methyl}-methyl-phosphinic acid (tert-butylcarbonyloxymethyl) ester, |
| 311 | (E)-{(5-chloro-benzo[b]thiophen-3-yl)-[2-(2-fluoro-3-chloro-phenyl)-vinylcarbamoyl]-methyl}-methyl-phosphinic acid (tert-butylcarbonyloxymethyl) ester, |
| 312 | (E)-{(5-chloro-benzo[b]thiophen-3-yl)-[2-(3-chloro-4-fluoro-phenyl)-vinylcarbamoyl]-methyl}-methyl-phosphinic acid (tert-butylcarbonyloxymethyl) ester, |
| 313 | (E)-{(5-chloro-benzo[b]thiophen-3-yl)-[2-(2-fluoro-5-chloro-phenyl)-vinylcarbamoyl]-methyl}-methyl-phosphinic acid (tert-butylcarbonyloxymethyl) ester, |
| 314 | (E)-{(5-chloro-benzo[b]thiophen-3-yl)-[2-(3,5-dibromo-phenyl)-vinylcarbamoyl]-methyl}-methyl-phosphinic acid (tert-butylcarbonyloxymethyl) ester, |
| 315 | (E)-{(5-chloro-benzo[b]thiophen-3-yl)-[2-(3-cyano-phenyl)-vinylcarbamoyl]-methyl}-methyl-phosphinic acid (tert-butylcarbonyloxymethyl) ester, |
| 316 | (E)-{(5-chloro-benzo[b]thiophen-3-yl)-[2-(2-cyano-phenyl)-vinylcarbamoyl]-methyl}-methyl-phosphinic acid (tert-butylcarbonyloxymethyl) ester, |
| 317 | (E)-{(5-chloro-benzo[b]thiophen-3-yl)-[2-(3-fluoro-5-trifluoromethyl-phenyl)-vinylcarbamoyl]-methyl}-methyl-phosphinic acid (tert-butylcarbonyloxymethyl) ester, |
| 318 | (E)-{(5-chloro-benzo[b]thiophen-3-yl)-[2-(3-fluoro-5-chloro-phenyl)-vinylcarbamoyl]-methyl}-phosphonic acid bis-(tert-butylcarbonyloxymethyl) ester, |
| 319 | (E)-{(5-chloro-benzo[b]thiophen-3-yl)-[2-(2-fluoro-3-chloro-phenyl)-vinylcarbamoyl]-methyl}-phosphonic acid bis-(tert-butylcarbonyloxymethyl) ester, |
| 320 | (E)-{(5-chloro-benzo[b]thiophen-3-yl)-[2-(3-chloro-4-fluoro-phenyl)-vinylcarbamoyl]-methyl}-phosphonic acid bis-(tert-butylcarbonyloxymethyl) ester, |
| 321 | (E)-{(5-chloro-benzo[b]thiophen-3-yl)-[2-(2-fluoro-5-chloro-phenyl)-vinylcarbamoyl]-methyl}-phosphonic acid bis-(tert-butylcarbonyloxymethyl) ester, |
| 322 | (E)-{(5-chloro-benzo[b]thiophen-3-yl)-[2-(3,5-dibromo-phenyl)-vinylcarbamoyl]-methyl}-phosphonic acid bis-(tert-butylcarbonyloxymethyl) ester, |
| 323 | (E)-{(5-chloro-benzo[b]thiophen-3-yl)-[2-(3-cyano-phenyl)-vinylcarbamoyl]-methyl}-phosphonic acid bis-(tert-butylcarbonyloxymethyl) ester, |
| 324 | (E)-{(5-chloro-benzo[b]thiophen-3-yl)-[2-(2-cyano-phenyl)-vinylcarbamoyl]-methyl}-phosphonic acid bis-(tert-butylcarbonyloxymethyl) ester, |
| 325 | (E)-{(5-chloro-benzo[b]thiophen-3-yl)-[2-(3-fluoro-5-trifluoromethyl-phenyl)-vinylcarbamoyl]-methyl}-phosphonic acid bis-(tert-butylcarbonyloxymethyl) ester, |
| 326 | (E)-{(5-chloro-benzo[b]thiophen-3-yl)-[2-(3-fluoro-5-chloro-phenyl)-vinylcarbamoyl]-methyl}-phosphonic acid (tert-butylcarbonyloxymethyl) ester, |
| 327 | (E)-{(5-chloro-benzo[b]thiophen-3-yl)-[2-(2-fluoro-3-chloro-phenyl)-vinylcarbamoyl]-methyl}-phosphonic acid (tert-butylcarbonyloxymethyl) ester, |

| Cpd | Name |
|---|---|
| 328 | (E)-{(5-chloro-benzo[b]thiophen-3-yl)-[2-(3-chloro-4-fluoro-phenyl)-vinylcarbamoyl]-methyl}-phosphonic acid (tert-butylcarbonyloxymethyl) ester, |
| 329 | (E)-{(5-chloro-benzo[b]thiophen-3-yl)-[2-(2-fluoro-5-chloro-phenyl)-vinylcarbamoyl]-methyl}-phosphonic acid (tert-butylcarbonyloxymethyl) ester, |
| 330 | (E)-{(5-chloro-benzo[b]thiophen-3-yl)-[2-(3,5-dibromo-phenyl)-vinylcarbamoyl]-methyl}-phosphonic acid (tert-butylcarbonyloxymethyl) ester, |
| 331 | (E)-{(5-chloro-benzo[b]thiophen-3-yl)-[2-(3-cyano-phenyl)-vinylcarbamoyl]-methyl}-phosphonic acid (tert-butylcarbonyloxymethyl) ester, |
| 332 | (E)-{(5-chloro-benzo[b]thiophen-3-yl)-[2-(2-cyano-phenyl)-vinylcarbamoyl]-methyl}-phosphonic acid (tert-butylcarbonyloxymethyl) ester, |
| 333 | (E)-{(5-chloro-benzo[b]thiophen-3-yl)-[2-(3-fluoro-5-trifluoromethyl-phenyl)-vinylcarbamoyl]-methyl}-phosphonic acid (tert-butylcarbonyloxymethyl) ester, |
| 334 | (E)-2-{(5-chloro-benzo[b]thiophen-3-yl)-[2-(3,4-difluoro-phenyl)-vinylcarbamoyl]-methyl}-1,3,2-dioxaphosphorinane 2-oxide, |
| 335 | (E)-2-{(5-chloro-benzo[b]thiophen-3-yl)-[2-(2-fluoro-3-chloro-phenyl)-vinylcarbamoyl]-methyl}-1,3,2-dioxaphosphorinane 2-oxide, |
| 336 | (E)-2-{(5-chloro-benzo[b]thiophen-3-yl)-[2-(3-chloro-4-fluoro-phenyl)-vinylcarbamoyl]-methyl}-1,3,2-dioxaphosphorinane 2-oxide, |
| 337 | (E)-2-{(5-chloro-benzo[b]thiophen-3-yl)-[2-(2-fluoro-5-chloro-phenyl)-vinylcarbamoyl]-methyl}-1,3,2-dioxaphosphorinane 2-oxide, |
| 338 | (E)-2-{(5-chloro-benzo[b]thiophen-3-yl)-[2-(3,5-dibromo-phenyl)-vinylcarbamoyl]-methyl}-1,3,2-dioxaphosphorinane 2-oxide, |
| 339 | (E)-2-{(5-chloro-benzo[b]thiophen-3-yl)-[2-(3-cyano-phenyl)-vinylcarbamoyl]-methyl}-1,3,2-dioxaphosphorinane 2-oxide, |
| 340 | (E)-2-{(5-chloro-benzo[b]thiophen-3-yl)-[2-(2-cyano-phenyl)-vinylcarbamoyl]-methyl}-1,3,2-dioxaphosphorinane 2-oxide, |
| 341 | (E)-2-{(5-chloro-benzo[b]thiophen-3-yl)-[2-(3-fluoro-5-trifluoromethyl-phenyl)-vinylcarbamoyl]-methyl}-1,3,2-dioxaphosphorinane 2-oxide, |
| 342 | (E)-{(5-chloro-benzo[b]thiophen-3-yl)-[2-(3-fluoro-5-chloro-phenyl)-vinylcarbamoyl]-methyl}-phosphonic acid (isopropyloxycarbonyloxymethyl) ester, |
| 343 | (E)-{(5-chloro-benzo[b]thiophen-3-yl)-[2-(2-fluoro-3-chloro-phenyl)-vinylcarbamoyl]-methyl}-phosphonic acid (isopropyloxycarbonyloxymethyl) ester, |
| 344 | (E)-{(5-chloro-benzo[b]thiophen-3-yl)-[2-(3-chloro-4-fluoro-phenyl)-vinylcarbamoyl]-methyl}-phosphonic acid (isopropyloxycarbonyloxymethyl) ester, |
| 345 | (E)-{(5-chloro-benzo[b]thiophen-3-yl)-[2-(2-fluoro-5-chloro-phenyl)-vinylcarbamoyl]-methyl}-phosphonic acid (isopropyloxycarbonyloxymethyl) ester, |
| 346 | (E)-{(5-chloro-benzo[b]thiophen-3-yl)-[2-(3,5-dibromo-phenyl)-vinylcarbamoyl]-methyl}-phosphonic acid (isopropyloxycarbonyloxymethyl) ester, |
| 347 | (E)-{(5-chloro-benzo[b]thiophen-3-yl)-[2-(3-cyano-phenyl)-vinylcarbamoyl]-methyl}-phosphonic acid (isopropyloxycarbonyloxymethyl) ester, |
| 348 | (E)-{(5-chloro-benzo[b]thiophen-3-yl)-[2-(2-cyano-phenyl)-vinylcarbamoyl]-methyl}-phosphonic acid (isopropyloxycarbonyloxymethyl) ester, and |
| 349 | (E)-{(5-chloro-benzo[b]thiophen-3-yl)-[2-(3-fluoro-5-trifluoromethyl-phenyl)-vinylcarbamoyl]-methyl}-phosphonic acid (isopropyloxycarbonyloxymethyl) ester. |

The present invention is further directed to a process for preparing a compound of Formula (I) selected from the group consisting of:

2 (E)-{(5-chloro-benzo[b]thiophen-3-yl)-[2-(3,4-difluoro-phenyl)-vinylcarbamoyl]-methyl}-phosphonic acid,
17 (E)-{(5-chloro-benzo[b]thiophen-3-yl)-[2-(3,4-difluoro-phenyl)-vinylcarbamoyl]-methyl}-methyl-phosphinic acid,
164 (E)-{(5-chloro-benzo[b]thiophen-3-yl)-[2-(3,5-dichloro-phenyl)-vinylcarbamoyl]-methyl}-methyl-phosphinic acid,
181 (E)-{(5-chloro-benzo[b]thiophen-3-yl)-[2-(3,4-difluoro-phenyl)-vinylcarbamoyl]-methyl}-phosphonic acid (tert-butylcarbonyloxymethyl)ester,
185 (E)-{(5-chloro-benzo[b]thiophen-3-yl)-[2-(3,4-difluoro-phenyl)-vinylcarbamoyl]-methyl}-phosphonic acid [(isopropoxycarbonyloxy)-methyl]ester,
201 (E)-{(5-chloro-benzo[b]thiophen-3-yl)-[2-(3,5-dichloro-phenyl)-vinylcarbamoyl]-methyl}-phosphonic acid,
255 (E)-{(5-chloro-benzo[b]thiophen-3-yl)-[2-(3,5-dichloro-phenyl)-vinylcarbamoyl]-methyl}-phosphonic acid (tert-butylcarbonyloxymethyl) ester, and
291 (E)-{(5-chloro-benzo[b]thiophen-3-yl)-[2-(3,5-dichloro-phenyl)-vinylcarbamoyl]-methyl}-phosphonic acid (isopropyloxycarbonyloxymethyl) ester.

Discussion of Process Improvements

Scheme B depicts a reaction system whereby lithium complexes with the phosphonoyl α-methylene of a Compound B1, making the position amenable for reaction with isocyanate, thus enabling coupling of Compound B2 with a Compound B3 in the solvent THF. However, the reaction yield for Compound B5 was about 45% due to the formation of a urea impurity Compound B6 from the precursor intermediate Compound B4, thus providing an opportunity to develop a more efficient synthesis amenable to large scale production.

Scheme B
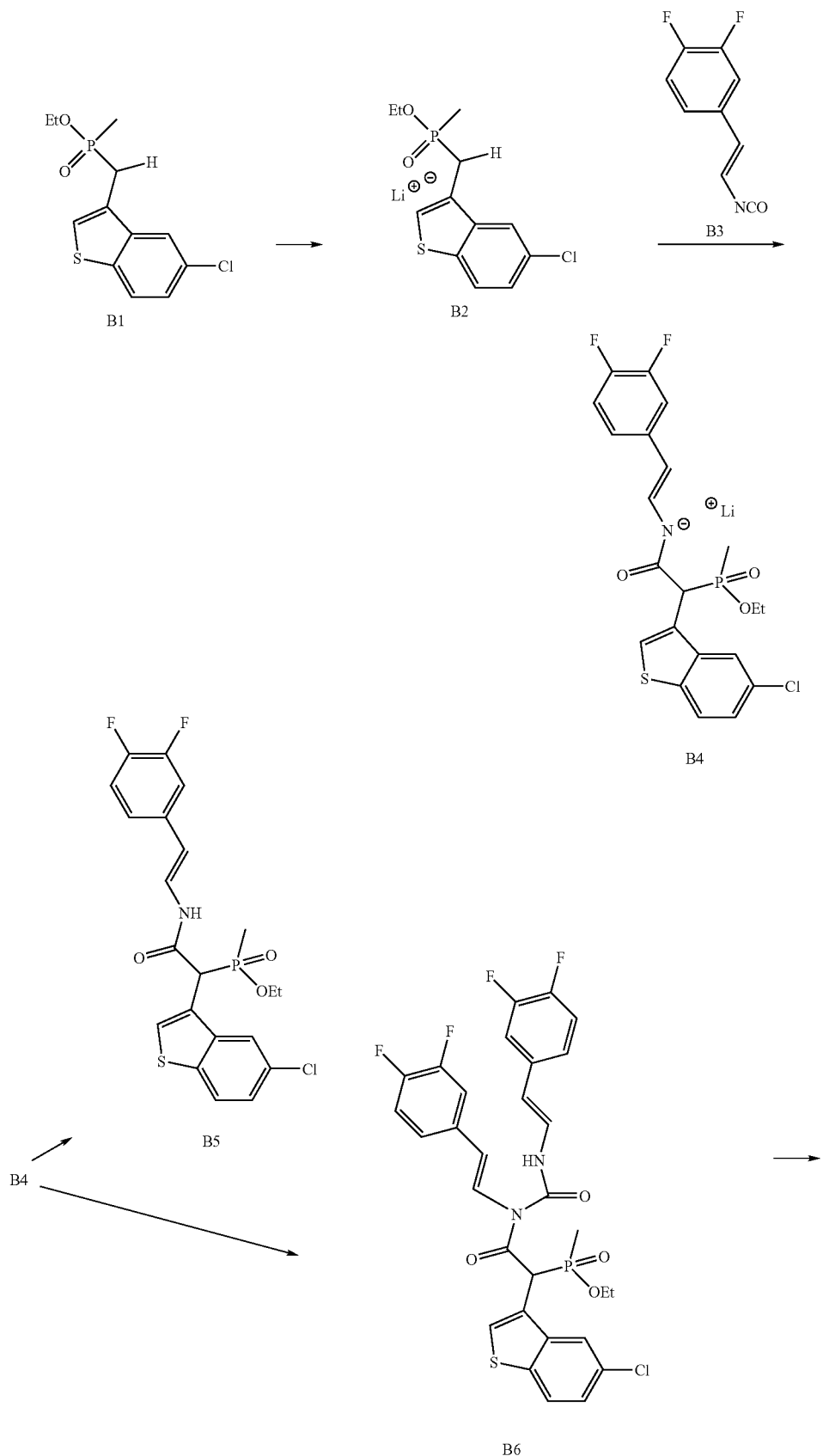

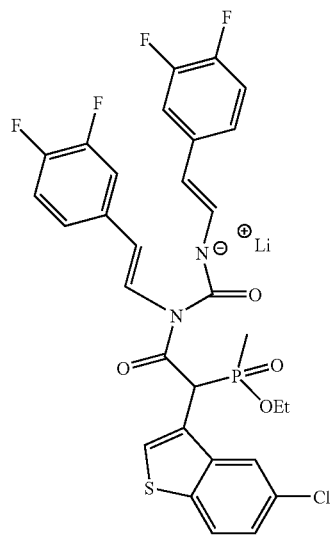

B7

As described in the literature, the reaction yield between a vinyl isocyanate and various Grignard or organolithium species may be increased by using a less-coordinating, less-polar solvent system such as a toluene/ether solvent/co-solvent mixture in place of a toluene/THF system, thus reducing the formation of a urea byproduct resulting from an excess amount of the isocyanate further reacting with the desired amide product (Kuramochi K, Watanabe H and Kitahara T, Synthetic Study on Oximidines: A Concise Synthesis of (Z)-Enamides, *Synlett,* 2000, 397-399). However, Kuramochi, et al. neither suggests using a mono-solvent system nor using a substoichiometric amount of the isocyanate to increase the yield of the desired product and provide the potential for an elegant, direct crystallization.

In the process of the present invention, we reasoned that Kuramochi's yield was increased by the use of less-coordinating, less-polar solvents in a solvent/co-solvent system. Although such a solvent/co-solvent system is not employed in the present invention, we replaced the solvent THF used in the method of synthesis disclosed in U.S. Patent Publication 2005/0176769 with the solvent toluene and increased the yield of the desired product Compound B5 from about 45% to a higher yield of about 57%.

Further, to obtain Compound B5 with reduced Compound B6 and other polymeric urea byproduct impurities resulting from isocyanate substitution via Compound B7, we also reduced the amount of isocyanate Compound B3 with respect to Compound B1, using 0.8 equivalents of Compound B3 and 1 equivalent of Compound B1. With these two improvements, Compound B5 was then able to be isolated as a solid by subsequent direct crystallization from a solvent mixture (for example, using a mixture of EtOAc and heptane) in a yield of from about 60% to about 65% with a purity of greater than about 97%.

Thus, a discovery of the present invention is that, when the isocyanate is present in a substoichiometric amount and the substituted organometallic species is present in the mono-solvent toluene, the yield of the desired Compound B5 is improved by minimizing the formation of Compound B6 and other polymeric urea byproducts. Moreover, direct crystallization of the final product Compound B5 is thus made possible, enabling an efficient synthesis amenable to large scale production.

Scheme C depicts a reaction system wherein TMSBr in pyridine solution was used to dealkylate the phosphinic acid ethyl ester Compound B5, making the position amenable for hydrolysis to obtain the compound of Formula (Ia). However, the reaction yield for the compound of Formula (Ia) was only about 60%, thus providing another opportunity to optimize the process.

Scheme C

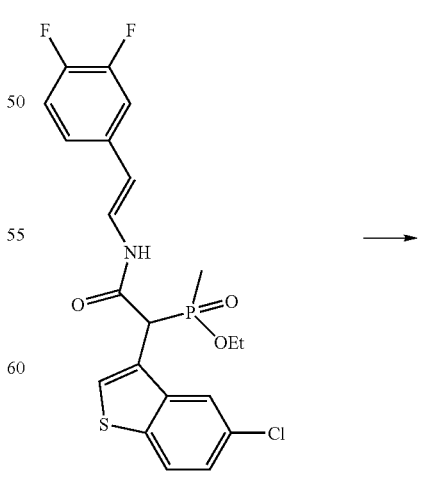

B5

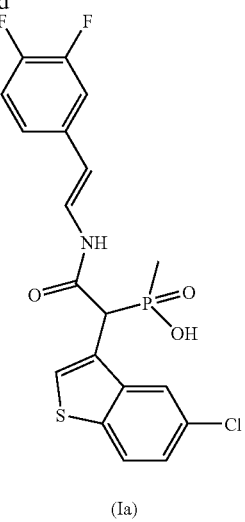

(Ia)

As described in the literature, the use of TMSBr in place of chlorotrimethylsilane (TMSCl) for dealkylating neat phosphonic acid dialkyl esters to the corresponding phosphonic acid may provide an improved reaction yield (McKenna C E, Higa M T, Cheung N H and McKenna M-C, The Facile Dealkylation of Phosphonic Acid Dialkyl Esters by Bromotrimethylsilane, *Tetrahedron Letters,* 1977, 2, 155-158).

Although McKenna shows an increase in reaction yield as a result of the use of TMSBr over TMSCl, there is no suggestion that a solvent used in the reaction system could have an effect on yield. Moreover, since McKenna's showing is regarding a neat phosphonic acid dialkyl ester, there is no suggestion that the reaction system could be operative for a phosphinic acid alkyl ester or that the use of a solvent and TMSBr for reaction with such a phosphinic acid could increase the yield.

In the process of the present invention, TMSBr was reacted with a phosphinic acid alkyl ester in an ACN solution. As a result, the yield of the compound of Formula (Ia) was increased to a range of from about 83% to about 95%; an improvement over previously described yields. While not wishing to be bound by theory, Applicants propose that, although the use of TMSBr over another reagent, such as TMSCl, has been shown to improve phosphonic acid reaction yield from the dialkyl esters, a discovery of the present invention is that, additionally, the use of a solvent such as ACN may act as an accelerant, thus making the TMSBr considerably more reactive.

The process of the present invention is also directed to preparing the compound of Formula (Ia) (Compound 17 hereinabove) and a salt thereof:

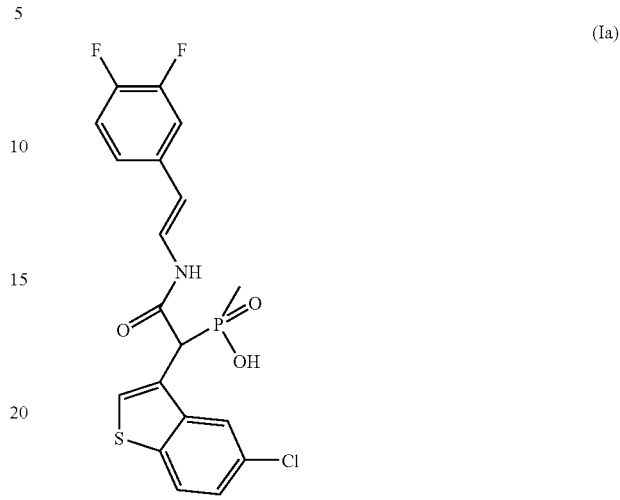

(Ia)

according to Scheme D, comprising the steps of:

Scheme D

Step 1. reacting a Compound B1 with a Compound B3, wherein Compound B1 and Compound B3 are present in a first ratio in toluene to provide a Compound B5, representative of a compound of Formula (I):

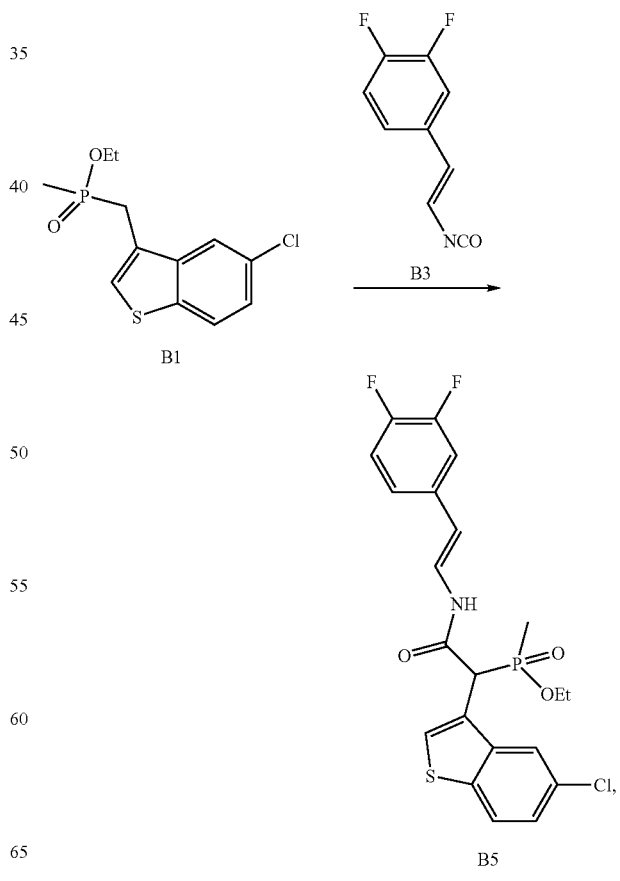

wherein in the first ratio, the amount of Compound B1 exceeds the amount of Compound B3 by about 0.2 equivalents;

Step 2. reacting the Compound B5 in the presence of TMSBr in acetonitrile and optionally present pyridine, wherein TMSBr and Compound B5 are in a second ratio, and wherein TMSBr and pyridine, when pyridine is present, are in a third ratio to provide the compound of Formula (Ia):

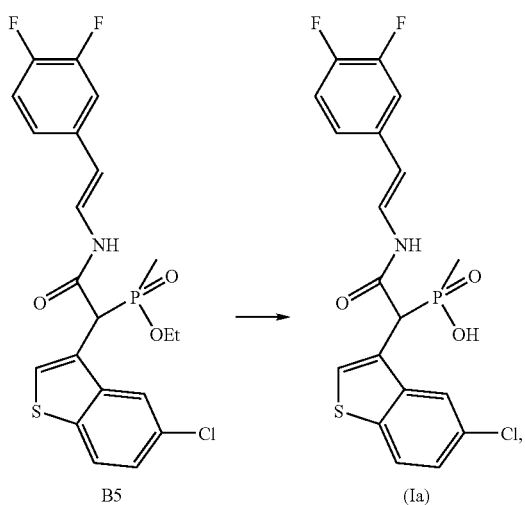

B5         (Ia)

wherein in the second ratio, TMSBr and Compound B5 are in a range of about 2.5:1 TMSBr:Compound B5 to about 2:1 TMSBr:Compound B5 and wherein in the third ratio, TMSBr and pyridine, when pyridine is present, are in a range of from about 1:1 TMSBr:pyridine to about 1:2 TMSBr:pyridine; and Step 3. reacting the compound of Formula (Ia) with choline hydroxide in a solvent mixture of MeOH and EtOAc, wherein MeOH and EtOAc are in a fourth ratio, to provide a Compound D1 as a salt, representative of a compound of Formula (I), wherein the salt is obtained by direct crystallization:

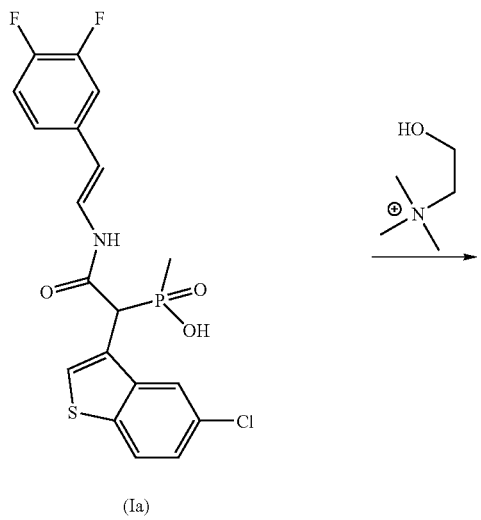

(Ia)

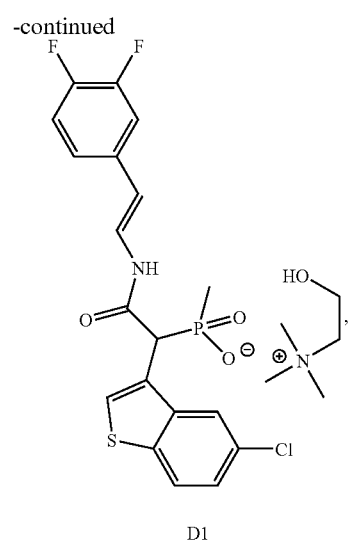

D1 wherein in the fourth ratio, MeOH and EtOAc are about 1:3 MeOH:EtOAc.

An example of the present invention includes an amount of Compound B1 in a range of from about 1.2 equivalents to about 1 equivalent and an amount of Compound B3 in a range of from about 1 equivalent to about 0.8 equivalents according to said first ratio.

An example of the present invention includes TMSBr in a range of about 2.5:1 TMSBr:Compound B5 to about 2:1 TMSBr:Compound B5, according to said second ratio, and pyridine is present in a range of about 1:1 TMSBr:pyridine to about 1:2 TMSBr:pyridine according to said third ratio.

An example of the present invention includes a process wherein in the third ratio, TMSBr and pyridine are about 1:2 TMSBr:pyridine.

An example of the present invention includes TMSBr in a range of about 2.5:1 TMSBr:Compound B5 to about 2:1 TMSBr:Compound B5, according to said second ratio, wherein pyridine is not present.

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art. Chemical terms are to be read from right to left, wherein the right-most group is attached to the core molecule and the left-most group is the terminal group. The formula (s) illustrating a term are to be read from left to right, wherein the left-most group is attached to the core molecule, as indicated by the dash, and the right-most group is the terminal group.

The term "$C_{1-8}$alkyl" means a saturated aliphatic branched or straight-chain hydrocarbon radical or linking group having from 1 up to 8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" also includes a "$C_{1-6}$alkyl" and "$C_{1-4}$alkyl" radical or linking group having from 1 up to 6 carbon atoms and 1 up to 4 carbon atoms respectively, such as methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl radicals may be attached to a core molecule via a terminal carbon atom or via a carbon atom within the chain. Similarly, substituent variables may be attached to an alkyl linking group when allowed by available valences.

The term "$C_{2-6}$alkenyl" means an alkyl radical or linking group having from 2 up to 6 carbon atoms in a linear or branched arrangement having at least one carbon-carbon double bond. The term "$C_{2-6}$alkenyl" also includes a "$C_{2-4}$alkenyl" radical or linking group having from 2 up to 4 carbon atoms, such as ethenyl (also referred to as vinyl), iso-propenyl, allyl (also referred to as propenyl), propylidene and the like.

The term "$C_{2-6}$alkynyl" means an alkyl radical or linking group having from 2 up to 6 carbon atoms in a linear or branched arrangement having at least one carbon-carbon triple bond. The term "$C_{2-8}$alkynyl" also includes a "$C_{2-4}$alkynyl" radical or linking group having from 2 up to 4 carbon atoms, such as ethynyl, propynyl and the like.

The term "$C_{1-6}$alkoxy" means an alkyl radical or linking group having from 1 up to 6 carbon atoms in a linear or branched arrangement, wherein the radical or linking group is attached through an oxygen linking atom, as in the formula: —O—$C_{1-6}$alkyl. The term "$C_{1-6}$alkoxy" also includes a "$C_{2-6}$alkoxy" and "$C_{1-4}$alkoxy" radical or linking group having from 2 up to 6 carbon atoms and from 1 up to 4 carbon atoms respectively, such as methoxy, ethoxy, propoxy, butoxy and the like. An alkoxy radical may be attached to a core molecule and further substituted as a linking group where indicated.

The term "cycloalkyl" means a saturated or partially unsaturated cyclic hydrocarbon ring system radical. The term "cycloalkyl" also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl or benzofused cycloalkyl ring system radical and the like, such as cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, acenaphthenyl, adamantanyl and the like.

The term "benzofused cycloalkyl" means a $C_{3-12}$cycloalkyl ring system radical having a benzene ring fused on the ring system on adjacent carbons. Examples of benzofused cycloalkyl in compounds representative of the present invention include a benzofused cycloalkyl ring system radical and the like, such as 1H-indenyl, indanyl and the like.

The term "aryl" means an unsaturated aromatic hydrocarbon ring system radical. Aryl ring systems include phenyl, naphthalenyl, azulenyl, anthracenyl and the like. Examples of aryl in compounds representative of the present invention include phenyl or naphthalenyl.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated "hetero" ring system radical. Heterocyclyl ring systems include azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azepanyl, hexahydro-1,4-diazepinyl, hexahydro-1,4-oxazepanyl, tetrahydro-furanyl, tetrahydrothienyl, tetrahydro-pyranyl, tetrahydro-pyridazinyl and the like.

The term "heterocyclyl" also includes a benzofused heterocyclyl ring system radical and the like, such as indolinyl (also referred to as 2,3-dihydro-indolyl), benzo[1,3]dioxolyl, 2,3-dihydro-1,4-benzodioxinyl, 2,3-dihydro-benzofuranyl, 1,2-dihydro-phthalazinyl and the like.

The term "benzofused heterocyclyl" means a heterocyclyl ring system radical having a benzene ring fused on the ring system on adjacent carbons. Examples of benzofused-heterocyclyl in compounds representative of the present invention include benzo[1,3]dioxolyl and 2,3-dihydro-indolyl.

The term "heteroaryl" means a monovalent, unsaturated aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like.

The term "heteroaryl" also includes a benzofused heteroaryl ring system radical and the like, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like.

The term "benzofused heteroaryl" means a heteroaryl ring system radical having a benzene ring fused on the ring system on adjacent carbons. Examples of benzofused heteroaryl in compounds representative of the present invention include indazolyl, indolyl, benzofuranyl and benzoimidazolyl.

The term "$C_{1-6}$alkoxycarbonyloxy" means a radical of the formula: —O—C(O)—O—$C_{1-6}$alkyl.

The term "($C_{1-6}$)alkylaminocarbonyl" means a radical of the formula: —C(O)—NH—$C_{1-6}$alkyl.

The term "di($C_{1-6}$)alkylaminocarbonyl" means a radical of the formula: —C(O)—N($C_{1-6}$alkyl)$_2$.

The term "$C_{1-6}$alkylcarbonyloxy" means a radical of the formula: —O—C(O)—$C_{1-6}$alkyl.

The term "$C_{1-6}$alkylcarbonylthio" means a radical of the formula: —S—C(O)—$C_{1-6}$alkyl.

The term "$C_{1-6}$alkylthio" means a radical of the formula: —S—$C_{1-8}$alkyl.

The term "aryl($C_{1-6}$)alkyl" means a radical of the formula: —$C_{1-6}$alkyl-aryl.

The term "aryl($C_{2-6}$)alkenyl" means a radical of the formula: —$C_{2-6}$alkenyl-aryl.

The term "aryloxy" means a radical of the formula: —O-aryl.

The term "halogen" or "halo" means the group chloro, bromo, fluoro or iodo.

The term "heteroaryloxy" means a radical of the formula: —O-heteroaryl.

The term "nitro" means a radical of the formula: —$NO_2$.

The term "oxo" means a radical of the formula: —C(O).

The term "ureido" means a linking group of the formula: —NH—C(O)—NH—.

The term "substituted" means the independent replacement of one or more hydrogen atoms within a radical with that amount of substituents allowed by available valences.

In general, IUPAC nomenclature rules are used herein.

Compound Forms

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, choline (or cholinate), clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to priority rules. In the "E" configuration, the substituents having higher priority are on opposite sides in relationship to the carbon-carbon double bond. In the "Z" configuration, the substituents having higher priority are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

SYNTHETIC EXAMPLES

The terms used in describing the invention are commonly used and known to those skilled in the art. When used herein, the following abbreviations have the indicated meanings:

| Abbreviation | Meaning |
| --- | --- |
| Cpd | compound |
| h/hr(s)/min(s) | hour(s)/min(s) |
| EtOAc | ethyl acetate |
| HPLC | High Pressure Liquid Chromatography |
| MeOH | methanol |
| n-BuLi | n-butyl lithium |
| RT/rt/r.t. | room temperature |
| THF | tetrahydrofuran |
| TMSBr | trimethylsilyl bromide |

Example 1

(E)-{(5-chloro-benzo[b]thiophen-3-yl)-[2-(3,4-difluoro-phenyl)-vinylcarbamoyl]-methyl}-methylphosphinic acid Formula (Ia)

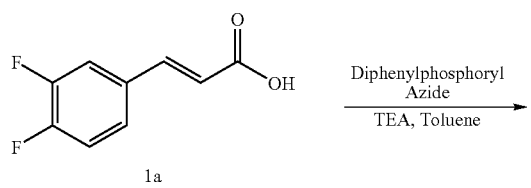

Step 1. 3-(3,4-difluoro-phenyl)-acryloyl azide (Cpd 1b)

3,4-difluorocinnamic acid Compound 1a (70.00 g, 380 mmol) was added to a three-neck 2 L flask equipped with an overhead mechanical stirrer, an internal temperature probe, and a nitrogen inlet. After flushing with nitrogen, toluene (700 mL) was added and the slurry was cooled with stirring to 10° C. Triethylamine (TEA) (53.0 mL, 380 mmol) was then added and the reaction became homogeneous. After cooling to 5° C., diphenylphosphoryl azide (81.9 mL, 380 mmol) was added over 15 minutes. The reaction was allowed to warm to room temperature and stirred for 15 h. When the reaction was complete, as shown by HPLC, sodium bicarbonate (3% aqueous solution, 650 mL) was added and the mixture was stirred vigorously. After separating the layers, the aqueous layer was extracted with EtOAc (2×700 mL). The first two organic extracts contained significant amounts of Compound 1b, as shown by HPLC. The extracts were combined and filtered through a plug of magnesium sulfate (173 g) on the top of the plug and silica gel (345 g) at the bottom of the plug. The plug was washed with 2 L of 50% EtOAc/hexanes. The filtrate was concentrated under reduced pressure at a temperature not exceeding 32° C. Further removal of residual solvent under high vacuum provided Compound 1b as a yellow solid (77.7 g, 98% yield). $^1$H NMR (400 MHz, CDCl$_3$): δ 7.58 (d, J=15.9 Hz, 2H), 7.3 (m, 1H), 7.2 (m, 1H), 7.14 (m, 1H), 6.26 (d, J=16.0 Hz, 1H).

Step 2. diethyl methylphosphonite (Cpd 1d)

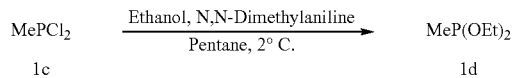

To a 3-neck 2 L round bottom flask equipped with a thermocouple, mechanical stirrer, addition funnel, and nitrogen inlet were added pentane (590 mL), ethanol (108.4 mL, 1.860 mol), and N,N-dimethylaniline (235.8 mL, 1.860 mol). The mixture was cooled to 0° C. and stirred under a nitrogen atmosphere. Methylphosphorous dichloride Compound 1c (100 g, 855 mmol) was added through the addition funnel over a period of about 1.8 h. After the addition was complete, the mixture was stirred for an additional 1.5 h at 0° C. The reaction mixture was then filtered through a 600 mL medium porosity frit. The filter cake was washed with 1.5 L of pentane. The cloudy filtrate was concentrated on a rotary evaporator at 0° C. and then distilled. The product Compound 1d, which was collected between 300 and 400 mTorr at a distillation head temperature of 20-22° C., was isolated as a clear oil (70.89 g, 62%) and used directly in the next step.

Step 3. (5-chloro-benzo[b]thiophen-3-ylmethyl)-methyl-phosphinic acid ethyl ester (Cpd B1)

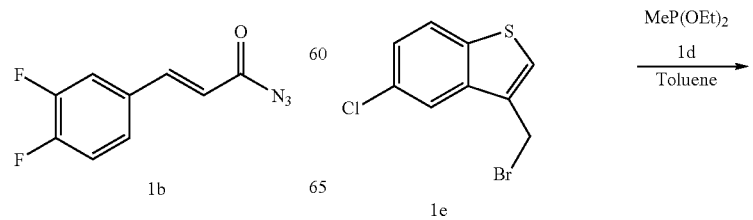

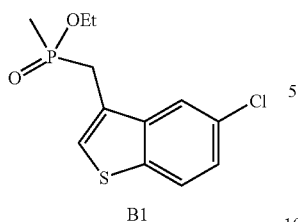

Into a 3 neck 2 L round bottom flask equipped with a nitrogen inlet, reflux condenser, heating mantle and thermocouple probe was added 3-bromomethyl-5-chloro-benzo[b]thiophene Compound 1e (46.45 g, 178 mmol). After flushing with nitrogen, toluene (464 mL) and diethylmethyl phosphonite Compound 1d (41.6 mL, 275 mmol) were added. The mixture was heated from room temperature to reflux over 25 minutes and then held at reflux for 1 h. The mixture was allowed to cool and additional diethylmethyl phosphonite Compound 1d (2.1 mL, 13.8 mmol) was added. The reaction was warmed back to reflux from 60° C. After 15 minutes at reflux, the mixture was allowed to cool and stirred at room temperature overnight. After filtration, the reaction mixture was concentrated under reduced pressure (60° C. on a rotary evaporator for 2 h and then over a period of 48 h under high vacuum at room temperature). The product Compound B1 was obtained as an oil contaminated with small amounts of residual toluene and a phosphorous containing impurity (55.0 g, 107%) and was used without additional purification in the next step. $^1$H NMR (400 MHz, CDCl$_3$): δ7.79 (d, J=1.9 Hz, 1H), 7.76 (d, J=8.6 Hz, 1H), 7.46 (d, J=3.7 Hz, 1H), 7.33 (dd, J=8.6, 2.0 Hz, 1H), 4.04 (m, 2H), 3.35 (m, 2H), 1.42 (d, J=13.7 Hz, 1H), 1.28 (d, J=7.0 Hz, 3H).

Step 4. 1,2-difluoro-4-(2-isocyanato-vinyl)-benzene (Cpd B3)

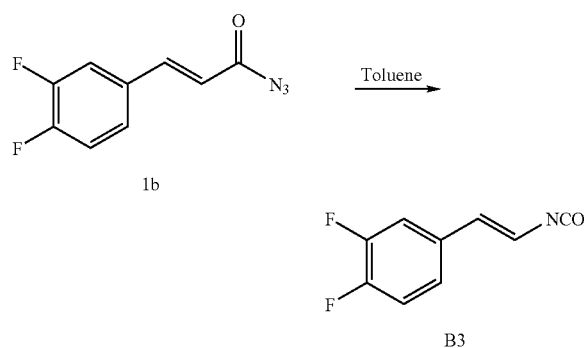

To a 3-neck, 1 L round bottom flask equipped with stir bar, thermometer, heating mantle and condenser was added Compound 1b (39.84 g, 190.5 mmol). After a nitrogen gas flush, toluene (500 mL) was added and the reaction flask was warmed to 67° C. over 18 minutes. As off-gassing commenced, the temperature was further raised to 78° C. over a period of 6 minutes to control the off-gassing. The mixture was carefully heated to 100° C. over 17 minutes and then held at that temperature for an additional 45 minutes until off-gassing ceased. The mixture containing Compound B3 in toluene was cooled to −78° C. for use in the next step.

Step 5. {(5-chloro-benzo[b]thiophen-3-yl)-[2-(3,4-difluoro-phenyl)-vinylcarbamoyl]-methyl}-methyl-phosphinic acid ethyl ester (Cpd B5)

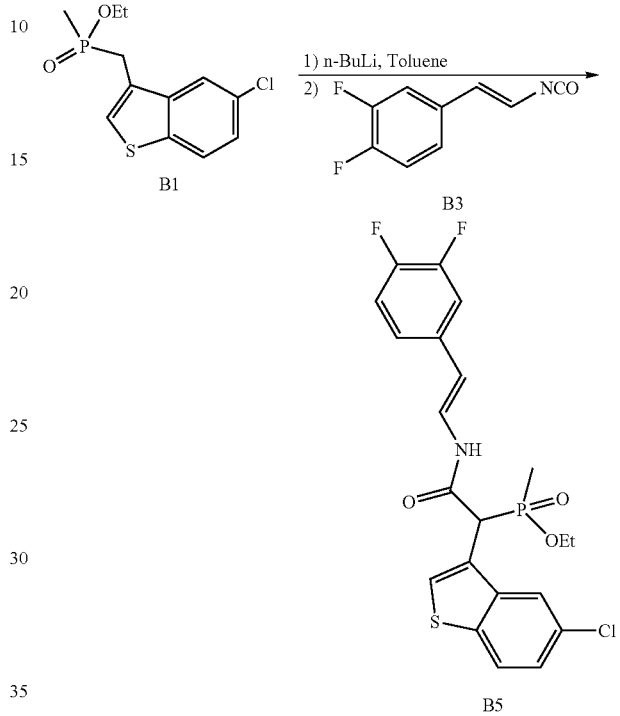

A 1-neck, 3 L round bottom flask equipped with a stir bar, nitrogen inlet and thermocouple probe and containing Compound B1 (55.0 g, 190.5 mmol) was flushed with nitrogen. Toluene (500 mL) was added and the solution was cooled to −70° C. n-BuLi (2.5 M in hexanes, 76.2 mL, 190.5 mmol) was then added over a period of 12 minutes. After stirring for an additional 15 minutes, the pre-cooled solution of Compound B3 was added over 12 minutes via cannula. The homogeneous mixture was stirred for 1.25 h and saturated aqueous ammonium chloride (600 mL) was added to the mixture. The reaction mixture was allowed to warm to room temperature. Water (400 mL) was added and the layers were mixed and separated. The aqueous layer was extracted two additional times with EtOAc (1×1 L and 1×500 mL). The combined organic layers were dried over magnesium sulfate, then filtered and concentrated. The resulting residue was taken up in 65% EtOAc/hexanes, loaded onto a plug of silica gel (590 g) and washed with 65% EtOAc/hexanes (3 L). The eluent was concentrated to a yellow foam which contained a mixture of the diastereomers of Compound B5 (65.04 g, crude yield 73%). MS (electrospray): exact mass calculated for C$_{21}$H$_{19}$ClF$_2$NO$_3$PS, 469.05; m/z found, 470.2 [MH]$^+$.

Diastereomer #1: $^1$H NMR (400 MHz, CDCl$_3$): δ 10.33 (d, J=10.2 Hz, 1H), 8.15 (d, J=3.7 Hz, 1H), 7.92 (d, J=1.8 Hz, 1H), 7.84 (d, J=8.6 Hz, 1H), ~7.35 (dd, J=8.6, 1.8 Hz, 1H), 7.2 (dd, J=14.7, 10.4 Hz, 1H), 6.8 to 7.0 (m, 3H), 6.03 (d, J=14.7 Hz, 1H), 5.09 (d, J=22.8 Hz, 1H) 4.2 to 4.4 (m, 2H), 1.82 (d, J=14.4 Hz, 3H), 1.30 (t, J=7.1 Hz, 3H).

Diastereomer #2: $^1$H NMR (400 MHz, CDCl$_3$): δ 9.97 (d, J=10.3 Hz, 1H), 8.05 (d, J=3.1 Hz, 1H), 7.92 (d, J=1.8 Hz, 1H), 7.84 (d, J=8.6 Hz, 1H), ~7.35 (dd, J=8.6, 1.8 Hz, 1H), ~7.2 (dd, J=14.7, 10.4 Hz, 1H), 6.8 to 7.0 (m, 3H), 6.10 (d, J=14.7 Hz, 1H), 4.99 (d, J=16.2 Hz, 1H), 4.1 to 4.2 (m, 2H), 1.60 (d, J=14.0 Hz, 3H), 1.41 (t, J=7.1 Hz, 3H).

Step 6. (E)-{(5-chloro-benzo[b]thiophen-3-yl)-[2-(3, 4-difluoro-phenyl)-vinylcarbamoyl]-methyl}-methyl-phosphinic acid Formula (Ia)

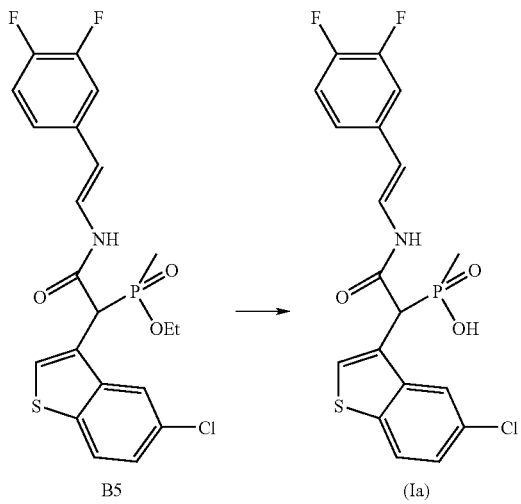

Into a 3 L round bottom flask equipped with stir bar, nitrogen inlet and thermocouple probe was added Compound B5 (60.0 g, 127.7 mmol). After a thorough nitrogen gas flush, pyridine (51.6 mL, 638.5 mmol) and then trimethylsilyl bromide (42.1 mL, 319.2 mmol) were added. The mixture was stirred at room temperature under nitrogen for a period of about 3.6 h, until HPLC analysis indicated the reaction was complete. The mixture was concentrated under reduced pressure at 40° C., then taken up three times in methanol (900 mL, 900 mL, 650 mL) and concentrated each time at 40° C. on a rotary evaporator. The residue was stirred mechanically for 2.5 h in 1 N HCl (800 mL) to provide a white solid. Alternatively, the crude was first taken up in MeOH (180 mL) and then dripped into mechanically stirred 1 N HCl (1350 mL) to provide the white solid.

The slurry was filtered through a medium frit and washed with 1 N HCl (200 mL) and then water (500 mL). The cake was dried under high vacuum overnight to provide a solid (114.82 g) that was taken up in methanol (171 mL) and stirred mechanically for 3 h. The resulting slurry was cooled to 0° C. and stirred for an additional hour, then filtered through a medium frit and washed with 75 mL of methanol. The cake was dried a second time under high vacuum to provide a solid (42.09 g) that was again taken up in methanol (200 mL) and stirred mechanically for 2 h. The resulting slurry was passed through a medium frit and washed with 75 mL of methanol. The filter cake was dried a third time under high vacuum to provide the title compound of Formula (Ia) (35.47 g, calculated yield 59%) as a 1:1 adduct with MeOH (93% product, 7% MeOH by weight, 32.99 g of product). MS (electrospray): exact mass calculated for $C_{19}H_{15}ClF_2NO_3PS$, 441.02; m/z found, 442.1 [MH]$^+$. $^1$H NMR (400 MHz, DMSO): δ 10.53 (d, J=10.1 Hz, 1H), 8.06 (d, J=8.6 Hz, 1H), 8.01 (d, J=3.4 Hz, 1H), 7.98 (d, J=2.0 Hz, 1H), 7.52 (ddd, J=12.4, 7.8, 2.0 Hz, 1H), 7.43 (dd, J=8.5, 2.0 Hz, 1H), 7.42 (dd, J=14.5, 10.2 Hz, 1H), 7.32 (m, 1H), 7.23 (m, 1H), 6.19 (d, J=14.7 Hz, 1H), 4.79 (d, J=21.0 Hz, 1H), 1.42 (d, J=14.6 Hz, 3H).

Example 2

(E)-{(5-chloro-benzo[b]thiophen-3-yl)-[2-(3,4-difluoro-phenyl)-vinylcarbamoyl]-methyl}-methyl-phosphinic acid ethyl ester (Cpd B5)

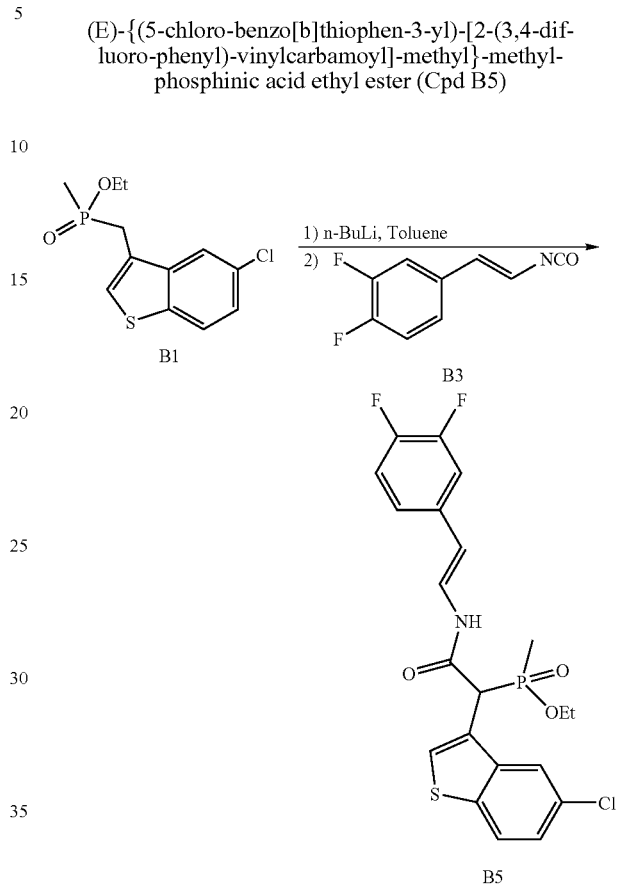

Into a 12 L 4-necked round-bottomed flask equipped with a mechanical stirrer, thermocouple and nitrogen inlet was added n-BuLi (2.5 M in hexanes, 560 mL, 1.40 mol, 1.28 equivalent) and toluene (1.5 L). The solution was cooled to −72° C. and Compound B1 (396.4 g, 93% Wt %, 1.28 mol) in toluene (2.8 L) was added drop wise over 1.5 hours. After stirring for 1 hour at −60 to −70° C., a cold solution (−66° C.) of Compound B3 (183.0 g, 95% Wt %, 0.96 mol, 0.75 Eq.) in toluene (1.75 L) was added slowly over a period of 2.5 hours at a temperature of −72° C. through a cannula. The reaction mixture was left overnight to warm to approximately 20° C. At a temperature of 20° C., the reaction mixture was quenched with 4 L of saturated NH$_4$Cl (to convert the bis-amide Compound B6 to the product Compound B5). The layers were separated and the organic layer was washed with water (5.0 L), and then exchanged under reduced pressure with EtOAc (5-7 L). Evaporation of the EtOAc yielded a yellow solid as a mixture of the desired product Compound B5, Compound B1 and polymeric impurities. Crystallization of the crude from ethyl acetate (1.7 L) and heptane (4.0 L) furnished Compound B5 (282 g. 62% yield based on the presence of Compound B6) as an off white solid.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. These publications are hereby incorporated by reference in their entirety into this application to describe more fully the state of the art to which this invention pertains.

What is claimed is:

1. A process for preparing a compound of Formula (I) and a salt thereof:

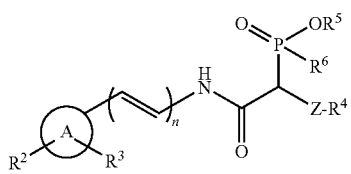

wherein

is selected from the group consisting of aryl, optionally substituted with $R^2$ and $R^3$;

$R^2$ is one to three substituents independently selected from the group consisting of $C_{1-4}$alkyl, methoxy, $C_{2-6}$alkoxy, —OCH$_2$—$C_{2-6}$alkenyl, NH$_2$, —NH($C_{1-6}$alkyl), —N($C_{1-6}$)dialkyl, aryl, heteroaryl, halogen, hydroxy, and nitro, wherein said $C_{1-4}$alkyl, $C_{2-6}$alkenyl and $C_{2-6}$alkoxy substituents of $R^2$ are optionally substituted with a substituent independently selected from the group consisting of —NR$^{11}$R$^{12}$, aryl, heteroaryl, one to three halogens and hydroxy;

$R^{11}$ and $R^{12}$ are substituents independently selected from the group consisting of hydrogen, $C_{1-6}$alkyl, and aryl; wherein said $C_{1-6}$alkyl substituent of $R^{11}$ or $R^{12}$ is optionally substituted with substituent selected from the group consisting of hydroxy, aryl, —C(=O)$C_{1-4}$-alkoxy, and —NR$^{15}$R$^{16}$;

$R^{15}$ and $R^{16}$ are substituents independently selected from the group consisting of hydrogen, $C_{1-6}$alkyl, and aryl, and said $R^{15}$ and $R^{16}$ are optionally taken together with the atoms to which they are attached to form a ring of five to seven members;

$R^3$ is one to three substituents independently selected from the group consisting of $C_{1-6}$alkyl, $C_{2-6}$alkenyl, $C_{1-6}$alkoxy, —OCH$_2$($C_{2-6}$)alkenyl, NH$_2$, —NH($C_{1-6}$alkyl), —N($C_{1-6}$)dialkyl, —NHC(=O)Cy, —N($C_{1-6}$alkyl)C(=O)Cy, —C(=O)$C_{1-4}$-alkoxy, —C(=O)NR$^{17}$R$^{18}$, —C(=O)NHcycloalkyl, —C(=O)N($C_{1-6}$alkyl)cycloalkyl, —C(=O)NHCy, —C(=O)N($C_{1-6}$alkyl)Cy, —C(=O)Cy, —OC(=O)NR$^{19}$R$^{20}$, halogen, hydroxy, nitro, cyano, aryl and aryloxy, wherein said $C_{1-6}$alkyl and $C_{1-6}$alkoxy are optionally substituted with one to three substituents independently selected from the group consisting of —NR$^{21}$R$^{22}$, —NHcycloalkyl, —N($C_{1-6}$alkyl)cycloalkyl, —NHCy, —N($C_{1-6}$alkyl)Cy, —NHC(O)—$C_{1-6}$alkyl-$C_{1-6}$alkoxy, aryl, heteroaryl, halogen, —C(=O)NR$^{23}$R$^{24}$, —OC(=O)NR$^{25}$R$^{26}$, —C(=O)($C_{1-4}$)alkoxy, and —C(=O)Cy, wherein each instance of said $C_{2-6}$alkenyl is optionally substituted on a terminal carbon with aryl or —C(=O)NR$^{27}$R$^{28}$, and wherein said aryl and cycloalkyl are optionally substituted with one to three substituents independently selected from $R^{14}$;

$R^{14}$ is independently hydrogen, $C_{1-6}$alkyl, $C_{1-6}$alkoxy, $C_{2-6}$alkenyl, $C_{1-6}$alkylthio, —NH$_2$, —NH($C_{1-6}$)alkyl, —N($C_{1-6}$)dialkyl, aryl, heteroaryl, aryloxy, heteroaryloxy, halogen, hydroxy, or nitro, and any one of the foregoing $C_{1-6}$alkyl- or $C_{1-6}$alkoxy-containing substituents of $R^{14}$ is optionally substituted on a terminal carbon atom with a substituent selected from —NR$^{29}$R$^{30}$, aryl, heteroaryl, one to three halogen atoms, or hydroxy;

$R^{17}$, $R^{18}$, $R^{19}$, $R^{20}$, $R^{21}$, $R^{22}$, $R^{23}$, $R^{24}$, $R^{25}$ and $R^{26}$ are substituents independently selected from the group consisting of hydrogen, $C_{1-6}$alkyl and aryl, wherein $C_{1-6}$alkyl and aryl are each optionally substituted with hydroxy, aryl, aryloxy, —C(=O)-aryl, —C(=O)$C_{1-4}$-alkoxy, NH$_2$, —NH($C_{1-6}$alkyl), or —N($C_{1-6}$)dialkyl; and said $R^{17}$ and $R^{18}$, $R^{19}$ and $R^{20}$, $R^{21}$ and $R^{22}$, $R^{23}$ and $R^{24}$ or $R^{25}$ and $R^{26}$ are optionally taken together with the atoms to which they are attached to form a ring of five to seven members;

$R^{27}$ and $R^{28}$ are independently hydrogen; $C_{1-6}$alkyl optionally substituted with hydroxy, aryl, —C(=O)$C_{1-4}$-alkoxy, NH$_2$, —NH($C_{1-6}$alkyl) or —N($C_{1-6}$)dialkyl; or aryl; and said $R^{27}$ and $R^{28}$ are optionally taken together with the atoms to which they are attached to form a ring of five to seven members;

$R^{29}$ and $R^{30}$ are independently hydrogen; $C_{1-6}$alkyl optionally substituted with hydroxy, aryl, —C(=O)$C_{1-4}$ alkoxy, NH$_2$, —NH($C_{1-6}$alkyl), or —N($C_{1-6}$)dialkyl; or aryl; and $R^{29}$ and $R^{30}$ are optionally taken together with the atoms to which they are attached to form a ring of five to seven members;

Cy is a heterocyclyl optionally substituted with a substituent selected from the group consisting of oxo, $C_{1-6}$alkyl, —$C_{1-6}$alkylC(=O)$C_{1-6}$alkyl, —$C_{1-6}$alkylC(=O)$C_{1-6}$alkoxy, —$C_{1-6}$alkyl-aryl, —$C_{1-6}$alkylC(=O)aryl, —C(=O)($C_{1-6}$)alkyl, —C(=O)($C_{1-6}$)alkoxy, —C(=O)aryl, —SO$_2$aryl, aryl, heteroaryl and heterocyclyl, wherein aryl and the aryl portion of —$C_{1-6}$alkylC(=O) aryl, —C(=O)aryl and —SO$_2$aryl are optionally substituted with one to three substituents independently selected from the group consisting of $C_{1-6}$alkyl, $C_{1-6}$alkoxy, halogen, hydroxy, NH$_2$, —NH($C_{1-6}$alkyl), and —N($C_{1-6}$)dialkyl; and wherein heterocyclyl is optionally substituted with aryl, one to three halogen atoms, or one to three oxo substituents; and, wherein heterocyclyl is optionally spiro-fused to said Cy;

$R^5$ is selected from the group consisting of hydrogen or $C_{1-3}$alkyl optionally substituted with NH$_2$, —NH($C_{1-6}$) alkyl, —N($C_{1-6}$)dialkyl, $C_{1-6}$alkylcarbonyloxy-, $C_{1-6}$alkoxycarbonyloxy-, $C_{1-6}$alkylcarbonylthio-, ($C_{1-6}$) alkylaminocarbonyl-, di($C_{1-6}$)alkylaminocarbonyl-, one to three halogens, or hydroxy; and said aryl is optionally substituted with $C_{1-6}$alkyl, $C_{1-6}$alkoxy, $C_{1-6}$alkylthio-, $C_{2-6}$alkenyl, NH$_2$, —NH($C_{1-6}$)alkyl, —N($C_{1-6}$)dialkyl, aryl, heteroaryl, aryloxy, heteroaryloxy, halogen, hydroxy, or nitro; alternatively, when $R^6$ is $C_{1-8}$alkoxy, said $R^5$ and $R^6$ are taken together with the atoms to which they are attached to form a 5-8 membered monocyclic ring, provided that $R^5$ is other than $C_{1-3}$alkyl substituted with di($C_{1-6}$)alkylamino-carbonyl- when ring system A is 3,4-difluoro-phenyl, n is 1, $R^6$ is OH, and Z—$R^4$ is 5-chloro-benzothiophen-3-yl; and provided that $R^5$ is other than $C_{1-3}$alkyl substituted with $C_{1-6}$alkylcarbon-ylthio- when ring system A is 3,4-difluoro-phenyl, n is 1, $R^6$ is $CH_3$, and Z—$R^4$ is 5-chloro-benzothiophen-3-yl;

$R^6$ is selected from the group consisting of $C_{1-6}$alkyl, $C_{1-8}$alkoxy, heteroaryl, aryl, and hydroxy; wherein $C_{1-6}$alkyl is optionally substituted on a terminal carbon atom with a substituent selected from $C_{1-3}$alkoxy, aryl, or hydroxy;

and $C_{1-8}$alkoxy is optionally substituted on a terminal carbon atom with a substituent independently selected from the group consisting of $C_{1-6}$alkylcarbonyloxy- and di($C_{1-6}$)alkylaminocarbonyl-; and wherein heteroaryl and aryl are optionally substituted with one to three substituents independently selected from the group consisting of aryl, hydroxy, $C_{1-6}$alkoxy, and halogen;

Z is a bicyclic aryl or bicyclic heteroaryl; wherein aryl and heteroaryl are optionally substituted with the group $R^4$;

$R^4$ is one to three substituents selected from the group consisting of $C_{1-6}$alkyl, $C_{2-6}$alkenyl, $C_{1-6}$alkoxy, aryl$(C_{2-6})$alkenyl, halogen, —C(=O)Cy, —C(=O)NR$^{31}$R$^{32}$, aryl, —CO$_2$H, oxo and cyano, wherein said $C_{1-6}$alkyl, $C_{2-6}$alkenyl and $C_{1-6}$alkoxy are optionally substituted with a substituent independently selected from the group consisting of —NR$^{33}$R$^{34}$, aryl, one to three halogen atoms and hydroxy, and wherein said aryl is optionally substituted with a substituent independently selected from the group consisting of hydrogen, $C_{1-6}$alkyl, $C_{1-6}$alkoxy, aryl, halogen, hydroxy, and nitro; and $R^{31}$, $R^{32}$, $R^{33}$ and $R^{34}$ are substituents independently selected from the group consisting of hydrogen, $C_{1-6}$alkyl, and aryl, wherein alkyl is optionally substituted with hydroxy, aryl, —C(=O)$C_{1-4}$alkoxy, NH$_2$, NH($C_{1-6}$alkyl), or —N($C_{1-6}$)dialkyl; and said $R^{31}$ and $R^{32}$ or $R^{33}$ and $R^{34}$ are optionally taken together with the atoms to which they are attached to form a ring of five to seven members;

comprising the steps of:

Step 1. reacting a Compound A1 (wherein $R^5$ is $C_{1-3}$alkyl) with a Compound A2, wherein Compound A1 and Compound A2 are present in a first ratio, in toluene, to provide a Compound A3 (wherein $R^5$ is $C_{1-3}$alkyl), representative of a compound of Formula (I):

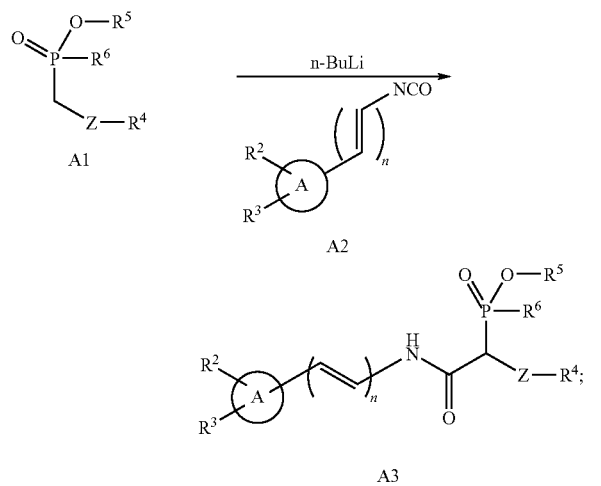

wherein in the first ratio, the amount of Compound A1 exceeds the amount of Compound A2 by about 0.2 equivalents; and Step 2. reacting the Compound A3 (wherein $R^5$ is $C_{1-3}$alkyl) in the presence of TMSBr, in acetonitrile and optionally present pyridine, wherein TMSBr and Compound A3 are in a second ratio, and wherein TMSBr and pyridine, when pyridine is present, are in a third ratio, to provide a Compound A4 (wherein $R^5$ is hydrogen), representative of a compound of Formula (I):

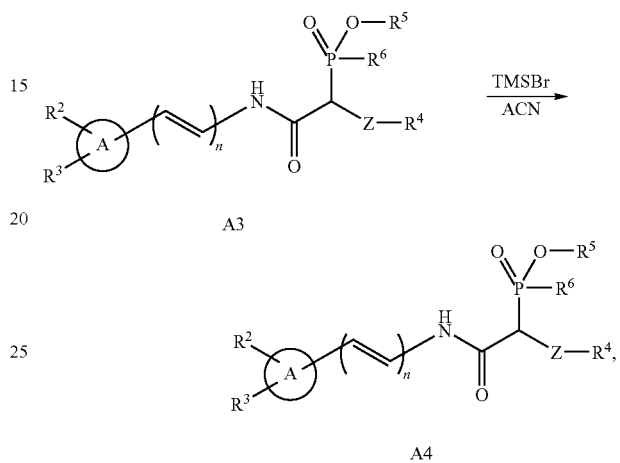

wherein the second ratio of TMSBr:Compound A3 is in a range of about 2.5:1 to about 2:1; and wherein the third ratio of TMSBr:pyridine, when pyridine is present, is in a range of from about 1:1 to about 1:2.

2. The process of claim 1, further comprising the step of:

Step 3. reacting the Compound A4 (wherein $R^5$ is hydrogen) with a cationic salt-forming compound, in a solvent mixture, wherein the solvents in the mixture are in a fourth ratio, to provide a Compound A5 as a salt, representative of a compound of Formula (I), wherein the salt is obtained by direct crystallization:

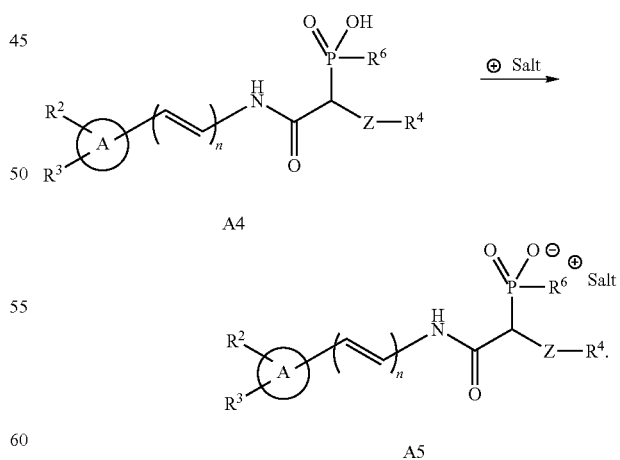

3. The process of claim 2, wherein an amount of Compound A1 is in a range of from about 1.2 equivalents to about 1 equivalent and an amount of Compound A2 is in a range of from about 1 equivalent to about 0.8 equivalents according to said first ratio.

4. The process of claim 1, wherein the ratio of TMSBr:Compound A3 is in a range of about 2.5:1 to about 2:1, according to said second ratio, and wherein the third ratio of TMSBr:pyridine is in a range of about 1:1 to about 1:2.

5. The process of claim 1, wherein in the third ratio of TMSBr:pyridine is about 1:2.

6. The process of claim 1, wherein the ratio of TMSBr:Compound A3 is in a range of about 2.5:1 to about 2:1, according to said second ratio, wherein pyridine is not present.

7. The process of claim 2, wherein the salt of the compound of claim 1 is a choline salt precipitated from a solvent mixture of MeOH and EtOAc, wherein the solvents are in said fourth ratio of about 1:3 MeOH:EtOAc.

8. The process of claim 1, wherein the compound is selected from the group consisting of:
[(5-chloro-1-methyl-1H-indol-3-yl)-(naphthalen-2-ylcarbamoyl)-methyl]-methyl-phosphinic acid,
(E)-{(5-chloro-benzo[b]thiophen-3-yl)-[2-(3,4-difluorophenyl)-vinylcarbamoyl]-methyl}-phosphonic acid,
[(5-chloro-1-methyl-1H-indol-3-yl)-(naphthalen-2-ylcarbamoyl)-methyl]-phosphonic acid,
(E)-{(5-chloro-1-methyl-1H-indol-3-yl)-[2-(4-fluorophenyl)-vinylcarbamoyl]-methyl}-phosphonic acid,
[(5-methyl-benzo[b]thiophen-3-yl)-(naphthalen-2-ylcarbamoyl)-methyl]-phosphonic acid,
(E)-{(5-chloro-1-methyl-1H-indol-3-yl)-[2-(3-fluorophenyl)-vinylcarbamoyl]-methyl}-methyl-phosphinic acid,
(E)-{(5-chloro-1-methyl-1H-indol-3-yl)-[2-(3,4-difluorophenyl)-vinylcarbamoyl]-methyl}-methyl-phosphinic acid,
[(4-{[1-(naphthalene-2-carbonyl)-piperidine-4-carbonyl]-amino}-naphthalen-2-ylcarbamoylnaphthalen-1-yl-methyl]-phosphonic acid,
[(5-chloro-benzo[b]thiophen-3-yl)-(naphthalen-2-ylcarbamoyl)-methyl]-phosphonic acid,
[(5-fluoro-benzo[b]thiophen-3-yl)-(naphthalen-2-ylcarbamoyl)-methyl]-phosphonic acid,
[(5-fluoro-1-methyl-1H-indol-3-yl)-(naphthalen-2-ylcarbamoyl)-methyl]-phosphonic acid,
(E)-[[2-(4-amino-phenyl)-vinylcarbamoyl]-(5-chloro-benzo[b]thiophen-3-yl)-methyl]-phosphonic acid,
[(5-bromo-1-methyl-1H-indol-3-yl)-(naphthalen-2-ylcarbamoyl)-methyl]-phosphonic acid,
(E)-[(5-chloro-benzo[b]thiophen-3-yl)-styrylcarbamoyl-methyl]-methyl-phosphinic acid,
(E)-{(5-chloro-benzo[b]thiophen-3-yl)-[2-(3-fluoro-phenyl)-vinylcarbamoyl]-methyl}-methyl-phosphinic acid,
(E)-{(5-chloro-benzo[b]thiophen-3-yl)-[2-(3,4,5-trifluoro-phenyl)-vinylcarbamoyl]-methyl}-methyl-phosphinic acid,
(E)-{(5-chloro-benzo[b]thiophen-3-yl)-[2-(3,4-difluorophenyl)-vinylcarbamoyl]-methyl}-methyl-phosphinic acid,
(E)-[(5-chloro-benzo[b]thiophen-3-yl)-styrylcarbamoyl-methyl]-phosphonic acid,
(E)-{(5-chloro-benzo[b]thiophen-3-yl)-[2-(4-fluoro-phenyl)-vinylcarbamoyl]-methyl}-phosphonic acid,
[(5-chloro-benzo[b]thiophen-3-yl)-(naphthalen-2-ylcarbamoyl)-methyl]-methyl-phosphinic acid,
(E)-{(5-chloro-benzo[b]thiophen-3-yl)-[2-(2-fluoro-phenyl)-vinylcarbamoyl]-methyl}-methyl-phosphinic acid,
[(1-methyl-1H-indol-3-yl)-(naphthalen-2-ylcarbamoyl)-methyl]-phosphonic acid,
[(5-bromo-benzo[b]thiophen-3-yl)-(naphthalen-2-ylcarbamoyl)-methyl]-phosphonic acid,
(E)-{(5-chloro-benzo[b]thiophen-3-yl)-[2-(4-fluoro-phenyl)-vinylcarbamoyl]-methyl}-methyl-phosphinic acid,
[benzo[b]thiophen-3-yl-(naphthalen-2-ylcarbamoyl)-methyl]-phosphonic acid,
{(naphthalen-2-ylcarbamoyl)-[1-(3-phenyl-allyl)-1H-indol-3-yl]-methyl}-phosphonic acid,
[(5-chloro-benzo[b]thiophen-3-yl)-(naphthalen-2-ylcarbamoyl)-methyl]-ethyl-phosphinic acid,
(E)-{(5-chloro-benzo[b]thiophen-3-yl)-[2-(3,4-difluorophenyl)-vinylcarbamoyl]-methyl}-ethyl-phosphinic acid,
[naphthalen-1-yl-(naphthalen-2-ylcarbamoyl)methyl]-phosphonic acid,
methyl-{(naphthalen-2-ylcarbamoyl)-[2-(4-phenyl-piperidine-1-carbonyl)-benzo[b]thiophen-3-yl]-methyl}-phosphinic acid,
methyl-[naphthalen-1-yl-(naphthalen-2-ylcarbamoyl)-methyl]-phosphinic acid,
[(5-chloro-benzo[b]thiophen-3-yl)-(naphthalen-2-ylcarbamoyl)-methyl]-(3-methoxy-propyl)-phosphinic acid,
[{2-[4-(4-methoxy-phenyl)-piperidine-1-carbonyl]-benzo[b]thiophen-3-yl]-(naphthalen-2-ylcarbamoyl)-methyl}-methyl-phosphinic acid,
[(5-chloro-benzo[b]thiophen-3-yl)-(naphthalen-2-ylcarbamoyl)-methyl]-phenethyl-phosphinic acid,
(E)-(naphthalen-1-yl-styrylcarbamoyl-methyl)phosphonic acid,
(E)-{(5-chloro-benzo[b]thiophen-3-yl)-[2-(4-methoxy-phenyl)-vinylcarbamoyl]-methyl}-phosphonic acid,
(3-benzo[1,3]dioxol-5-yl-propyl)-[(5-chloro-benzo[b]thiophen-3-yl)-(naphthalen-2-ylcarbamoyl)-methyl]-phosphinic acid,
[(5-chloro-benzo[b]thiophen-3-yl)-(naphthalen-2-ylcarbamoyl)-methyl]-(3-naphthalen-1-yl-propyl)-phosphinic acid,
[{2-[4-(benzyloxycarbonyl)-piperazin-1-ylcarbonyl]-benzothiophen-3-yl}-(naphthalen-2-ylcarbamoyl)-methyl]-methyl-phosphinic acid,
(E)-[(5-chloro-benzo[b]thiophen-3-yl)-(2-p-tolyl-vinylcarbamoyl)-methyl]-phosphonic acid,
[(5-chloro-benzo[b]thiophen-3-yl)-(naphthalen-2-ylcarbamoyl)-methyl]-[3-(4-hydroxy-phenyl)-propyl]-phosphinic acid,
({3-[(1-benzoyl-piperidin-4-ylamino)-methyl]-naphthalen-2-ylcarbamoyl}-naphthalen-1-yl-methylyphosphonic acid,
({3-[methyl-(4-phenyl-cyclohex-3-enyl)-carbamoyl]-naphthalen-2-ylcarbamoyl}-naphthalen-1-yl-methylyphosphonic acid,
[{2-[4-(4-fluoro-phenyl)-piperidine-1-carbonyl]-benzo[b]thiophen-3-yl]-(naphthalen-2-ylcarbamoyl)-methyl}-methyl-phosphinic acid,
[(5-chloro-benzo[b]thiophen-3-yl)-(naphthalen-2-ylcarbamoyl)-methyl]-(3-phenyl-propyl)-phosphinic acid,
(E)-{(5-chloro-benzo[b]thiophen-3-yl)-[2-(3,4-dimethoxy-phenyl)-vinylcarbamoyl]-methyl}-phosphonic acid,
[(5-chloro-benzo[b]thiophen-3-yl)-(naphthalen-2-ylcarbamoyl)-methyl]-(4-phenyl-butyl)-phosphinic acid,
[(6-chloro-1-methyl-1H-indol-3-yl)-(naphthalen-2-ylcarbamoyl)-methyl]-phosphonic acid,
[(5-chloro-benzo[b]thiophen-3-yl)-(naphthalen-2-ylcarbamoyl)-methyl]-[3-(4-methoxy-phenyl)-propyl]-phosphinic acid,
{naphthalen-1-yl-[3-(3-phenethyl-pyrrolidine-1-carbonyl)-naphthalen-2-ylcarbamoyl]-methyl]-phosphonic acid,

[(5-carboxy-1-methyl-1H-indol-3-yl)-(naphthalen-2-yl-carbamoyl)-methyl]-phosphonic acid,
[(7-chloro-1-methyl-1H-indol-3-yl)-(naphthalen-2-ylcarbamoyl)-methyl]-phosphonic acid,
({3-[4-(6-chloro-2-oxo-2,3-dihydro-benzoimidazol-1-yl)-piperidine-1-carbonyl]-naphthalen-2-ylcarbamoyl}-naphthalen-1-yl-methyl)-phosphonic acid,
[(biphenyl-4-ylcarbamoyl)-naphthalen-1-yl-methyl]-phosphonic acid,
[(1-cyclopropylmethyl-1H-indol-3-yl)-(naphthalen-2-yl-carbamoyl)-methyl]-phosphonic acid,
[(4-chloro-1-methyl-1H-indol-3-yl)-(naphthalen-2-ylcarbamoyl)-methyl]-phosphonic acid,
[(5-cyano-1-methyl-1H-indol-3-yl)-(naphthalen-2-ylcarbamoyl)-methyl]-phosphonic acid,
(E)-{(5-chloro-benzo[b]thiophen-3-yl)-[2-(4-hydroxy-phenyl)-vinylcarbamoyl]-methyl}-phosphonic acid,
[(6-bromo-naphthalen-2-ylcarbamoyl)-(5-chloro-benzo[b]thiophen-3-yl)-methyl]-phosphonic acid,
[(1H-indol-3-yl)-(naphthalen-2-ylcarbamoyl)-methyl]-phosphonic acid,
[(3-cyclohexylaminomethyl-naphthalen-2-ylcarbamoyl)-naphthalen-1-yl-methyl]-phosphonic acid,
[(5-phenyl-benzo[b]thiophen-3-yl)-(naphthalen-2-ylcarbamoyl)-methyl]-phosphonic acid,
[(3-benzylcarbamoyloxymethyl-naphthalen-2-ylcarbamoyl)-naphthalen-1-yl-methyl]-phosphonic acid,
{naphthalen-1-yl-[3-(3-pyridin-4-yl-pyrrolidine-1-carbonyl)-naphthalen-2-ylcarbamoyl]-methyl}-phosphonic acid,
[(5-methoxy-1-methyl-1H-indol-3-yl)-(naphthalen-2-yl-carbamoyl)-methyl]-phosphonic acid,
3-(2-naphthalen-1-yl-2-phosphono-acetylamino)-naphthalene-2-carboxylic acid methyl ester,
[(6-bromo-benzo[b]thiophen-3-yl)-(naphthalen-2-ylcarbamoyl)-methyl]-phosphonic acid,
[(1-isopropyl-1H-indol-3-yl)-(naphthalen-2-ylcarbamoyl)-methyl]-phosphonic acid,
(E)-{(5-chloro-benzo[b]thiophen-3-yl)-[2-(4-chloro-phenyl)-vinylcarbamoyl]-methyl}-methyl-phosphinic acid,
(E)-{(5-chloro-benzo[b]thiophen-3-yl)-[2-(4-trifluoromethyl-phenyl)-vinylcarbamoyl]-methyl}-phosphonic acid,
[(naphthalen-2-ylcarbamoyl)-(1-phenyl-1H-indol-3-yl)methyl]-phosphonic acid,
({3-[4-(1H-indol-3-yl)-piperidine-1-carbonyl]-naphthalen-2-ylcarbamoyl}-naphthalen-1-yl-methyl)-phosphonic acid,
[(5-chloro-1,1-dioxo-1H-benzo[b]thiophen-3-yl)-(naphthalen-2-ylcarbamoyl)-methyl]-phosphonic acid,
{naphthalen-1-yl-[3-(3-phenyl-pyrrolidine-1-carbonyl)-naphthalen-2-ylcarbamoyl]-methyl}-phosphonic acid,
[(5-chloro-benzo[b]thiophen-3-yl)-(naphthalen-2-ylcarbamoyl)-methyl]-phenyl-phosphinic acid,
({3-[(3-methyl-cyclohexylamino)-methyl]-naphthalen-2-ylcarbamoyl}-naphthalen-1-yl-methylphosphonic acid,
{[3-(cyclopentyl-methyl-carbamoyl)-naphthalen-2-ylcarbamoyl]-naphthalen-1-yl-methyl}-phosphonic acid,
({3-[(5-methoxycarbonyl)-pent-1-ylaminomethyl]-naphthalen-2-ylcarbamoyl}-naphthalen-1-yl-methylyphosphonic acid,
(naphthalen-1-yl-{3-[4-(2-oxo-2,3-dihydro-benzoimidazol-1-yl)-piperidine-1-carbonyl]-naphthalen-2-ylcarbamoyl}-methyl)-phosphonic acid,
[naphthalen-1-yl-(3-phenylcarbamoyloxymethyl-naphthalen-2-ylcarbamoyl)-methyl]-phosphonic acid,
[naphthalen-1-yl-(3-phenylcarbamoyloxy-naphthalen-2-yl-carbamoyl)-methyl]-phosphonic acid,
{naphthalen-1-yl-[3-(4-phenoxy-phenylcarbamoyloxymethyl)-naphthalen-2-ylcarbamoyl]-methyl}-phosphonic acid,
[[5-(4-fluoro-phenyl)-1-methyl-1H-indol-3-yl]-(naphthalen-2-ylcarbamoyl)-methyl]-phosphonic acid,
[(4-bromo-benzo[b]thiophen-3-yl)-(naphthalen-2-ylcarbamoyl)-methyl]-phosphonic acid,
{[3-(4-benzotriazol-1-yl-piperidine-1-carbonyl)-naphthalen-2-ylcarbamoyl]-naphthalen-1-yl-methyl}-phosphonic acid,
{naphthalen-1-yl-[3-(4-phenyl-piperidine-1-carbonyl)-naphthalen-2-ylcarbamoyl]-methyl}-phosphonic acid,
{[3-({methyl-[1-(naphthalene-2-carbonyl)-piperidin-4-yl]-amino}-methyl)-naphthalen-2-ylcarbamoyl]-naphthalen-1-yl-methyl}-phosphonic acid,
{[3-(3-benzenesulfonyl-pyrrolidine-1-carbonyl)-naphthalen-2-ylcarbamoyl]-naphthalen-1-yl-methyl}-phosphonic acid,
{naphthalen-1-yl-[3-(4-oxo-1-phenyl-1,3,8-triaza-spiro[4.5]decane-8-carbonyl)-naphthalen-2-ylcarbamoyl]-methyl}-phosphonic acid,
{naphthalen-1-yl-[3-(naphthalen-2-ylcarbamoyloxymethyl)-naphthalen-2-ylcarbamoyl]-methyl}-phosphonic acid,
[(9H-fluoren-3-ylcarbamoyl)-naphthalen-1-yl-methyl]-phosphonic acid,
{[3-(benzylamino-methyl)-naphthalen-2-ylcarbamoyl]-naphthalen-1-yl-methyl}-phosphonic acid,
[(3-hydroxy-naphthalen-2-ylcarbamoyl)-naphthalen-1-yl-methyl]-phosphonic acid,
{[3-(2-benzylcarbamoyl-vinyl)-naphthalen-2-ylcarbamoyl]-naphthalen-1-yl-methyl}-phosphonic acid,
{naphthalen-1-yl-[3-(5-phenyl-pentylamino)-naphthalen-2-ylcarbamoyl]-methyl}-phosphonic acid,
{[3-(benzyl-methyl-carbamoyl)-naphthalen-2-ylcarbamoyl]-naphthalen-1-yl-methyl}-phosphonic acid,
{[3-({[3-(5H-dibenzo[a,d]cyclohepten-5-yl)-propyl]-methyl-amino}-methyl)-naphthalen-2-ylcarbamoyl]-naphthalen-1-yl-methyl}-phosphonic acid,
{[3-(4-benzothiazol-2-yl-piperidine-1-carbonyl)-naphthalen-2-ylcarbamoyl]-naphthalen-1-yl-methyl}-phosphonic acid,
(naphthalen-1-yl-{1-[2-oxo-2-(4-phenyl-piperidin-1-yl)-ethoxy]-naphthalen-2-ylcarbamoyl}-methyl)-phosphonic acid,
[(3-{[2-(3,4-dimethoxy-phenyl)-ethyl]-methyl-carbamoyl}-naphthalen-2-ylcarbamoylnaphthalen-1-yl-methyl]-phosphonic acid,
[(1-methyl-1H-pyrrolo[2,3-b]pyridin-3-yl)-(naphthalen-2-ylcarbamoyl)-methyl]-phosphonic acid,
({3-[(4-hydroxy-cyclohexylamino)-methyl]-naphthalen-2-ylcarbamoyl}-naphthalen-1-yl-methylyphosphonic acid,
[(2-carboxy-benzo[b]thiophen-3-yl)-(naphthalen-2-ylcarbamoyl)-methyl]-methyl-phosphinic acid,
[(3-benzylcarbamoyl-naphthalen-2-ylcarbamoyl)-naphthalen-1-yl-methyl]-phosphonic acid,
{naphthalen-1-yl-[3-(3-phenyl-allyloxy)-naphthalen-2-ylcarbamoyl]-methyl}-phosphonic acid,
[(3-benzyloxy-naphthalen-2-ylcarbamoyl)-naphthalen-1-yl-methyl]-phosphonic acid,
[(3-methoxycarbonylmethoxy-naphthalen-2-ylcarbamoyl)-naphthalen-1-yl-methyl]-phosphonic acid,
[(3-cyclopentylaminomethyl-naphthalen-2-ylcarbamoyl)-naphthalen-1-yl-methyl]-phosphonic acid,

[1-(5-chloro-benzo[b]thiophen-3-yl)-1-(naphthalen-2-yl-carbamoyl)-ethyl]-phosphonic acid,
({3-[(methyl-phenethyl-amino)-methyl]-naphthalen-2-yl-carbamoyl}-naphthalen-1-yl-methylyphosphonic acid,
[(2-benzylcarbamoyl-benzo[b]thiophen-3-yl)-(naphthalen-2-ylcarbamoyl)-methyl]-methyl-phosphinic acid,
[(naphthalen-2-ylcarbamoyl)-(1-phenyl-1H-indol-3-yl)-methyl]-phosphonic acid,
(naphthalen-1-yl-{1-[(3-phenyl-propylcarbamoyl)-methoxy]-naphthalen-2-ylcarbamoyl}-methyl)-phosphonic acid,
{naphthalen-1-yl-[3-(2-phenyl-pyrrolidine-1-carbonyl)-naphthalen-2-ylcarbamoyl]-methyl}-phosphonic acid,
[(3-amino-naphthalen-2-ylcarbamoyl)-naphthalen-1-yl-methyl]-phosphonic acid,
({3-[(5-hydroxy-pentylamino)-methyl]-naphthalen-2-yl-carbamoyl}-naphthalen-1-yl-methyloxy-phosphonic acid,
{[(1-methoxycarbonylmethoxy-naphthalen-2-yl)carbamoyl]-naphthalen-1-yl-methyl}-phosphonic acid,
[naphthalen-1-yl-(3-phenoxy-phenylcarbamoyl)-methyl]-phosphonic acid,
{[(3-isopropyloxycarbonyl-naphthalen-2-yl)carbamoyl]-naphthalen-1-yl-methyl}-phosphonic acid,
[(benzo[b]thiophen-2-yl)-(naphthalen-2-ylcarbamoyl)-methyl]-phosphonic acid,
[(3-{[1-(naphthalene-2-carbonyl)-piperidine-4-carbonyl]-amino}-naphthalen-2-ylcarbamoylynaphthalen-1-yl-methyl]-phosphonic acid,
({3-[(benzyl-methyl-amino)-methyl]-naphthalen-2-ylcarbamoyl}-naphthalen-1-yl-methyloxy-phosphonic acid,
{(naphthalen-2-ylcarbamoyl)-[6-(4-pentyl-phenyl)-benzo[b]thiophen-3-yl]-methyl}-phosphonic acid,
(E)-{(5-chloro-benzo[b]thiophen-3-yl)-[2-(2-methoxy-phenyl)-vinylcarbamoyl]-methyl}-methyl-phosphinic acid,
(E)-{(5-chloro-benzo[b]thiophen-3-yl)-[2-(2-nitro-phenyl)-vinylcarbamoyl]-methyl}-methyl-phosphinic acid,
(E)-{(5-chloro-benzo[b]thiophen-3-yl)-[2-(2-methylcarbonyloxy-phenyl)-vinylcarbamoyl]-methyl}-methyl-phosphinic acid,
(E)-{(5-chloro-benzo[b]thiophen-3-yl)-[2-(2-hydroxy-phenyl)-vinylcarbamoyl]-methyl}-methyl-phosphinic acid,
(E)-[[2-(2-amino-phenyl)-vinylcarbamoyl]-(5-chloro-benzo[b]thiophen-3-yl)-methyl]-methyl-phosphinic acid,
(E)-{(5-chloro-benzo[b]thiophen-3-yl)-[2-(3-trifluoromethyl-phenyl)-vinylcarbamoyl]-methyl}-methyl-phosphinic acid,
(E)-{(5-chloro-benzo[b]thiophen-3-yl)-[2-(3-trifluoromethoxy-phenyl)-vinylcarbamoyl]-methyl}-methyl-phosphinic acid,
(E)-{(5-chloro-benzo[b]thiophen-3-yl)-[2-(3-methoxy-phenyl)-vinylcarbamoyl]-methyl}-methyl-phosphinic acid,
(E)-[(5-chloro-benzo[b]thiophen-3-yl)-(2-o-tolyl-vinylcarbamoyl)-methyl]-methyl-phosphinic acid,
(E)-{(5-chloro-benzo[b]thiophen-3-yl)-[2-(2,6-difluoro-phenyl)-vinylcarbamoyl]-methyl}-methyl-phosphinic acid,
(E)-{(5-chloro-benzo[b]thiophen-3-yl)-[2-(4-cyano-phenyl)-vinylcarbamoyl]-methyl}-methyl-phosphinic acid,
(E)-{(5-chloro-benzo[b]thiophen-3-yl)-[2-(2-ureido-phenyl)-vinylcarbamoyl]-methyl}-methyl-phosphinic acid,
(E)-{(5-chloro-benzo[b]thiophen-3-yl)-[2-(2-carbamoyl-carbamoylamino-phenyl)-vinylcarbamoyl]-methyl}-methyl-phosphinic acid,
(E)-{(5-chloro-benzo[b]thiophen-3-yl)-[2-(2-chloro-phenyl)-vinylcarbamoyl]-methyl}-methyl-phosphinic acid,
(E)-{(5-chloro-benzo[b]thiophen-3-yl)-[2-(3-chloro-phenyl)-vinylcarbamoyl]-methyl}-methyl-phosphinic acid,
(E)-{(5-chloro-benzo[b]thiophen-3-yl)-[2-(3,5-difluoro-phenyl)-vinylcarbamoyl]-methyl}-methyl-phosphinic acid,
(E)-{(5-chloro-benzo[b]thiophen-3-yl)-[2-(2,3-difluoro-phenyl)-vinylcarbamoyl]-methyl}-methyl-phosphinic acid,
(E)-[[2-(2-bromo-phenyl)-vinylcarbamoyl]-(5-chloro-benzo[b]thiophen-3-yl)-methyl]-methyl-phosphinic acid,
(E)-{(5-chloro-benzo[b]thiophen-3-yl)-[2-(2,3-dimethoxy-phenyl)-vinylcarbamoyl]-methyl}-methyl-phosphinic acid,
(E)-{(5-chloro-benzo[b]thiophen-3-yl)-[2-(3-nitro-phenyl)-vinylcarbamoyl]-methyl}-methyl-phosphinic acid,
(E)-[[2-(3-bromo-phenyl)-vinylcarbamoyl]-(5-chloro-benzo[b]thiophen-3-yl)-methyl]-methyl-phosphinic acid,
(E)-{(5-chloro-benzo[b]thiophen-3-yl)-[2-(3,5-dimethoxy-phenyl)-vinylcarbamoyl]-methyl}-methyl-phosphinic acid,
(E)-{(5-chloro-benzo[b]thiophen-3-yl)-[2-(2,5-difluoro-phenyl)-vinylcarbamoyl]-methyl}-methyl-phosphinic acid,
(E)-{(5-chloro-benzo[b]thiophen-3-yl)-[2-(3,5-dichloro-phenyl)-vinylcarbamoyl]-methyl}-methyl-phosphinic acid,
(E)-{(5-chloro-benzo[b]thiophen-3-yl)-[2-(2,4-difluoro-phenyl)-vinylcarbamoyl]-methyl}-methyl-phosphinic acid,
(E)-[[2-(3-amino-phenyl)-vinylcarbamoyl]-(5-chloro-benzo[b]thiophen-3-yl)-methyl]-methyl-phosphinic acid,
(E)-2-(styrylcarbamoyl-naphthalen-1-yl-methyl)-5,5-dimethyl-1,3,2-dioxaphosphorinane 2-oxide,
(E)-(styrylcarbamoyl)-naphthalen-1-yl-methyl-phosphonic acid (3-methoxy-propyl)ester,
(E)-(styrylcarbamoyl)-naphthalen-1-yl-methyl-phosphonic acid bis-(3-methoxy-propyl)ester,
(E)-(styrylcarbamoyl)-naphthalen-1-yl-methyl-phosphonic acid mono-(2-benzo[1,3]dioxol-2-yl-ethyl)ester,
(E)-(styrylcarbamoyl)-naphthalen-1-yl-methyl-phosphonic acid (tert-butylcarbonyloxymethyl)ester,
(E)-2-(styrylcarbamoyl-naphthalen-1-yl-methyl)-1,3,2-dioxaphosphorinane 2-oxide,
(E)-(styrylcarbamoyl)-naphthalen-1-yl-methyl-phosphonic acid bis-(2-dimethylamino-ethyl)ester,
(E)-(styrylcarbamoyl)-naphthalen-1-yl-methyl-phosphonic acid bis-(diethylaminocarbonylmethyl)ester,
(E)-(styrylcarbamoyl)-naphthalen-1-yl-methyl-phosphonic acid bis-(2-tert-butylcarbonylthioethyl)ester,
(E)-{(5-chloro-benzo[b]thiophen-3-yl)-[2-(3,4-difluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3,4-difluoro-phenyl)-vinylcarbamoyl]-methyl}-methyl-phosphinic acid (2-dimethylaminoethyl)ester,
(E)-{(5-chloro-benzo[b]thiophen-3-yl)-[2-(3,4-difluoro-phenyl)-vinylcarbamoyl]-methyl}-methyl-phosphinic acid (2-aminoethyl)ester,
(E)-{(5-chloro-benzo[b]thiophen-3-yl)-[2-(3,4-difluoro-phenyl)-vinylcarbamoyl]-methyl}-methyl-phosphinic acid (2-diethylamino-2-oxo-ethyl)ester, (E)-{(5-chloro-benzo[b]thiophen-3-yl)-[2-(3,4-difluoro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3,4-difluoro-phenyl)-vinylcarbamoyl]-methyl}-phosphonic acid (tert-butylcarbonyloxymethyl)ester,
(E)-{(5-chloro-benzo[b]thiophen-3-yl)-[2-(3,4-difluoro-phenyl)-vinylcarbamoyl]-methyl}-phosphonic acid bis-(2-diethylamino-2-oxo-ethyl)ester,
(E)-2-{(5-chloro-benzo[b]thiophen-3-yl)-[2-(3,4-difluoro-phenyl)-vinylcarbamoyl]-methyl}-1,3,2-dioxaphosphorinane 2-oxide,
(E)-{(5-chloro-benzo[b]thiophen-3-yl)-[2-(3,4-difluoro-phenyl)-vinylcarbamoyl]-methyl}-phosphonic acid [(methylcarbonyloxy)-methyl]ester,
(E)-{(5-chloro-benzo[b]thiophen-3-yl)-[2-(3,4-difluoro-phenyl)-vinylcarbamoyl]-methyl}-phosphonic acid [(isopropoxycarbonyloxy)-methyl]ester,
(E)-{(5-chloro-benzo[b]thiophen-3-yl)-[2-(2-methoxy-phenyl)-vinylcarbamoyl]-methyl}-phosphonic acid,
(E)-[(5-chloro-benzo[b]thiophen-3-yl)-(2-pyridin-2-yl-vinylcarbamoyl)-methyl]-phosphonic acid,
(E)-{(5-chloro-benzo[b]thiophen-3-yl)-[2-(3-trifluoromethoxy-phenyl)-vinylcarbamoyl]-methyl}-phosphonic acid,
(E)-{(5-chloro-benzo[b]thiophen-3-yl)-[2-(3-methoxy-phenyl)-vinylcarbamoyl]-methyl}-phosphonic acid,
(E)-{(5-chloro-benzo[b]thiophen-3-yl)-[2-(2,6-difluoro-phenyl)-vinylcarbamoyl]-methyl}-phosphonic acid,
(E)-{(5-chloro-benzo[b]thiophen-3-yl)-[2-(2-chloro-phenyl)-vinylcarbamoyl]-methyl}-phosphonic acid,
(E)-{(5-chloro-benzo[b]thiophen-3-yl)-[2-(3-chloro-phenyl)-vinylcarbamoyl]-methyl}-phosphonic acid,
(E)-{(5-chloro-benzo[b]thiophen-3-yl)-[2-(3,5-difluoro-phenyl)-vinylcarbamoyl]-methyl}-phosphonic acid,
(E)-{(5-chloro-benzo[b]thiophen-3-yl)-[2-(2,3-difluoro-phenyl)-vinylcarbamoyl]-methyl}-phosphonic acid,
(E)-{(5-chloro-benzo[b]thiophen-3-yl)-[2-(2-bromo-phenyl)-vinylcarbamoyl]-methyl}-phosphonic acid,
(E)-{(5-chloro-benzo[b]thiophen-3-yl)-[2-(2,3-dimethoxy-phenyl)-vinylcarbamoyl]-methyl}-phosphonic acid,
(E)-{(5-chloro-benzo[b]thiophen-3-yl)-[2-(3-nitro-phenyl)-vinylcarbamoyl]-methyl}-phosphonic acid,
(E)-{(5-chloro-benzo[b]thiophen-3-yl)-[2-(3-bromo-phenyl)-vinylcarbamoyl]-methyl}-phosphonic acid,
(E)-{(5-chloro-benzo[b]thiophen-3-yl)-[2-(3,5-dimethoxy-phenyl)-vinylcarbamoyl]-methyl}-phosphonic acid,
(E)-{(5-chloro-benzo[b]thiophen-3-yl)-[2-(2,5-difluoro-phenyl)-vinylcarbamoyl]-methyl}-phosphonic acid,
(E)-{(5-chloro-benzo[b]thiophen-3-yl)-[2-(3,5-dichloro-phenyl)-vinylcarbamoyl]-methyl}-phosphonic acid,
(E)-{(5-chloro-benzo[b]thiophen-3-yl)-[2-(2,4-difluoro-phenyl)-vinylcarbamoyl]-methyl}-phosphonic acid,
(E)-{(5-chloro-benzo[b]thiophen-3-yl)-[2-(3-amino-phenyl)-vinylcarbamoyl]-methyl}-phosphonic acid,
(E)-{(5-chloro-benzo[b]thiophen-3-yl)-[2-(2-methoxy-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-trifluoromethoxy-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-methoxy-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2,6-difluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2-chloro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-chloro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3,5-difluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2,3-difluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2-bromo-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2,3-dimethoxy-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-nitro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-bromo-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3,5-dimethoxy-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2,5-difluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3,5-dichloro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2,4-difluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-amino-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2-methoxy-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-trifluoromethoxy-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-methoxy-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2,6-difluoro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2-chloro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-chloro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3,5-difluoro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2,3-difluoro-phenyl)-vinylcarbamoyl]-methyl}-phosphonic acid bis-(tert-butylcarbonyloxymethyl)ester, (E)-{(5-chloro-benzo[b]thiophen-3-yl)-[2-(2-bromo-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2,3-dimethoxy-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-nitro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-bromo-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3,5-dimethoxy-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2,5-difluoro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3,5-dichloro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2,4-difluoro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-amino-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2-methoxy-phenyl)-vinylcarbamoyl]-methyl}-phosphonic acid (tert-butylcarbonyloxymethyl)ester,
(E)-{(5-chloro-benzo[b]thiophen-3-yl)-[2-(3-trifluoromethoxy-phenyl)-vinylcarbamoyl]-methyl}-phosphonic acid (tert-butylcarbonyloxymethyl)ester,
(E)-{(5-chloro-benzo[b]thiophen-3-yl)-[2-(3-methoxy-phenyl)-vinylcarbamoyl]-methyl}-phosphonic acid (tert-butylcarbonyloxymethyl)ester,
(E)-{(5-chloro-benzo[b]thiophen-3-yl)-[2-(2,6-difluoro-phenyl)-vinylcarbamoyl]-methyl}-phosphonic acid (tert-butylcarbonyloxymethyl)ester,
(E)-{(5-chloro-benzo[b]thiophen-3-yl)-[2-(2-chloro-phenyl)-vinylcarbamoyl]-methyl}-phosphonic acid (tert-butylcarbonyloxymethyl)ester,
(E)-{(5-chloro-benzo[b]thiophen-3-yl)-[2-(3-chloro-phenyl)-vinylcarbamoyl]-methyl}-phosphonic acid (tert-butylcarbonyloxymethyl)ester,
(E)-{(5-chloro-benzo[b]thiophen-3-yl)-[2-(3,5-difluoro-phenyl)-vinylcarbamoyl]-methyl}-phosphonic acid (tert-butylcarbonyloxymethyl)ester,
(E)-{(5-chloro-benzo[b]thiophen-3-yl)-[2-(2,3-difluoro-phenyl)-vinylcarbamoyl]-methyl}-phosphonic acid (tert-butylcarbonyloxymethyl)ester,
(E)-{(5-chloro-benzo[b]thiophen-3-yl)-[2-(2-bromo-phenyl)-vinylcarbamoyl]-methyl}-phosphonic acid (tert-butylcarbonyloxymethyl)ester,
(E)-{(5-chloro-benzo[b]thiophen-3-yl)-[2-(2,3-dimethoxy-phenyl)-vinylcarbamoyl]-methyl}-phosphonic acid (tert-butylcarbonyloxymethyl)ester,
(E)-{(5-chloro-benzo[b]thiophen-3-yl)-[2-(3-nitro-phenyl)-vinylcarbamoyl]-methyl}-phosphonic acid (tert-butylcarbonyloxymethyl)ester,
(E)-{(5-chloro-benzo[b]thiophen-3-yl)-[2-(3-bromo-phenyl)-vinylcarbamoyl]-methyl}-phosphonic acid (tert-butylcarbonyloxymethyl)ester,
(E)-{(5-chloro-benzo[b]thiophen-3-yl)-[2-(3,5-dimethoxy-phenyl)-vinylcarbamoyl]-methyl}-phosphonic acid (tert-butylcarbonyloxymethyl)ester,
(E)-{(5-chloro-benzo[b]thiophen-3-yl)-[2-(2,5-difluoro-phenyl)-vinylcarbamoyl]-methyl}-phosphonic acid (tert-butylcarbonyloxymethyl)ester,
(E)-{(5-chloro-benzo[b]thiophen-3-yl)-[2-(3,5-dichloro-phenyl)-vinylcarbamoyl]-methyl}-phosphonic acid (tert-butylcarbonyloxymethyl)ester,
(E)-{(5-chloro-benzo[b]thiophen-3-yl)-[2-(2,4-difluoro-phenyl)-vinylcarbamoyl]-methyl}-phosphonic acid (tert-butylcarbonyloxymethyl)ester,
(E)-{(5-chloro-benzo[b]thiophen-3-yl)-[2-(3-amino-phenyl)-vinylcarbamoyl]-methyl}-phosphonic acid (tert-butylcarbonyloxymethyl)ester,
(E)-2-{(5-chloro-benzo[b]thiophen-3-yl)-[2-(2-methoxy-phenyl)-vinylcarbamoyl]-methyl}-1,3,2-dioxaphosphorinane 2-oxide,
(E)-2-{(5-chloro-benzo[b]thiophen-3-yl)-[2-(3-trifluoromethoxy-phenyl)-vinylcarbamoyl]-methyl}-1,3,2-dioxaphosphorinane 2-oxide,
(E)-2-{(5-chloro-benzo[b]thiophen-3-yl)-[2-(3-methoxy-phenyl)-vinylcarbamoyl]-methyl}-1,3,2-dioxaphosphorinane 2-oxide,
(E)-2-{(5-chloro-benzo[b]thiophen-3-yl)-[2-(2,6-difluoro-phenyl)-vinylcarbamoyl]-methyl}-1,3,2-dioxaphosphorinane 2-oxide,
(E)-2-{(5-chloro-benzo[b]thiophen-3-yl)-[2-(2-chloro-phenyl)-vinylcarbamoyl]-methyl}-1,3,2-dioxaphosphorinane 2-oxide,
(E)-2-{(5-chloro-benzo[b]thiophen-3-yl)-[2-(3-chloro-phenyl)-vinylcarbamoyl]-methyl}-1,3,2-dioxaphosphorinane 2-oxide,
(E)-2-{(5-chloro-benzo[b]thiophen-3-yl)-[2-(3,5-difluoro-phenyl)-vinylcarbamoyl]-methyl}-1,3,2-dioxaphosphorinane 2-oxide,
(E)-2-{(5-chloro-benzo[b]thiophen-3-yl)-[2-(2,3-difluoro-phenyl)-vinylcarbamoyl]-methyl}-1,3,2-dioxaphosphorinane 2-oxide,
(E)-2-{(5-chloro-benzo[b]thiophen-3-yl)-[2-(2-bromo-phenyl)-vinylcarbamoyl]-methyl}-1,3,2-dioxaphosphorinane 2-oxide,
(E)-2-{(5-chloro-benzo[b]thiophen-3-yl)-[2-(2,3-dimethoxy-phenyl)-vinylcarbamoyl]-methyl}-1,3,2-dioxaphosphorinane 2-oxide,
(E)-2-{(5-chloro-benzo[b]thiophen-3-yl)-[2-(3-nitro-phenyl)-vinylcarbamoyl]-methyl}-1,3,2-dioxaphosphorinane 2-oxide,
(E)-2-{(5-chloro-benzo[b]thiophen-3-yl)-[2-(3-bromo-phenyl)-vinylcarbamoyl]-methyl}-1,3,2-dioxaphosphorinane 2-oxide,
(E)-2-{(5-chloro-benzo[b]thiophen-3-yl)-[2-(3,5-dimethoxy-phenyl)-vinylcarbamoyl]-methyl}-1,3,2-dioxaphosphorinane 2-oxide,
(E)-2-{(5-chloro-benzo[b]thiophen-3-yl)-[2-(2,5-difluoro-phenyl)-vinylcarbamoyl]-methyl}-1,3,2-dioxaphosphorinane 2-oxide,
(E)-2-{(5-chloro-benzo[b]thiophen-3-yl)-[2-(3,5-dichloro-phenyl)-vinylcarbamoyl]-methyl}-1,3,2-dioxaphosphorinane 2-oxide,
(E)-2-{(5-chloro-benzo[b]thiophen-3-yl)-[2-(2,4-difluoro-phenyl)-vinylcarbamoyl]-methyl}-1,3,2-dioxaphosphorinane 2-oxide,
(E)-2-{(5-chloro-benzo[b]thiophen-3-yl)-[2-(3-amino-phenyl)-vinylcarbamoyl]-methyl}-1,3,2-dioxaphosphorinane 2-oxide,
(E)-{(5-chloro-benzo[b]thiophen-3-yl)-[2-(2-methoxy-phenyl)-vinylcarbamoyl]-methyl}-phosphonic acid (isopropyloxycarbonyloxymethyl)ester, (E)-{(5-chloro-benzo[b]thiophen-3-yl)-[2-(3-trifluoromethoxy-phenyl)-vinylcarbamoyl]-methyl}-phosphonic acid (isopropyloxycarbonyloxymethyl)ester,
(E)-{(5-chloro-benzo[b]thiophen-3-yl)-[2-(3-methoxy-phenyl)-vinylcarbamoyl]-methyl}-phosphonic acid (isopropyloxycarbonyloxymethyl)ester,
(E)-{(5-chloro-benzo[b]thiophen-3-yl)-[2-(2,6-difluoro-phenyl)-vinylcarbamoyl]-methyl}-phosphonic acid (isopropyloxycarbonyloxymethyl)ester,
(E)-{(5-chloro-benzo[b]thiophen-3-yl)-[2-(2-chloro-phenyl)-vinylcarbamoyl]-methyl}-phosphonic acid (isopropyloxycarbonyloxymethyl)ester,
(E)-{(5-chloro-benzo[b]thiophen-3-yl)-[2-(3-chloro-phenyl)-vinylcarbamoyl]-methyl}-phosphonic acid (isopropyloxycarbonyloxymethyl)ester,
(E)-{(5-chloro-benzo[b]thiophen-3-yl)-[2-(3,5-difluoro-phenyl)-vinylcarbamoyl]-methyl}-phosphonic acid (isopropyloxycarbonyloxymethyl)ester,
(E)-{(5-chloro-benzo[b]thiophen-3-yl)-[2-(2,3-difluoro-phenyl)-vinylcarbamoyl]-methyl}-phosphonic acid (isopropyloxycarbonyloxymethyl)ester,
(E)-{(5-chloro-benzo[b]thiophen-3-yl)-[2-(2-bromo-phenyl)-vinylcarbamoyl]-methyl}phosphonic acid (isopropyloxycarbonyloxymethyl)ester,
(E)-{(5-chloro-benzo[b]thiophen-3-yl)-[2-(2,3-dimethoxy-phenyl)-vinylcarbamoyl]-methyl}-phosphonic acid (isopropyloxycarbonyloxymethyl)ester,
(E)-{(5-chloro-benzo[b]thiophen-3-yl)-[2-(3-nitro-phenyl)-vinylcarbamoyl]-methyl}-phosphonic acid (isopropyloxycarbonyloxymethyl)ester,
(E)-{(5-chloro-benzo[b]thiophen-3-yl)-[2-(3-bromo-phenyl)-vinylcarbamoyl]-methyl}-phosphonic acid (isopropyloxycarbonyloxymethyl)ester,
(E)-{(5-chloro-benzo[b]thiophen-3-yl)-[2-(3,5-dimethoxy-phenyl)-vinylcarbamoyl]-methyl}-phosphonic acid (isopropyloxycarbonyloxymethyl)ester,
(E)-{(5-chloro-benzo[b]thiophen-3-yl)-[2-(2,5-difluoro-phenyl)-vinylcarbamoyl]-methyl}-phosphonic acid (isopropyloxycarbonyloxymethyl)ester,
(E)-{(5-chloro-benzo[b]thiophen-3-yl)-[2-(3,5-dichloro-phenyl)-vinylcarbamoyl]-methyl}-phosphonic acid (isopropyloxycarbonyloxymethyl)ester,
(E)-{(5-chloro-benzo[b]thiophen-3-yl)-[2-(2,4-difluoro-phenyl)-vinylcarbamoyl]-methyl}-phosphonic acid (isopropyloxycarbonyloxymethyl)ester,
(E)-{(5-chloro-benzo[b]thiophen-3-yl)-[2-(3-amino-phenyl)-vinylcarbamoyl]-methyl}-phosphonic acid (isopropyloxycarbonyloxymethyl)ester,
(E)-{(5-chloro-benzo[b]thiophen-3-yl)-[2-(3-fluoro-5-chloro-phenyl)-vinylcarbamoyl]-methyl}-methyl-phosphinic acid,
(E)-{(5-chloro-benzo[b]thiophen-3-yl)-[2-(2-fluoro-3-chloro-phenyl)-vinylcarbamoyl]-methyl}-methyl-phosphinic acid,
(E)-{(5-chloro-benzo[b]thiophen-3-yl)-[2-(3-chloro-4-fluoro-phenyl)-vinylcarbamoyl]-methyl}-methyl-phosphinic acid,
(E)-{(5-chloro-benzo[b]thiophen-3-yl)-[2-(2-fluoro-5-chloro-phenyl)-vinylcarbamoyl]-methyl}-methyl-phosphinic acid,
(E)-{(5-chloro-benzo[b]thiophen-3-yl)-[2-(3,5-dibromo-phenyl)-vinylcarbamoyl]-methyl}-methyl-phosphinic acid,
(E)-{(5-chloro-benzo[b]thiophen-3-yl)-[2-(3-cyano-phenyl)-vinylcarbamoyl]-methyl}-methyl-phosphinic acid,
(E)-{(5-chloro-benzo[b]thiophen-3-yl)-[2-(2-cyano-phenyl)-vinylcarbamoyl]-methyl}-methyl-phosphinic acid,
(E)-{(5-chloro-benzo[b]thiophen-3-yl)-[2-(3-fluoro-5-trifluoromethyl-phenyl)-vinylcarbamoyl]-methyl}-methyl-phosphinic acid,
(E)-{(5-chloro-benzo[b]thiophen-3-yl)-[2-(3-fluoro-5-chloro-phenyl)-vinylcarbamoyl]-methyl}-phosphonic acid,
(E)-{(5-chloro-benzo[b]thiophen-3-yl)-[2-(2-fluoro-3-chloro-phenyl)-vinylcarbamoyl]-methyl}-phosphonic acid,
(E)-{(5-chloro-benzo[b]thiophen-3-yl)-[2-(3-chloro-4-fluoro-phenyl)-vinylcarbamoyl]-methyl}-phosphonic acid,
(E)-{(5-chloro-benzo[b]thiophen-3-yl)-[2-(2-fluoro-5-chloro-phenyl)-vinylcarbamoyl]-methyl}-phosphonic acid,
(E)-{(5-chloro-benzo[b]thiophen-3-yl)-[2-(3,5-dibromo-phenyl)-vinylcarbamoyl]-methyl}-phosphonic acid,
(E)-{(5-chloro-benzo[b]thiophen-3-yl)-[2-(3-cyano-phenyl)-vinylcarbamoyl]-methyl}-phosphonic acid,
(E)-{(5-chloro-benzo[b]thiophen-3-yl)-[2-(2-cyano-phenyl)-vinylcarbamoyl]-methyl}-phosphonic acid,
(E)-{(5-chloro-benzo[b]thiophen-3-yl)-[2-(3-fluoro-5-trifluoromethyl-phenyl)-vinylcarbamoyl]-methyl}-phosphonic acid,
(E)-{(5-chloro-benzo[b]thiophen-3-yl)-[2-(3-fluoro-5-chloro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2-fluoro-3-chloro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-chloro-4-fluoro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2-fluoro-5-chloro-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3,5-dibromo-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-cyano-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(2-cyano-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-fluoro-5-trifluoromethyl-phenyl)-vinylcarbamoyl]-methyl}-methyl-phosphinic acid (tert-butylcarbonyloxymethyl)ester,
(E)-{(5-chloro-benzo[b]thiophen-3-yl)-[2-(3-fluoro-5-chloro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2-fluoro-3-chloro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-chloro-4-fluoro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(2-fluoro-5-chloro-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3,5-dibromo-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-cyano-phenyl)-vinylcarbamoyl]-methyl}-phosphonic acid bis-(tert-butylcarbonyloxymethyl)ester, (E)-{(5-chloro-benzo[b]thiophen-3-yl)-[2-(2-cyano-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-fluoro-5-trifluoromethyl-phenyl)-vinylcarbamoyl]-methyl}-phosphonic acid bis-(tert-butylcarbonyloxymethyl)ester,
(E)-{(5-chloro-benzo[b]thiophen-3-yl)-[2-(3-fluoro-5-chloro-phenyl)-vinylcarbamoyl]-methyl}-phosphonic acid (tert-butylcarbonyloxymethyl)ester,
(E)-{(5-chloro-benzo[b]thiophen-3-yl)-[2-(2-fluoro-3-chloro-phenyl)-vinylcarbamoyl]-methyl}-phosphonic acid (tert-butylcarbonyloxymethyl)ester,
(E)-{(5-chloro-benzo[b]thiophen-3-yl)-[2-(3-chloro-4-fluoro-phenyl)-vinylcarbamoyl]-methyl}-phosphonic acid (tert-butylcarbonyloxymethyl)ester,
(E)-{(5-chloro-benzo[b]thiophen-3-yl)-[2-(2-fluoro-5-chloro-phenyl)-vinylcarbamoyl]-methyl}-phosphonic acid (tert-butylcarbonyloxymethyl)ester,
(E)-{(5-chloro-benzo[b]thiophen-3-yl)-[2-(3,5-dibromo-phenyl)-vinylcarbamoyl]-methyl}-phosphonic acid (tert-butylcarbonyloxymethyl)ester,
(E)-{(5-chloro-benzo[b]thiophen-3-yl)-[2-(3-cyano-phenyl)-vinylcarbamoyl]-methyl}-phosphonic acid (tert-butylcarbonyloxymethyl)ester,
(E)-{(5-chloro-benzo[b]thiophen-3-yl)-[2-(2-cyano-phenyl)-vinylcarbamoyl]-methyl}-phosphonic acid (tert-butylcarbonyloxymethyl)ester,
(E)-{(5-chloro-benzo[b]thiophen-3-yl)-[2-(3-fluoro-5-trifluoromethyl-phenyl)-vinylcarbamoyl]-methyl}-phosphonic acid (tert-butylcarbonyloxymethyl)ester,
(E)-2-{(5-chloro-benzo[b]thiophen-3-yl)-[2-(3,4-difluoro-phenyl)-vinylcarbamoyl]-methyl}-1,3,2-dioxaphosphorinane 2-oxide,
(E)-2-{(5-chloro-benzo[b]thiophen-3-yl)-[2-(2-fluoro-3-chloro-phenyl)-vinylcarbamoyl]-methyl}-1,3,2-dioxaphosphorinane 2-oxide,
(E)-2-{(5-chloro-benzo[b]thiophen-3-yl)-[2-(3-chloro-4-fluoro-phenyl)-vinylcarbamoyl]-methyl}-1,3,2-dioxaphosphorinane 2-oxide,
(E)-2-{(5-chloro-benzo[b]thiophen-3-yl)-[2-(2-fluoro-5-chloro-phenyl)-vinylcarbamoyl]-methyl}-1,3,2-dioxaphosphorinane 2-oxide,
(E)-2-{(5-chloro-benzo[b]thiophen-3-yl)-[2-(3,5-dibromo-phenyl)-vinylcarbamoyl]-methyl}-1,3,2-dioxaphosphorinane 2-oxide,
(E)-2-{(5-chloro-benzo[b]thiophen-3-yl)-[2-(3-cyano-phenyl)-vinylcarbamoyl]-methyl}-1,3,2-dioxaphosphorinane 2-oxide,
(E)-2-{(5-chloro-benzo[b]thiophen-3-yl)-[2-(2-cyano-phenyl)-vinylcarbamoyl]-methyl}-1,3,2-dioxaphosphorinane 2-oxide,
(E)-2-{(5-chloro-benzo[b]thiophen-3-yl)-[2-(3-fluoro-5-trifluoromethyl-phenyl)-vinylcarbamoyl]-methyl}-1,3,2-dioxaphosphorinane 2-oxide,
(E)-{(5-chloro-benzo[b]thiophen-3-yl)-[2-(3-fluoro-5-chloro-phenyl)-vinylcarbamoyl]-methyl}-phosphonic acid (isopropyloxycarbonyloxymethyl)ester,
(E)-{(5-chloro-benzo[b]thiophen-3-yl)-[2-(2-fluoro-3-chloro-phenyl)-vinylcarbamoyl]-methyl}-phosphonic acid (isopropyloxycarbonyloxymethyl)ester,
(E)-{(5-chloro-benzo[b]thiophen-3-yl)-[2-(3-chloro-4-fluoro-phenyl)-vinylcarbamoyl]-methyl}-phosphonic acid (isopropyloxycarbonyloxymethyl)ester,
(E)-{(5-chloro-benzo[b]thiophen-3-yl)-[2-(2-fluoro-5-chloro-phenyl)-vinylcarbamoyl]-methyl}-phosphonic acid (isopropyloxycarbonyloxymethyl)ester,
(E)-{(5-chloro-benzo[b]thiophen-3-yl)-[2-(3,5-dibromo-phenyl)-vinylcarbamoyl]-methyl}-phosphonic acid (isopropyloxycarbonyloxymethyl)ester,
(E)-{(5-chloro-benzo[b]thiophen-3-yl)-[2-(3-cyano-phenyl)-vinylcarbamoyl]-methyl}-phosphonic acid (isopropyloxycarbonyloxymethyl)ester,
(E)-{(5-chloro-benzo[b]thiophen-3-yl)-[2-(2-cyano-phenyl)-vinylcarbamoyl]-methyl}-phosphonic acid (isopropyloxycarbonyloxymethyl)ester, and
(E)-{(5-chloro-benzo[b]thiophen-3-yl)-[2-(3-fluoro-5-trifluoromethyl-phenyl)-vinylcarbamoyl]-methyl}-phosphonic acid (isopropyloxycarbonyloxymethyl) ester.

9. The process of claim 8, wherein the compound is selected from the group consisting of:
2    (E)-{(5-chloro-benzo[b]thiophen-3-yl)-[2-(3,4-difluoro-phenyl)-vinylcarbamoyl]-methyl}-phosphonic acid,
17    (E)-{(5-chloro-benzo[b]thiophen-3-yl)-[2-(3,4-difluoro-phenyl)-vinylcarbamoyl]-methyl}-methyl-phosphinic acid,
164    (E)-{(5-chloro-benzo[b]thiophen-3-yl)-[2-(3,5-dichloro-phenyl)-vinylcarbamoyl]-methyl}-methyl-phosphinic acid,
181    (E)-{(5-chloro-benzo[b]thiophen-3-yl)-[2-(3,4-difluoro-phenyl)-vinylcarbamoyl]-methyl}-phosphonic acid (tert-butylcarbonyloxymethyl)ester,
185    (E)-{(5-chloro-benzo[b]thiophen-3-yl)-[2-(3,4-difluoro-phenyl)-vinylcarbamoyl]-methyl}-phosphonic acid [(isopropoxycarbonyloxy)-methyl]ester,
201    (E)-{(5-chloro-benzo[b]thiophen-3-yl)-[2-(3,5-dichloro-phenyl)-vinylcarbamoyl]-methyl}-phosphonic acid,
255    (E)-{(5-chloro-benzo[b]thiophen-3-yl)-[2-(3,5-dichloro-phenyl)-vinylcarbamoyl]-methyl}-phosphonic acid (tert-butylcarbonyloxymethyl)ester, and
297    (E)-{(5-chloro-benzo[b]thiophen-3-yl)-[2-(3,5-dichloro-phenyl)-vinylcarbamoyl]-methyl}-phosphonic acid (isopropyloxycarbonyloxymethyl)ester.

10. A process for preparing a compound of Formula (Ia) or a salt thereof:

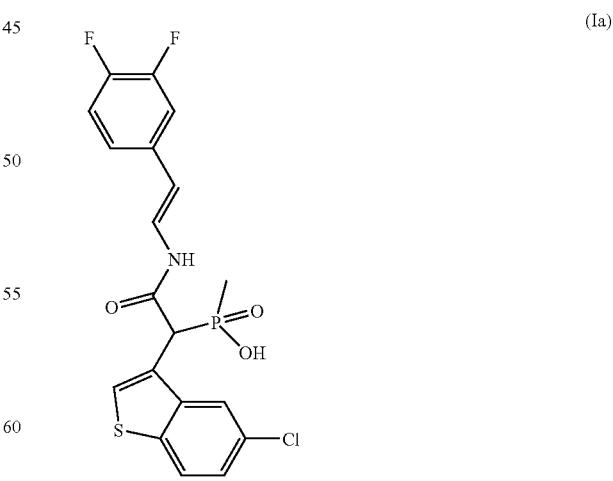

(Ia)

comprising the steps of:
Step 1. reacting a Compound B1 with a Compound B3, wherein Compound B1 and Compound B3 are present in a first ratio, in toluene, to provide a Compound B5

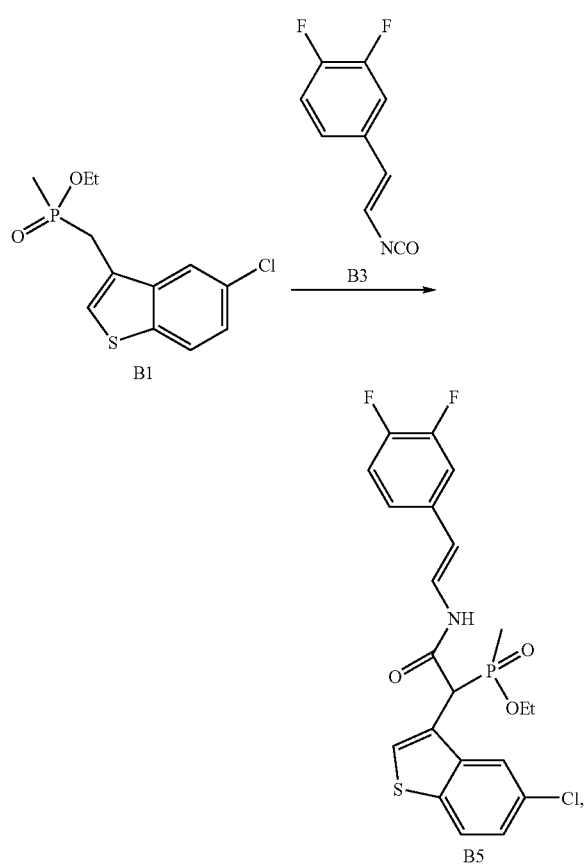

wherein in the first ratio, the amount of Compound B1 exceeds the amount of Compound B3 by about 0.2 equivalents; and Step 2. reacting the Compound B5 in the presence of TMSBr in acetonitrile and optionally present pyridine, wherein TMSBr and Compound B5 are in a second ratio, and wherein TMSBr and pyridine, when pyridine is present, are in a third ratio, to provide the compound of Formula (Ia):

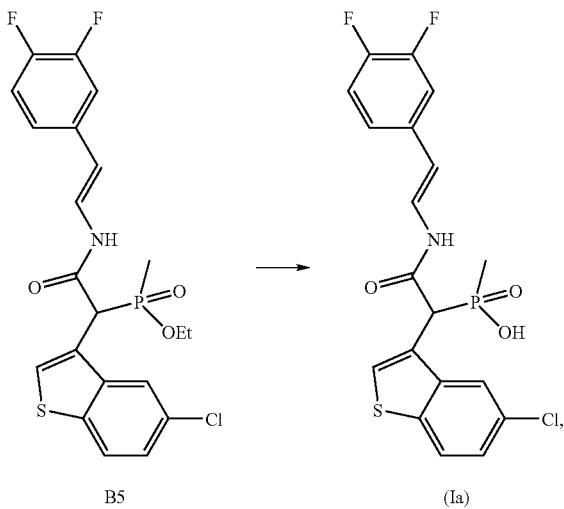

wherein the second ratio of TMSBr:Compound B5 is in a range of about 2.5:1 to about 2:1, and wherein the third ratio of TMSBr:pyridine, when pyridine is present, is in a range of from about 1:1 to about 1:2.

11. The process of claim 10, further comprising the step of:

Step 3. reacting the compound of Formula (Ia) with choline hydroxide, in a mixture of MeOH and EtOAc, wherein MeOH and EtOAc are in a fourth ratio, to provide a Compound D1 as a salt, representative of a compound of Formula (I), wherein the salt is obtained by direct crystallization:

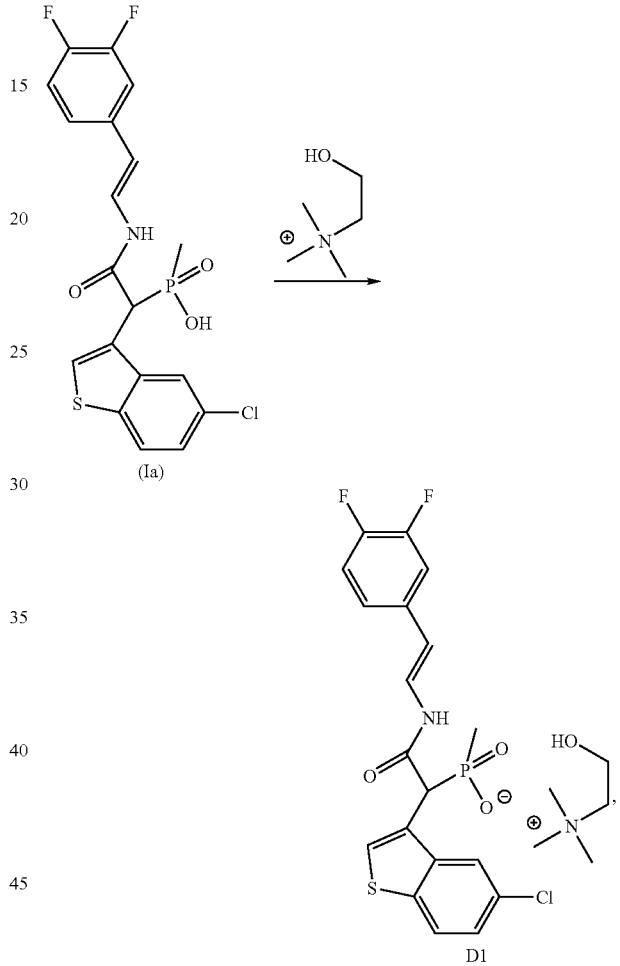

wherein the fourth ratio of MeOH:EtOAc is about 1:3.

12. The process of claim 10, wherein an amount of Compound B1 is in a range of from about 1.2 equivalents to about 1 equivalent and an amount of Compound B3 is in a range of from about 1 equivalent to about 0.8 equivalents according to said first ratio.

13. The process of claim 10, wherein the ratio of TMSBr:Compound B5 is in a range of about 2.5:1 to about 2:1, according to said second ratio, and the ratio of TMSBr:pyridine is in a range of about 1:1 to about 1:2, according to said third ratio.

14. The process of claim 10, wherein the third ratio of TMSBr:pyridine is about 1:2.

15. The process of claim 10, wherein the ratio of TMSBr:Compound B5 is in a range of about 2.5:1 to about 2:1, according to said second ratio, wherein pyridine is not present.

* * * * *